US012594330B2

(12) United States Patent
Pravetoni et al.

(10) Patent No.: US 12,594,330 B2
(45) Date of Patent: Apr. 7, 2026

(54) ANTI-OPIOID COMPOUNDS AND METHODS OF MAKING AND USING SAME

(71) Applicants:REGENTS OF THE UNIVERSITY OF MINNESOTA, Minneapolis, MN (US); HENNEPIN HEALTHCARE RESEARCH INSTITUTE, Minneapolis, MN (US)

(72) Inventors: Marco Pravetoni, Minneapolis, MN (US); Carly Baehr, Minneapolis, MN (US)

(73) Assignees: REGENTS OF THE UNIVERSITY OF MINNESOTA, Minneapolis, MN (US); HENNEPIN HEALTHCARE RESEARCH INSTITUTE, Minneapolis, MN (US)

( * ) Notice: Subject to any disclaimer, the term of this patent is extended or adjusted under 35 U.S.C. 154(b) by 1040 days.

(21) Appl. No.: 17/616,031

(22) PCT Filed: Jun. 4, 2020

(86) PCT No.: PCT/US2020/036060
§ 371 (c)(1),
(2) Date: Dec. 2, 2021

(87) PCT Pub. No.: WO2020/247584
PCT Pub. Date: Dec. 10, 2020

(65) Prior Publication Data
US 2022/0296707 A1 Sep. 22, 2022

Related U.S. Application Data

(60) Provisional application No. 62/857,020, filed on Jun. 4, 2019.

(51) Int. Cl.
*A61K 39/395* (2006.01)
*C07K 16/44* (2006.01)

(52) U.S. Cl.
CPC ........ *A61K 39/39533* (2013.01); *C07K 16/44* (2013.01); *C07K 2317/565* (2013.01)

(58) Field of Classification Search
CPC ........ A61K 39/39533; A61K 2039/505; C07K 16/44; C07K 2317/565; C07K 2317/56
See application file for complete search history.

(56) References Cited

U.S. PATENT DOCUMENTS

| | | | |
|---|---|---|---|
| 4,741,900 A | 5/1988 | Alvarez et al. | |
| 5,223,409 A | 6/1993 | Ladner et al. | |
| 2002/0197270 A1* | 12/2002 | Cohen .................... | A61P 35/00 514/44 R |
| 2011/0136137 A1 | 6/2011 | Borlak et al. | |
| 2017/0306031 A1 | 10/2017 | Shen et al. | |

FOREIGN PATENT DOCUMENTS

| | | | | | |
|---|---|---|---|---|---|
| CN | 108048406 A | * | 5/2018 | | |
| TW | 201143795 A1 | | 12/2011 | | |
| WO | WO 1990/002809 A1 | | 3/1990 | | |
| WO | WO 1991/017271 A1 | | 11/1991 | | |
| WO | WO 1992/001047 A1 | | 1/1992 | | |
| WO | WO 1992/009690 A2 | | 6/1992 | | |
| WO | WO 1992/015679 A1 | | 9/1992 | | |
| WO | WO 1992/018619 A1 | | 10/1992 | | |
| WO | WO 1992/020791 A1 | | 11/1992 | | |
| WO | WO 1993/001288 A1 | | 1/1993 | | |
| WO | WO 2016/139297 A1 | | 9/2016 | | |
| WO | WO 2017/196943 A1 | | 11/2017 | | |
| WO | WO 2018/080838 A1 | | 5/2018 | | |
| WO | WO 2018/081642 A1 | | 5/2018 | | |
| WO | WO-2018222689 A1 | * | 12/2018 | ........... | A61K 9/0029 |

OTHER PUBLICATIONS

Rudikoff et al., Proc Natl Acad Sci USA , vol. 79 p. 1979 (Year: 1982).*
Pascalis et al. The Journal of Immunology, 169: 3076-3084 (Year: 2002).*
Casset et al., BBRC 307, 198-205 (Year: 2003).*
Ausubel, Current Protocols in Molecular Biology; John Wiley: New York NY: 1994. Cover page, copyright page, table of contents.
Baruffaldi et al., Preclinical Efficacy and Characterization of Candidate Vaccines for Treatment of Opioid Use Disorders Using Clinically Viable Carrier Proteins. *Mol Pharm* 15, 4947-4962 (2018).
Chothia et al., Canonical structures for the hypervariable regions of immunoglobulins. *J Mol Biol* 196, 901-917 (1987).
Davis et al., Basic Methods in Molecular Biology, Elsevier Science Publishing Co., Inc., New York, New York, 1986, Cover page, title page and table of contents.
Fox et al., Risk factors for severe respiratory depression from prescription opioid overdose. *Addiction* 113, 59-66 (2018).
Goding, *Monoclonal Antibodies: Principles and Practice,* Academic Press, 1986, Cover page, title page, table of contents, and pp. 59-103.
Harlow et al., *Antibodies: A Laboratory Manual,* Cold Spring Harbor Laboratory Press: Cold Spring Harbor, NY; 1988. Cover page, title page, and table of contents (22 pages).
Ho et al., Refined protocol for generating monoclonal antibodies from single human and murine B cells. *J Immunol Methods* 438, 67-70 (2016).

(Continued)

*Primary Examiner* — Kimberly Ballard
*Assistant Examiner* — Stacey N Macfarlane
(74) *Attorney, Agent, or Firm* — Mueting Raasch Group

(57) ABSTRACT

This disclosure describes opioid-specific monoclonal antibodies (mAb), methods of making those antibodies, and methods of using those antibodies. The methods include, for example, treating a subject with an opioid use disorder or neonatal opioid withdrawal syndrome or preventing and reversing opioid overdose in a subject. Additionally or alternatively, the antibodies may be used to detect opioids including, for example, in a screening, diagnostic, or forensic assay.

12 Claims, 23 Drawing Sheets
Specification includes a Sequence Listing.

(56) References Cited

OTHER PUBLICATIONS

Holliger et al., "Diabodies": small bivalent and bispecific antibody fragments. *Proc Natl Acad Sci U S A* 90, 6444-6448 (1993).

International Patent Application No. PCT/US2020/036060, filed Jun. 4, 2020; International Search Report and Written Opinion mailed Feb. 9, 2021, 10 pages.

International Patent Application No. PCT/US2020/036060, filed Jun. 4, 2020; International Preliminary Report on Patentability dated Dec. 7, 2021, 6 pages.

Jones et al., Replacing the complementarity-determining regions in a human antibody with those from a mouse. *Nature* 321, 522-525 (1986).

Kabat, Sequences of Proteins of Immunological Interest, Fifth Edition, U.S. Department of Health and Human Services, NIH Publication No. 91-3242. 1991. Cover page, table of contents.

Kohler et al., Derivation of specific antibody-producing tissue culture and tumor lines by cell fusion. *Eur J Immunol* 6, 511-519 (1976).

Kostelny et al., Formation of a bispecific antibody by the use of leucine zippers. *J Immunol* 148, 1547-1553 (1992).

Laudenbach et al., Blocking interleukin-4 enhances efficacy of vaccines for treatment of opioid abuse and prevention of opioid overdose. *Sci Rep* 8, 5508 (2018).

Laudenbach et al., The frequency of naive and early-activated hapten-specific B cell subsets dictates the efficacy of a therapeutic vaccine against prescription opioid abuse. *J Immunol* 194, 5926-5936 (2015).

Li et al., Synthesis and biological evaluation of fentanyl acrylic derivatives, *RSC Adv.* 7, 20015-20019 (2017).

Orlandi et al., Cloning immunoglobulin variable domains for expression by the polymerase chain reaction. *Proc Natl Acad Sci U S A* 86, 3833-3837 (1989).

Pravetoni et al., An oxycodone conjugate vaccine elicits drug-specific antibodies that reduce oxycodone distribution to brain and hot-plate analgesia. *J Pharmacol Exp Ther* 341, 225-232 (2012).

Pravetoni et al., Co-administration of morphine and oxycodone vaccines reduces the distribution of 6-monoacetylmorphine and oxycodone to brain in rats. *Vaccine* 30, 4617-4624 (2012).

Raleigh et al., A Fentanyl Vaccine Alters Fentanyl Distribution and Protects against Fentanyl-Induced Effects in Mice and Rats. *J Pharmacol Exp Ther* 368, 282-291 (2019).

Raleigh et al., Selective effects of a morphine conjugate vaccine on heroin and metabolite distribution and heroin-induced behaviors in rats. *J Pharmacol Exp Ther* 344, 397-406 (2013).

Sambrook et al., *Molecular Cloning: A Laboratory Manual,* Second Edition, , Cold Spring Harbor Laboratory Press: Cold Spring Harbor, NY; 1989. Cover page, title page, and table of contents.

Singer, "Optimal humanization of 1B4, an anti-CD18 murine monoclonal antibody, is achieved by correct choice of human V-region framework sequences" 1993 *J. Immunol.,* 150(7):2844-57.

Smith et al., Phage Display. *Chem Rev* 97, 391-410 (1997).

Smith, "Comparison of Biosequences" 1981 *Advances in Applied Mathematics,* 2:482-489.

Smith et al., Monoclonal Antibodies for Combating Synthetic Opioid Intoxication. *J Am Chem Soc* 141, 10489-10503 (2019).

Songsivilai et al., Bispecific antibody: a tool for diagnosis and treatment of disease. *Clin Exp Immunol* 79, 315-321 (1990).

Spanier et al., Efficient generation of monoclonal antibodies against peptide in the context of MHCII using magnetic enrichment. *Nat Commun* 7, 11804 (2016).

Takeda et al., Construction of chimaeric processed immunoglobulin genes containing mouse variable and human constant region sequences. *Nature* 314, 452-454 (1985).

Taylor et al., Hapten-specific naive B cells are biomarkers of vaccine efficacy against drugs of abuse. *J Immunol Methods* 405, 74-86 (2014).

Traunecker et al., Bispecific single chain molecules (Janusins) target cytotoxic lymphocytes on HIV infected cells. *EMBO J* 10, 3655-3659 (1991).

Traunecker et al., Janusin: new molecular design for bispecific reagents. *Int J Cancer Suppl* 7, 51-52 (1992).

* cited by examiner

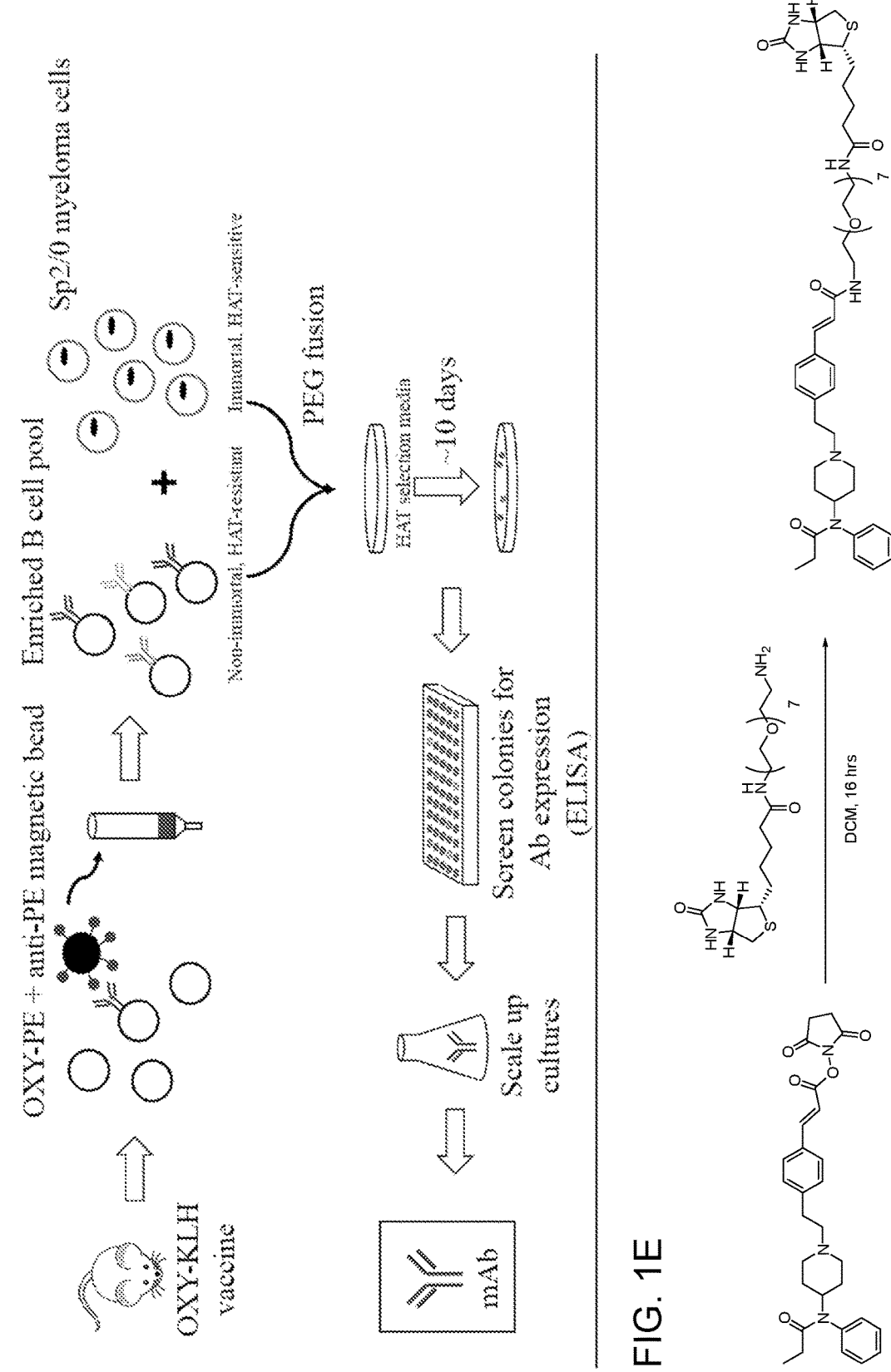

FIG. 1B

OXY-sKLH

FIG. 1C

MOR-sKLH

FIG. 1D

F-sKLH

■ HY1
▦ HY2
▩ HY1 and HY2

FIG. 5C
FIG. 5D
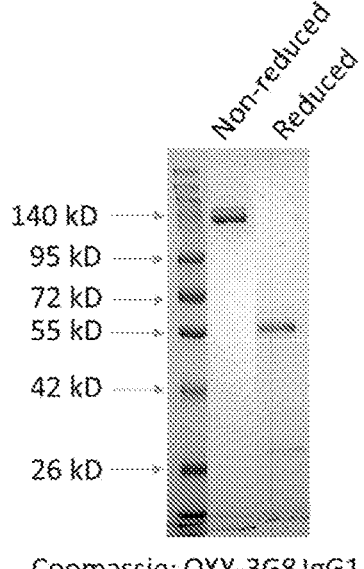
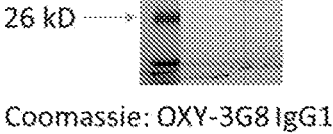
Coommassie: OXY-3G8 IgG1
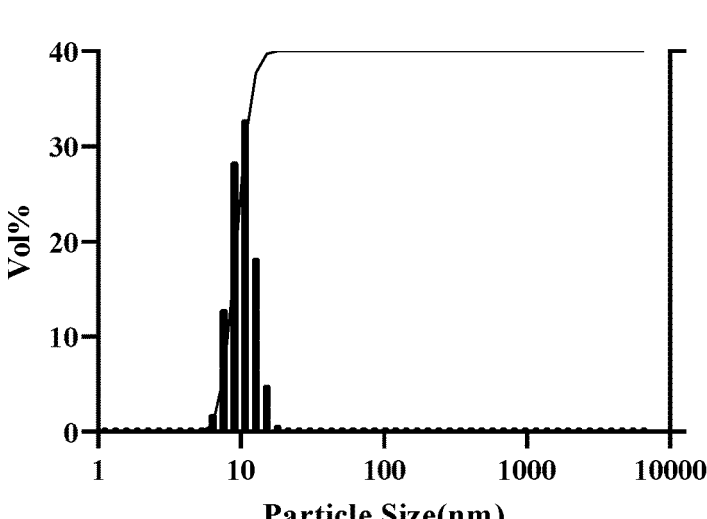
FIG. 5E
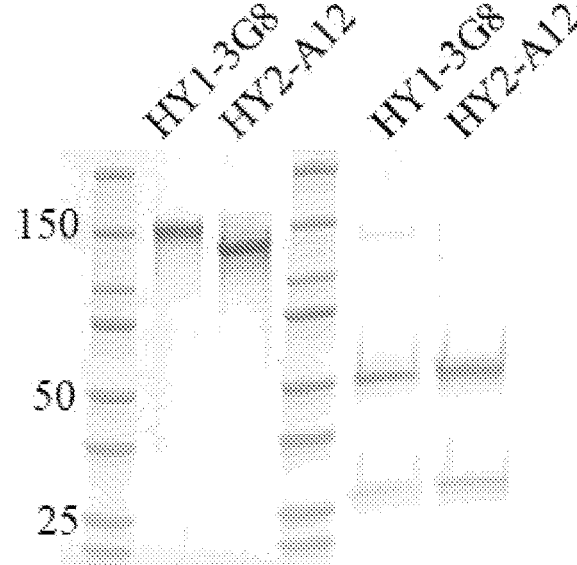

FIG. 6A

```
>Canonical HC_____                                          {---CDR1---}
>HY1_1D10_____                            GCL[GYNFSDYYIN]WVKQRTGQ
>HY1_1F12_____                        MKVSCKAT[VYTFSSHWIE]WIKQRPGH
>HY1_3B1_____                          LSCKAS[DHTFTDYYIN]WMKQRTGQ
>HY1_3C10_____                         KLSCKAS[DHTFTDYYIN]WMKQRTGQ
>HY1_3E3_____           QVQLQESGAELMKPGASVKISCKATG[YTFSNYWIE ]WVKQRPGH
>HY1_3G4_____                     KISCKATG[YTFSNYWIE ]WVKQRPGH
>HY1_3G8_____           EVKLLESGGGLVQPGGSPELSCAASG[FDFSRYWMS ]WVRQAPGK
>HY1-3H5_____      GEFEVQLQESGAELVKPGASVKLSCKASG[YTFTSQWMQ ]WVRQRPGQ
>HY1_3H7_____              GASVKLSCKASG[YTFTSQWMQ ]WVRQRPGQ
>HY1_3H9_____              GASVKLSCKASG[YTFTSQWMQ ]WVRQRPGQ
>HY2_A6_____                  RYPARLL[ATQSRSYWIE]WVKQRPGH
>HY2_A8_____                   RISCEATG[YTISSY WIE]WVKQRPGH
>HY2_A12_____           QVQLQESGAELARPGASVKLSCKAS[GYTSTDYYIN]WVKQRTGQ
>HY2_B2_____              HGLTELLSLCPSPALSLS[YSITSDYAWN]WIRQFPGN
>HY2_B5_____           QLQESGAELMKPGASVKISCEATG[YTISSY WIE]WVKQRPGH
>HY2_B9_____              GASVKLSCKASG[YTFTSQWMQ ]WVRQRPGQ
>HY2_B10_____              GASVKLSCKASG[YTFTSQWMQ ]WVRQRPGQ
>HY2_C6_____                                  GTGSGRFPGN
>HY2_C7_____                  LSCAASG[FDFSRYWMS ]WVRQAPGK
>HY2_D1_____                                  GTGSGRFPGN >Canonical HC_____      {-----CDR2-----}
1-1D10_____    GLE[WIGEIYPGSGTTYY]NEKFKGKATLTADKSSSTAYMQLSSLTSEDSTV
1-1F12_____    GLE[WIGEILPGSGSTNY]NEKFKGKATFTADTSSNVAYMQLTSLTSEDSAV
1-3B1_____    GLE[WIGEIYPGSGYTYY]NEKFKGKATLTADKSSSTAYMQLSSLTSEDSAV
1-3C10_____    GLE[WIGEIYPGSGYTYY]NEKFKGKATLTADKSSSTAYMQLSSLTSEDSAV
1-3E3_____    GLE[WIGEILPGSGSTYH]NENFKGKATFTADTSSNTAYMQLITLTSEDSAV
1-3G4_____    GLE[WIGEILPGSGSTYH]NENFKGKATFTADTSSNTAYMQLITLTSEDSAV
1-3G8_____    GLE[WIGEINPDSSTINY]TPSLKDKFIISRDNAKNTLYLQMRKVRSEDTAL
1-3H5_____    GLE[WIGEINPSSGRTHY]NEKFKTKATLTVDKSSSTAYMQLSSLTSEDSAV
1-3H7_____    GLE[WIGEINPSSGRTHY]NEKFKTKATLTVDKSSSTAYMQLSSLTSEDSAV
1-3H9_____    GLE[WIGEINPSSGRTHY]NEKFKTKATLTVDKSSSTAYMQLSSLTSEDSAV
2-A6_____    GLE[WIGEILPGSGSTTY]NEKFKGKATFTADTSSNTAYMQLSSLTSEDSAA
2-A8_____    GLE[WIGEILPGSGSTTY]NEKFKGKATFTADTSSNTAYMQLSSLTSEDSAA
2-A12_____    GLE[WIGEIYPGSGNTYY]NEKFKGKATLTADKSSSTAYMQLSSLTSEDSAV
2-B2_____    KLE[WMGYIGYSGGTSY ]NPSLKSRISITRDTSKNQFFLHLNSVTTEDTAT
2-B5_____    GLE[WIGEILPGSGSTTY]NEKFKGKATFTADTSSNTAYMQLSSLTSEDSAA
2-B9_____    GLE[WIGEINPSSGRTHY]NEKFKTKATLTVDKSSSTAYMQLSSLTSEDSAV
2-B10_____    GLE[WIGEINPSSGRTHY]NEKFKTKATLTVDKSSSTAYMQLSSLTSEDSAV
2-C6_____    KLE[WLGYISYSGTTSY ]NPSLKSRISITRDTSKNQSFLQLNSVTTEDTAT
2-C7_____    GLE[WIGEVNPDSSTINS]TPSLKDKFFISRDNAKNTLYLQMIKVRSEDTAL
2-D1_____    KLE[WLGYISYSGTTSY ]NPSLKSRISITRDTSQNQSFLQLNSVTTEDTAT
```

FIG. 6B

```
>Canonical HC          {-------CDR3------}                AKTTPPSVYPLAPGSAAQT
1-1D10          YFC[AGGSSLYVW      FAY]WGQGTLVTVSAAKTTPPSVYPLAPGSAAQT
1-1F12          YYC[ARYE        YGNYV]WGQGTLVTVSAAKTTPPSVYPLAPGSAAQT
1-3B1           YFC[ARGDGYYFW      FGY]WGQGTLVTVSAAKTTPPSVYPLAPGSAAQT
1-3C10          YFC[ARGDGYYFW      FGY]WGQGTLVTVSAAKTTPPSVYPLAPGSAAQT
1-3E3           YYC[ATGSRLA W      FVY]WGQGTLVNVSAAKTTPPSVYPLAPGSAAQT
1-3G4           YYC[ATGSRLA W      FVY]WGQGTLVNVSAAKTTPPSVYPLAPGSAAQT
1-3G8           YYC[SRVLLYYGSNPHWHFDV]WGAGTTVTVSSAKTTPPSVYPLAPGSAAQT
1-3H5           YYC[ARGDGDYVW      FAY]WGQGTLVTVSAAKTTPPSVYPLAPGSAAQT
1-3H7           YYC[ARGDGDYVW      FAY]WGQGTLVTVSAAKTTPPSVYPLAPGSAAQT
1-3H9           YYC[ARGDGDYVW      FAY]WGQGTLVTVSAAKTTPPSVYPLAPGSAAQT
2-A6            YYC[ARARTGTNYYT    MDY]WGQGTSVTVSSAKTTPPSVYPLAPGSAAQT
2-A8            YYC[ARARTGTNYYT    MDY]WGQGTSVTVSSAKTTPPSVYPLAPGSAAQT
2-A12           YFC[TRGGVYYGYDDAW  FVY]WGQGTLVTVSAAKTTA
2-B2            YFC[AREITTTGC      FAY]WGQGTLVTVSAAKTTPPSVYPLAPGSAAQT
2-B5            YYC[ARARTGTNYYT    MDY]WGQGTSVTVSSAKTTPPSVYPLAPGSAAQT
2-B9            YYC[ARGDGDYVW      FAY]WGQGTLVTVSAAKTTPPSVYPLAPGSAAQT
2-B10           YYC[ARGDGDYVW      FAY]WGQGTLVTVSAAKTTPPSVYPLAPGSAAQT
2-C6            YYC[AREVTTTGW      FVY]WGQGTLVTVSAAKTTP
2-C7            YYC[ARLYYNYVDYYA   MDY]WGQGTSVTVSSAKTTPPSVYPLAPGSAAQT
2-D1            YYC[AREVTTTGW      FVY]WGQGTLVTVSAAKTTPPSVY >Canonical HC     NSMVTLGCLVKGYFPEPVTVTWNSGSLSSGVHTFPAVLQSDLYTLSSSVTVP
1-1D10            NSMVTLGCLVKGYFPEPVTVTWNSGSLSSGV
1-1F12            NSMVTLGCLVKGYFPEPVTVTWNSGSLSSGVH
1-3B1            NSMVTLGCLVKGYFTEPVTVT
1-3C10           NSMVTLGCLVKGYFPEPVTVTWNSGSLSSGV
1-3E3            NSMVTLGCLVKGYFPEPVTVTWNSGSLSRGV
1-3G4            NSMVTLGCLVKGYFPEPVTVTWNSGSLW
1-3G8            NSMVTLGCLVKGYFPEPVTVTWNSGSLSSGVTTL
1-3H5            NSMVTLGCLVKGYFPEPVTVTWNSGSLSSGVHTF
1-3H7            NSMVTLGCLVKGYFPEPVTVTWNSGSLSSGVHTF
1-3H9            NSMVTLGCLVKGYFPEPVTVTWNSGSLSSGVHTF
2-A6             NSMVTLGCLVKGYFPEPVTVTWNSG
2-A8             NSMVTLGCLVKGYFPEPVTVTWNSGSLSSGV
2-A12
2-B2             NSMVTLGCLVKGYFPEPVTVTWNSGS
2-B5             NSMVTLGCLVKGYFPEPVTVTWNSGSLSSGV
2-B9             NSMVTLGCLVKGYFPEPVTVTWNSGSLSSGV
2-B10            NSMVTLGCLVKGYFPEPVTVTWNSGSLSSGV
2-C6
2-C7             NSMVTLGCLVKGYFPEPVTVTWNSGSLSSG
2-D1

>Canonical HC     SSPRPSETVTCNVAHPASSTKVDKKIVPRDCGCKPCICTVPEVSSVFIFPPK
>Canonical HC     PKDVLTITLTPKVTCVVVDISKDDPEVQFSWFVDDVEVHTAQTQPREEQFNS
>Canonical HC     TFRSVSELPIMHQDWLNGKEFKCRVNSAAFPAPIEKTISKTKGRPKAPQVYT
>Canonical HC     IPPPKEQMAKDKVSLTCMITDFFPEDITVEWQWNGQPAENYKNTQPIMNTNG
>Canonical HC     SYFVYSKLNVQKSNWEAGNTFTCSVLHEGLHNHHTEKSLSHSPGK
```

FIG. 6C

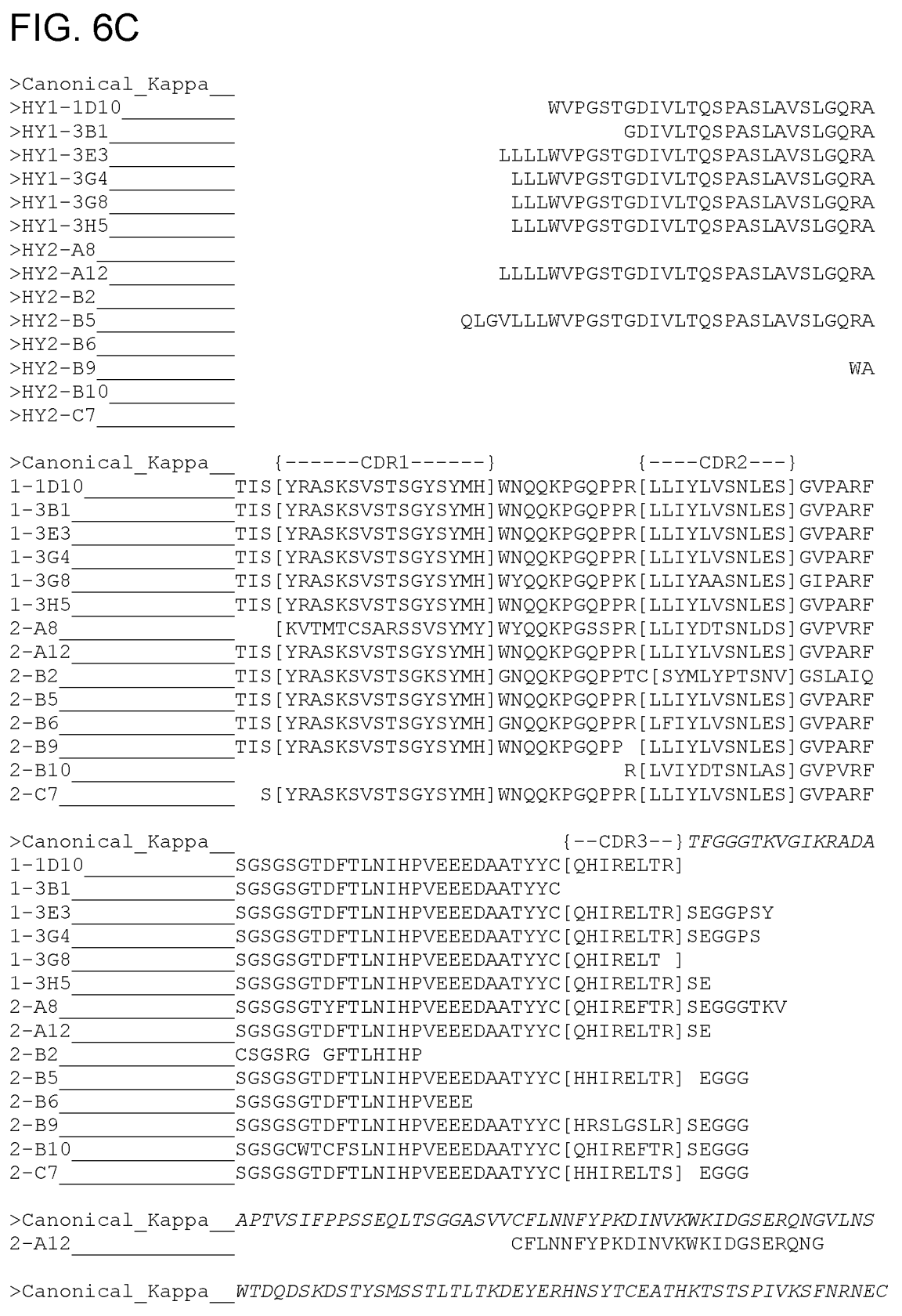

```
>Canonical_Kappa__
>HY1-1D10_____                                    WVPGSTGDIVLTQSPASLAVSLGQRA
>HY1-3B1_____                                       GDIVLTQSPASLAVSLGQRA
>HY1-3E3_____                                 LLLLWVPGSTGDIVLTQSPASLAVSLGQRA
>HY1-3G4_____                                  LLLWVPGSTGDIVLTQSPASLAVSLGQRA
>HY1-3G8_____                                  LLLWVPGSTGDIVLTQSPASLAVSLGQRA
>HY1-3H5_____                                  LLLWVPGSTGDIVLTQSPASLAVSLGQRA
>HY2-A8_____
>HY2-A12_____                                 LLLLWVPGSTGDIVLTQSPASLAVSLGQRA
>HY2-B2_____
>HY2-B5_____                            QLGVLLLWVPGSTGDIVLTQSPASLAVSLGQRA
>HY2-B6_____
>HY2-B9_____                                                          WA
>HY2-B10_____
>HY2-C7_____

>Canonical_Kappa__       {------CDR1------}              {----CDR2---}
1-1D10_____     TIS[YRASKSVSTSGYSYMH]WNQQKPGQPPR[LLIYLVSNLES]GVPARF
1-3B1_____     TIS[YRASKSVSTSGYSYMH]WNQQKPGQPPR[LLIYLVSNLES]GVPARF
1-3E3_____     TIS[YRASKSVSTSGYSYMH]WNQQKPGQPPR[LLIYLVSNLES]GVPARF
1-3G4_____     TIS[YRASKSVSTSGYSYMH]WNQQKPGQPPR[LLIYLVSNLES]GVPARF
1-3G8_____     TIS[YRASKSVSTSGYSYMH]WYQQKPGQPPK[LLIYAASNLES]GIPARF
1-3H5_____     TIS[YRASKSVSTSGYSYMH]WNQQKPGQPPR[LLIYLVSNLES]GVPARF
2-A8_____         [KVTMTCSARSSVSYMY]WYQQKPGSSPR[LLIYDTSNLDS]GVPVRF
2-A12_____     TIS[YRASKSVSTSGYSYMH]WNQQKPGQPPR[LLIYLVSNLES]GVPARF
2-B2_____     TIS[YRASKSVSTSGKSYMH]GNQQKPGQPPTC[SYMLYPTSNV]GSLAIQ
2-B5_____     TIS[YRASKSVSTSGYSYMH]WNQQKPGQPPR[LLIYLVSNLES]GVPARF
2-B6_____     TIS[YRASKSVSTSGYSYMH]GNQQKPGQPPR[LFIYLVSNLES]GVPARF
2-B9_____     TIS[YRASKSVSTSGYSYMH]WNQQKPGQPP [LLIYLVSNLES]GVPARF
2-B10_____                             R[LVIYDTSNLAS]GVPVRF
2-C7_____       S[YRASKSVSTSGYSYMH]WNQQKPGQPPR[LLIYLVSNLES]GVPARF >Canonical_Kappa__                             {--CDR3--}TFGGGTKVGIKRADA
1-1D10_____     SGSGSGTDFTLNIHPVEEEDAATYYC[QHIRELTR]
1-3B1_____     SGSGSGTDFTLNIHPVEEEDAATYYC
1-3E3_____     SGSGSGTDFTLNIHPVEEEDAATYYC[QHIRELTR]SEGGPSY
1-3G4_____     SGSGSGTDFTLNIHPVEEEDAATYYC[QHIRELTR]SEGGPS
1-3G8_____     SGSGSGTDFTLNIHPVEEEDAATYYC[QHIRELT ]SE
1-3H5_____     SGSGSGTDFTLNIHPVEEEDAATYYC[QHIRELTR]SE
2-A8_____     SGSGSGTYFTLNIHPVEEEDAATYYC[QHIREFTR]SEGGGTKV
2-A12_____     SGSGSGTDFTLNIHPVEEEDAATYYC[QHIRELTR]SE
2-B2_____     CSGSRG GFTLHIHP
2-B5_____     SGSGSGTDFTLNIHPVEEEDAATYYC[HHIRELTR] EGGG
2-B6_____     SGSGSGTDFTLNIHPVEEE
2-B9_____     SGSGSGTDFTLNIHPVEEEDAATYYC[HRSLGSLR]SEGGG
2-B10_____     SGSGCWTCFSLNIHPVEEEDAATYYC[QHIREFTR]SEGGG
2-C7_____     SGSGSGTDFTLNIHPVEEEDAATYYC[HHIRELTS] EGGG >Canonical_Kappa__ APTVSIFPPSSEQLTSGGASVVCFLNNFYPKDINVKWKIDGSERQNGVLNS
2-A12_____                     CFLNNFYPKDINVKWKIDGSERQNG >Canonical_Kappa__ WTDQDSKDSTYSMSSTLTLTKDEYERHNSYTCEATHKTSTSPIVKSFNRNEC
```

FIG. 8A

```
HY-3 (Anti-Heroin, Anti-6-acetyl-morphine, and Anti-Morphine)
>Canonical HC_____            >                  {---CDR1--}
>HY3-1A2_____      VQLQESGAELMKPGASVKISCKATG[YKFSSYWID]WVRQRPGH
>HY3-1G4_____    EFEVQLQESGADLVRSGASVKLSCTASG[FNIKDYYIH]WVKQRPEQ
>HY4-1F9_____                     MKISCKATG[YKFSSYWID]WVRQRPGH >Canonical HC_____      {-----CDR2----- }
>HY3-1A2_____    GLE[WIGEILPGSSSSYY ]NEKFKGKATFTADTSSNTASMQLSSLTSED
>HY3-1G4_____    GLE[WIGWIDPENGDTEYD] PKFQGKATMSADTSSNTAYLQLSSLTSED
>HY4-1F9_____    GLE[WIGEILPGSSSSYY ]NEKFKGKATFTADTSSNTASMQLSSLTSED >Canonical HC_____         {---CDR3----}           AKTTPPSVYPLAPGSAAQT
>HY3-1A2_____    SAVYYCA[RWDTYYWY FDV]WGAGTTVTVSSAKTTPPSVYPLAPGSAAQT
>HY3-1G4_____    TAVYYCN[SSTMITTALFAY]WGQGTLVTVSSAAKTTPP
>HY4-1F9_____    SAVYYCA[RWDTYYWY FDV]WGAGTTVTVSSAKTTPPSVYPLAPGSAAQT >Canonical HC_____   NSMVTLGCLVKGYFPEPVTVTWNSGSLSSGVHTFPAVLQSDLYTL
>HY3-1A2_____    NSH
>HY4-1F9_____    NSMVTLGCLVKGYFPEPVTVTWNSGSLSSG
```

*>Canonical HC_____ SSSVTVPSSPRPSETVTCNVAHPASSTKVDKKIVPRDCGCKPCICTVPEVSSVF*
*IFPPKPKDVLTITLTPKVTCVVVDISKDDPEVQFSWFVDDVEVHTAQTQPREEQFNSTFRSVSELPIMHQDWLNG*
*KEFKCRVNSAAFPAPIEKTISKTKGRPKAPQVYTIPPPKEQMAKDKVSLTCMITDFFPEDITVEWQWN*
*GQPAENYKNTQPIMNTNGSYFVYSKLNVQKSNWEAGNTFTCSVLHEGLHNHHTEKSLSHSPGK*

```
>Canonical_Kappa__                      >
>HY3-1A2_____            LLLWVPGSTGDIVLTQSPASLAVS
>HY3-1E4_____        QLQLGVLLLWVPGSTGDIVLTQSPASLAVS
>HY3-1G4_____          QLGVLLLWVPGSTGDIVLTQSPASLAVS
>HY4-1A6_____                 RGDILLTQFPAILSVS
>HY4-1F9_____                   TQSPAILSVS >Canonical_Kappa__        {------CDR1------}          {----CDR2
>HY3-1A2_____    LGQRATIS[YRASKSVSTSGYSYMH]WNQQKPGQPPR[LLIYLVSN
>HY3-1E4_____    LGQRATIS[YRASKSVSTSGYSYMH]WNQQKPGQPPR[LLIYLVSN
>HY3-1G4_____    LGQRATIS[CKASHSVDYDGDRYMN]WYQQKPGQPPK[LLIYVASN
>HY4-1A6_____    PGERVSFS[CRASQSI   GTSTH]WYQQKPGQPPR[IIIYFESI
>HY4-1F9_____    PGERVSFS[CRASQSI   GTSTH]WYQQKPGQPPR[IIIYFVSN >Canonical_Kappa__---}                               {--CDR3--}
>HY3-1A2_____    LES]GVPARFSGSGSGTDFTLNIHPVEEEDAATYYC[SHIRELTR]
>HY3-1E4_____    LES]GVPARFSGSGSGTDFTLNIHPVEEEDAATYYC[QHIRELTR]
>HY3-1G4_____    LEC]GIPARFSGSGCGTDFTLNIHPVEEEDGATYYC[QRSNEDPF]
>HY4-1A6_____    LEF]GARFRFSGTGSGTDFTLNIHELEEEDATYQY[QHIREITR]
>HY4-1F9_____    LEF]GVPFRFSGTGSGTDFTLNIHQLEEEDDATYHC[QHIRELTR]
```

*>Canonical_Kappa__ TFGGGTKVGIKRADAAPTVSIFPPSSEQLTSGGASVVCFLNNFYP*
*>Canonical_Kappa__ KDINVKWKIDGSERQNGVLNSWTDQDSKDSTYSMSSTLTLTKDEYE*
*>Canonical_Kappa__ RHNSYTCEATHKTSTSPIVKSFNRNEC*

FIG. 8B

```
HY-5,6 (Anti-Fentanyl)
>Canonical HC_____             >                    {---CDR1--}
>HY6-B5_____       FEVQLQESGPELVKPGASVKVSCKASG[YAFTSYNIY]WVKQSHGK
>HY6-D12_____
>HY6-F9_____        QVQESGAELVKPGASVKLSCKASG[YTFTSQWMQ]WVRQRPGQ
>HY6-F11_____                                       YWNWIRKFPGN >Canonical HC_____     {------CDR2-----}
>HY6-B5_____      SLE[WIGYIDPYNGGTTYN]QNFKGKATLTVDKSSSTAYMHLNSLTSE
>HY6-D12_____                         YNEKFTGKATLTADKSSSTAYMQLSSLTSE
>HY6-F9_____       GLE[WIGEINPSSGRTHYN]EKFKTKATLTVDKSSSTAYMQLSSLTSE
>HY6-F11_____      KLE[YMGYI SYSGSTYY ]NPSLKSRISITRDTSKNQYSLHLNSVTA >Canonical HC_____          {-----CDR3-----}        AKTTPPSVYPLAP
>HY6-B5_____      DSAVYYCA[SEIYYDYGGR FAY]WGQGTLVTVSAAKTTPPSVYPLAP
>HY6-D12_____      DSAVYFCA[REEYDYDEGYAMDY]WGQGTSVTVSSAKTTPPSVYPLAP
>HY6-F9_____       DSAVYYCA[RGDGDYVW    FAY]WGQGTLVTVSAAKTTPPSVYPLAP
>HY6-F11_____      EDTATFYCA[RYYGDNYVGAMDY]WGQGTSVTVSSAKTTAPSVYPLAP >Canonical HC_____    GSAAQTNSMVTLGCLVKGYFPEPVTVTWNSGSLSSGVHTFPAVLQ
>HY6-B5_____     GSAAQTNSMVTLGCLVKGYFPEPVTVTWNSGSLSSGVHTFPAVLQ
>HY6-D12_____     GSAAQTNSMVTLGCLVKGYFPEPVTVTWNSGSLSSGVHT
>HY6-F9_____      GSAAQTNSMVTLGCLVKGYFPEPVTVTWNSGSLSSGVHTFPAVLQ
>HY6-F11_____     VCGDTTGSSVTLGCLVKGYFPEPVTLTWNSGSLSSGV >Canonical HC
SDLYTLSSSVTVPSSPRPSETVTCNVAHPASSTKVDKKIVPRDCGCKPCICTVPEVSSVFIFPPKPKDVLTITLTPK
VTCVVVDISKDDPEVQFSWFVDDVEVHTAQTQPREEQFNSTFRSVSELPIMHQDWLNGKEFKCRVNSAAFPAPIEKT
ISKTKGRPKAPQVYTIPPPKEQMAKDKVSLTCMITDFFPEDITVEWQWNGQPAENYKNTQPIMNTNGSYFVYSKLNV
QKSNWEAGNTFTCSVLHEGLHNHHTEKSLSHSPGK >Canonical_Kappa__                             >
>HY5-E5_____              LLWVPGSTGDIVLTQSPASLAVSLG
>HY5-H9_____              LLLWVPGSTGDIVLTQSPASLAVSLG
>HY6-B5_____          HRTFYFQLCLVLLWLSGIVLTQSPASLAVSLG
>HY6-F9_____                          IVLTQSPASLAVSLG
>HY6-F12_____      FPPSSEQLTSGGASVMLLLWVPGSTGDIVLTQSPASLAVSLG >Canonical_Kappa__      {------CDR1------}           {----CDR2---}
>HY5-E5_____  QRATIS[YRASKSVSTSGYSYMH]WNQQKPGQPPR[LLIYLVSNLES]
>HY5-H9_____  QRATIS[YRASKSVSTSGYSYMH]WNQQKPGQPPR[LLIYLVSNLES]
>HY6-B5_____  QRATIS[YRASKSVSTSGYSYMH]WNQQKPGQPPR[LLIYLVSNLES]
>HY6-F9_____  QRATIS[YRASKSVSTSGYSYMH]WNQQKPGQPPR[LLIYLVSNLES]
>HY6-F12_____  QRATIS[YRASKSVSTSGYSYMH]WNQQKPGQPPR[LLIYLVSNLES]

>Canonical_Kappa__                              {--CDR3--}TFGGGT
>HY5-E5_____  GVPARFSGSGSGTDFTLNIHPVEEEDAATYYC[
>HY5-H9_____  GVPARFSGSGSGTDFTLNIHPVEEEDAATYYC[H
>HY6-B5_____  GVPARFSGSGSGTDFTLNIHPVEEEDAATYYC[QHIRELTR]
>HY6-F9_____  GVPARFSGSGSGTDFTLNIHPVEEEDAATYYC[QHIRELTR]SEGGPS
>HY6-F12_____  GVPARFSGSGSGTDFTLNIHPVEEEDA >Canonical_Kappa__ KVGIKRADAAPTVSIFPPSSEQLTSGGASVVCFLNNFYPKDINVKWK
>Canonical_Kappa__ IDGSERQNGVLNSWTDQDSKDSTYSMSSTLTLTKDEYERHNSYTCEAT
>Canonical_Kappa__ HKTSTSPIVKSFNRNEC
```

FIG. 9B

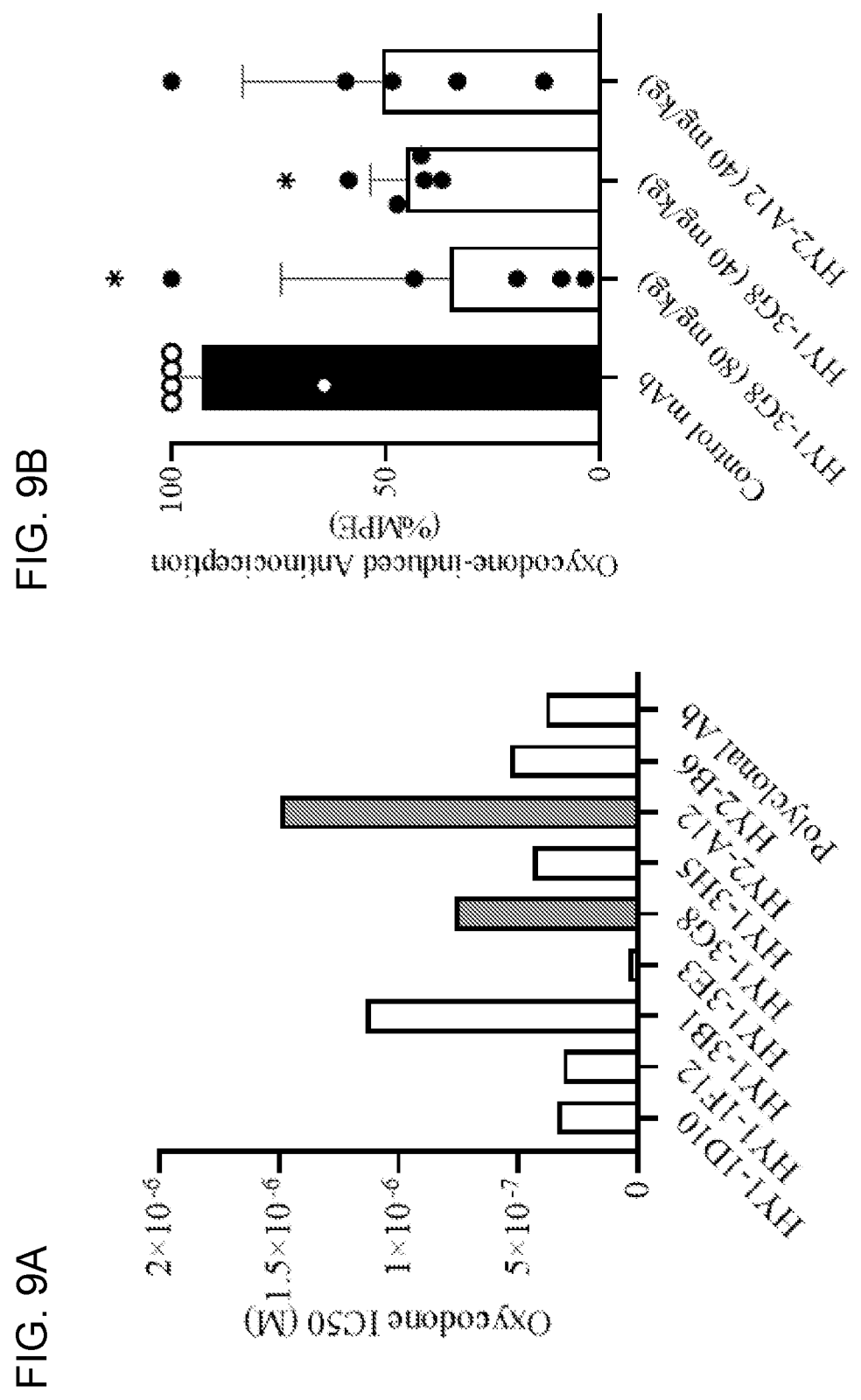

Oxycodone-induced Antinociception (%MPE)

Control mAb
HY1-3G8 (80 mg/kg)
HY1-3G8 (40 mg/kg)
HY2-A12 (40 mg/kg)

FIG. 9A

Oxycodone IC50 (M)

HY1-1D10
HY1-1F12
HY1-3B1
HY1-3E3
HY1-3G8
HY1-3H5
HY2-A12
HY2-B6
Polyclonal Ab

FIG. 10C                        FIG. 10F
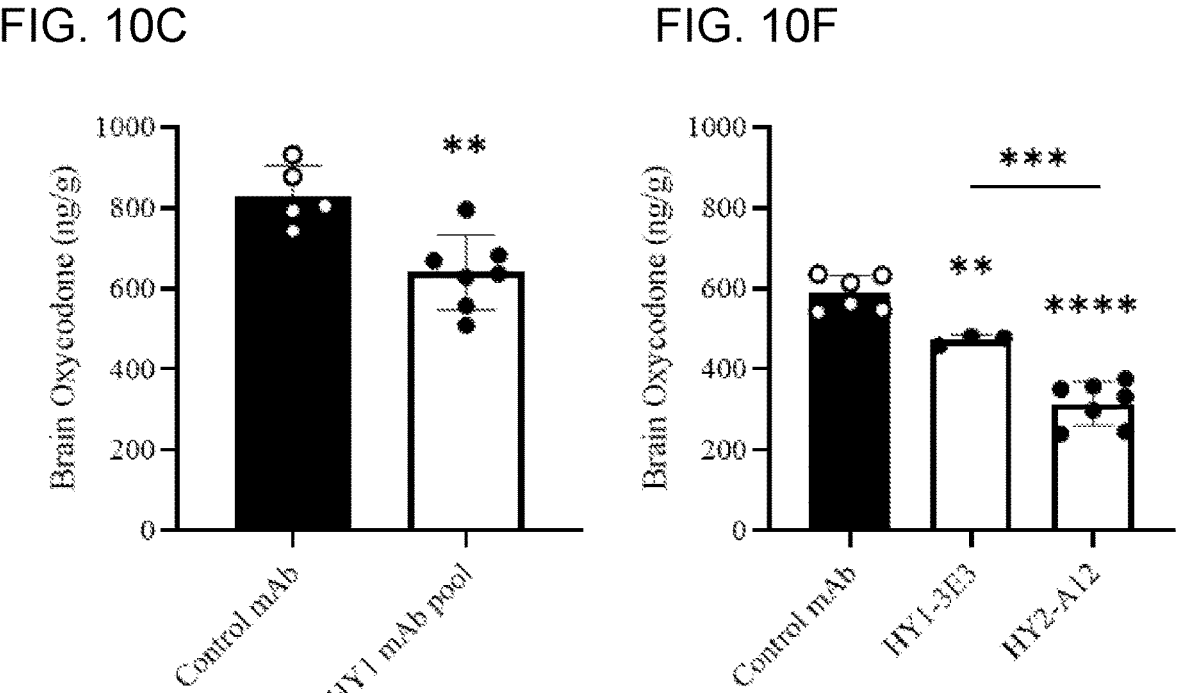

ANTI-OPIOID COMPOUNDS AND METHODS OF MAKING AND USING SAME

CONTINUING APPLICATION DATA

This application is the § 371 U.S. National Stage of International Application No. PCT/US2020/036060, filed Jun. 4, 2020, which claims the benefit of U.S. Provisional Application Ser. No. 62/857,020, filed Jun. 4, 2019, each of which is incorporated by reference herein.

GOVERNMENT FUNDING

This invention was made with government support under DA038876 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "0110_000617WO01_ST25_SL.txt" having a size of 111,284 bytes and created on Jun. 3, 2020. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

BACKGROUND

In the United States, 2.6 million people are dependent on opioids leading to approximately 50,000 opioid-related fatal overdoses in 2017. Although some safe and effective medications are available, only 1 out of 5 opioid addicts benefits from pharmacotherapy. Moreover, as the number of opioid-related fatal overdoses continues to rise, additional therapeutic options to treat opioid use disorder and prevent or reverse opioid overdose are needed. Because synthetic opioids such as fentanyl, carfentanil, and heroin have been included in the Department of Homeland Security Chemical Threat Risk Assessment list, new countermeasures are needed to protect against incapacitation and fatal overdose from exposure to these compounds in Mass Casualty Incidents.

SUMMARY OF THE INVENTION

This disclosure describes opioid-specific monoclonal antibodies (mAb), methods of making those antibodies, and methods of using those antibodies including, for example, to treat opioid use disorder and prevent or reverse opioid overdose. Additionally or alternatively, the mAb may be used to detect opioids including, for example, in a screening assay.

In one aspect, this disclosure describes an anti-opioid antibody, wherein the anti-opioid antibody includes an antibody that binds to the same epitope as an antibody produced by one of the clones of Table 1; or an antibody produced by one of the clones of Table 1.

In another aspect, this disclosure describes an anti-opioid antibody, wherein the anti-opioid antibody includes a monoclonal antibody comprising at least one of a heavy chain variable region of an antibody produced by one or more of the clones of Table 1 or a light chain variable region of an antibody produced by one or more of the clones of Table 1.

In a further aspect, this disclosure describes an anti-opioid antibody, wherein the anti-opioid antibody includes a monoclonal antibody including at least one of a heavy chain variable region comprising one or more complementary determining regions (CDRs) of Table 2A; or a light chain variable region comprising one or more CDRs of Table 2B.

In yet another aspect, this disclosure describes an anti-opioid antibody, wherein the anti-opioid antibody includes each of the CDRs of a heavy chain variable region of a monoclonal antibody produced by one of the clones of Table 1, or each of the CDRs of a light chain variable region of a monoclonal antibody produced by one of the clones of Table 1, or each of the CDRs of a heavy chain variable region of a monoclonal antibody produced by one of the clones of Table 1 and each of the CDRs of a light chain variable region of a monoclonal antibody produced by one of the clones of Table 1. In some embodiments, the CDRs of the heavy chain variable region have an amino acid sequence set forth in Table 2A, or the CDRs of the light chain variable region have an amino acid sequence set forth in Table 2B, or both.

In a further aspect, this disclosure describes an anti-opioid antibody, wherein the anti-opioid antibody including a monoclonal antibody including an amino acid sequence having at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 1; or at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 1, or at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 1 and at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 1.

In one aspect, this disclosure describes an anti-opioid antibody, wherein the anti-opioid antibody includes an antibody that binds to the same epitope as an antibody produced by one of the clones of Table 5; or an antibody produced by one of the clones of Table 5.

In another aspect, this disclosure describes an anti-opioid antibody, wherein the anti-opioid antibody includes a monoclonal antibody comprising at least one of a heavy chain variable region of an antibody produced by one or more of the clones of Table 5 or a light chain variable region of an antibody produced by one or more of the clones of Table 5.

In a further aspect, this disclosure describes an anti-opioid antibody, wherein the anti-opioid antibody includes a monoclonal antibody including at least one of a heavy chain variable region comprising one or more CDRs of Table 7A; or a light chain variable region comprising one or more CDRs of Table 7B.

In yet another aspect, this disclosure describes an anti-opioid antibody, wherein the anti-opioid antibody includes each of the CDRs of a heavy chain variable region of a monoclonal antibody produced by one of the clones of Table 5, or each of the CDRs of a light chain variable region of a monoclonal antibody produced by one of the clones of Table 5, or each of the CDRs of a heavy chain variable region of a monoclonal antibody produced by one of the clones of Table 5 and each of the CDRs of a light chain variable region of a monoclonal antibody produced by one of the clones of Table 5. In some embodiments, the CDRs of the heavy chain variable region have an amino acid sequence set forth in Table 6A, or the CDRs of the light chain variable region have an amino acid sequence set forth in Table 6B, or both.

In a further aspect, this disclosure describes an anti-opioid antibody, wherein the anti-opioid antibody including a monoclonal antibody including an amino acid sequence having at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 5; or at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 5, or at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 5 and at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 5.

In one aspect, this disclosure describes an anti-opioid antibody, wherein the anti-opioid antibody includes an antibody that binds to the same epitope as an antibody produced by one of the clones of Table 7; or an antibody produced by one of the clones of Table 7.

In another aspect, this disclosure describes an anti-opioid antibody, wherein the anti-opioid antibody includes a monoclonal antibody comprising at least one of a heavy chain variable region of an antibody produced by one or more of the clones of Table 7 or a light chain variable region of an antibody produced by one or more of the clones of Table 7.

In a further aspect, this disclosure describes an anti-opioid antibody, wherein the anti-opioid antibody includes a monoclonal antibody including at least one of a heavy chain variable region comprising one or more CDRs of Table 8A; or a light chain variable region comprising one or more CDRs of Table 8B.

In yet another aspect, this disclosure describes an anti-opioid antibody, wherein the anti-opioid antibody includes each of the CDRs of a heavy chain variable region of a monoclonal antibody produced by one of the clones of Table 7, or each of the CDRs of a light chain variable region of a monoclonal antibody produced by one of the clones of Table 7, or each of the CDRs of a heavy chain variable region of a monoclonal antibody produced by one of the clones of Table 7 and each of the CDRs of a light chain variable region of a monoclonal antibody produced by one of the clones of Table 7. In some embodiments, the CDRs of the heavy chain variable region have an amino acid sequence set forth in Table 8A, or the CDRs of the light chain variable region have an amino acid sequence set forth in Table 8B, or both.

In a further aspect, this disclosure describes an anti-opioid antibody, wherein the anti-opioid antibody including a monoclonal antibody including an amino acid sequence having at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 7; or at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 7, or at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 7 and at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 7.

In an additional aspect, this disclosure describes a method including co-administering to a subject: a vaccine comprising an opioid hapten conjugated to a carrier polypeptide, and a cytokine-signaling immunomodulator; isolating antibody-producing cells from the subject; and enriching the antibody-producing cells for cells that bind to the opioid hapten.

In yet another aspect, this disclosure describes a method including identifying a subject, wherein the subject has been exposed to an opioid; isolating antibody-producing cells from the subject; and enriching the antibody-producing cells for a cell that bind to an opioid hapten.

As used herein, the terms "antibody" or "antigen binding fragment thereof" include man-made antibodies such as monoclonal antibodies (mAb) and/or an antigen binding fragments thereof, produced by conventional hybridoma technology, by phage display, recombinant technology, and/or isolated from either B cell lymphocytes or splenocytes of human or animal origin. The terms include both intact immunoglobulin molecules including, for example, a polyclonal antibody, a monoclonal antibody (mAb), a monospecific antibody, a bispecific antibody, a polyspecific antibody, as well as portions, fragments, regions, peptides and derivatives thereof (provided by any known technique, such as, but not limited to, enzymatic cleavage, peptide synthesis, or recombinant techniques), such as, for example, immunoglobulin devoid of light chains, Fab, Fab', F (ab')$_2$, Fv, scFv, antibody fragment, diabody, Fd, CDR regions, or any portion or peptide sequence of the antibody that is capable of binding antigen or epitope. The antibody, or antigen binding fragment thereof, may be a human antibody, a humanized antibody, an animal antibody (for example, camelid antibody), or chimeric antibody. In one embodiment, the "antigen binding fragment thereof" is a single chain antibody, a single chain variable fragment (scFv), a Fab fragment, or a F(ab')2 fragment. The antibody may be of any type (for example, IgG, IgE, IgM, IgD, IgA and IgY), class (for example, IgG1, IgG2, IgG3, IgG4, IgA1 and IgA2), or subclass.

As used herein, the term "monoclonal antibody" refers to an antibody obtained from a population of substantially homogeneous antibodies, that is, the individual antibodies comprising the population are identical except for possible naturally occurring mutations that may be present in minor amounts. The modifier "monoclonal" indicates the character of an antibody, as defined above, as being obtained from a substantially homogeneous population of antibodies and is not to be construed as requiring engineering of the antibody by any particular method.

As used herein, the terms "selective binding of the antibody to a target opioid" and "an antibody that selectively binds to a target opioid" refer to an antibody or antigen binding fragment thereof that binds to a target opioid with at least 50× greater affinity than it binds to another opioid (exogenous or endogenous), opioid receptor agonist, and/or opioid receptor antagonist. In some embodiments, the phrase may include exemplary opioids instead of the terms "target opioid."

As used herein, "isolated" refers to material removed from its original environment (for example, the natural environment if it is naturally occurring), and thus is altered "by the hand of man" from its natural state.

As used herein, "room temperature" is 16° C. to 26° C. or, more preferably, 18° C. to 24° C. In some embodiments, "room temperature" is 20° C. to 22° C.

As used herein "sequence identity" between two polypeptides is determined by comparing the amino acid sequence of one polypeptide to the sequence of a second polypeptide. When discussed herein, whether any particular polypeptide is at least 40 percent (%), at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical to another polypeptide may be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Advances in Applied Mathematics* 2:482-489, to find the best segment of homology between two sequences. When using BESTFIT or any other sequence alignment program to determine whether a particular sequence is, for example, 95% identical to a reference sequence, the parameters are set such that the percentage of identity is calculated over the full length of the reference polypeptide sequence and that gaps in homology of up to 5% of the total number of amino acids in the reference sequence are allowed.

"Binding affinity" or "affinity binding" refers to the strength of the sum total of noncovalent interactions between a single binding site of a molecule (for example, an antibody) and its binding partner (for example, an antigen or antigenic epitope). The affinity of a molecule X for its partner Y may be represented by either the dissociation constant (KD) or the $IC_{50}$, and may generally be determined by immunological techniques known in the art, including, for example, competitive ELISA or similar assays. In some embodiments, antibodies of the present disclosure may be described in terms of their binding affinity for an opioid. In some embodiments, antibodies of the present disclosure include antibodies that interact with a particular antigen wherein the dissociation constant (KD) is less than or equal to $5\times10^{-6}$ M, less than or equal to $1\times10^{-6}$ M, less than or equal to $5\times10^{-7}$ M, less than or equal to $1\times10^{-7}$ M, less than or equal to $5\times10^{-8}$ M, less than or equal to $1\times10^{-8}$ M, less than or equal to $5\times10^{-9}$ M, less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, less than or equal to $1\times10^{-12}$ M, less than or equal to $5\times10^{-13}$ M, less than or equal to $1\times10^{-13}$ M, less than or equal to $5\times10^{-14}$ M, less than or equal to $1\times10^{-14}$ M, less than or equal to $5\times10^{-15}$ M, or less than or equal to $1\times10^{-15}$ M. In an exemplary embodiment, the dissociation constant is determined using competitive ELISA.

As used herein, the term "subject" includes, but is not limited to, humans and non-human vertebrates. In some embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

Unless otherwise specified, "a," "an," "the," and "at least one" are used interchangeably and mean one or more than one.

As used herein, the term "or" is generally employed in its usual sense including "and/or" unless the content clearly dictates otherwise.

The term "and/or" means one or all of the listed elements or a combination of any two or more of the listed elements.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE FIGURES

FIG. 1A shows a schematic of antigen-based magnetic enrichment used to streamline isolation of opioid-specific B cell lymphocytes and generate opioid-specific monoclonal antibodies (mAb). This approach was developed by the inventors, as further described in Example 1, and may be applied to isolation of human and non-human B cells specific for opioids. FIG. 1B shows the structure of the hapten used for immunization for anti-oxycodone hybridomas (see Example 1). FIG. 1B discloses "(Gly)$_4$" as SEQ ID NO: 26. FIG. 1C shows the structure of the hapten used for immunization for anti-morphine (also referred to herein as "M" or "MOR") hybridomas (see Example 2). FIG. 1C discloses "(Gly)$_4$" as SEQ ID NO: 26. FIG. 1D shows the structure of the hapten used for immunization for anti-fentanyl (F) hybridomas (see Example 3). FIG. 1D discloses "(Gly)4" as SEQ ID NO: 26. FIG. 1E shows synthesis of fentanyl-biotin, as further described in Example 3.

FIG. 3A. Dissociation constants (Kd) of mAb were determined by competitive ELISA. (For sets of clones with identical clonotype, Kd shown is the average of all clones in the clonotype.) In vivo efficacy on oxycodone-induced behavior (FIG. 3B) and oxycodone pharmacokinetics (FIG. 3C) of an exemplary anti-oxycodone mAb, clone HY1-3G8, were also evaluated in mice.

FIG. 4A-FIG. 4B. Mice passively immunized with 40 mg/kg mAb were challenged with 2.25 mg/kg oxycodone s.c. Serum (FIG. 4A) and brain (FIG. 4B) oxycodone 30 minutes post-injection. FIG. 4C. Oxycodone-induced antinociception 30 minutes post-injection measured by hot plate latency to respond. FIG. 4D. Oxycodone-specific mAb in serum 24 hours after passive immunization measured by ELISA.

FIG. 5A discloses SEQ ID NOS 105-115, respectively, in order of appearance. FIG. 5C shows SDS-PAGE of anti-oxycodone mAb HY1-3G8, after purification by protein G affinity chromatography. FIG. 5D shows Dynamic light scattering (DLS) of anti-oxycodone mAb HY1-3G8, after purification by protein G affinity chromatography. FIG. 5E-FIG. 5G show SDS-PAGE of purified α-oxycodone mAb HY1-3G8 and HY2-A12 (FIG. 5E), α-heroin mAb HY4-1F9 (FIG. 5F), and α-fentanyl mAb HY6-B5 and HY6-F9 (FIG. 5G). For FIG. 5E-FIG. 5G, samples were analyzed on Criterion Tris-HCl (Bio-Rad, Hercules, CA) 12.5% gels; 2 μg total protein per lane in non-reducing sample buffer (left lanes of each panel), or reduced with 2% 2-mercaptoethanol (right lanes of each panel) with Precision Plus pre-stained molecular weight standards (Bio-Rad). Gels were stained with Coomassie Brilliant Blue and imaged on Gel Doc XR (Bio-Rad).

FIG. 6A-FIG. 6B show an alignment of the protein sequences of the heavy chains of the antibodies of Example 1. FIG. 6A-FIG. 6B disclose SEQ ID NOS 116-125, 125, 126-131, 131 and 132-134, respectively, in order of appearance. FIG. 6C shows an alignment of the protein sequences of the light chains of the antibodies of Example 1. FIG. 6C discloses SEQ ID NOS 135-149, respectively, in order of appearance.

FIG. 8A shows an alignment of the protein sequences of the heavy chains and light chains of exemplary anti-Heroin, anti-6-acetyl-morphine, and anti-morphine mAb. FIG. 8A discloses SEQ ID NOS 116 and 150-158, respectively, in order of appearance. FIG. 8B shows an alignment of the protein sequences of the heavy chains and light chains of exemplary anti-fentanyl mAb. FIG. 8B discloses SEQ ID NOS 116, 159-162, 153 and 163-167, respectively, in order of appearance.

FIG. 9A-FIG. 9D show characterization and efficacy of anti-oxycodone mAb. FIG. 9A. Dissociation constants of anti-oxycodone mAb were determined by competitive

US 12,594,330 B2

9

Figure 9D:
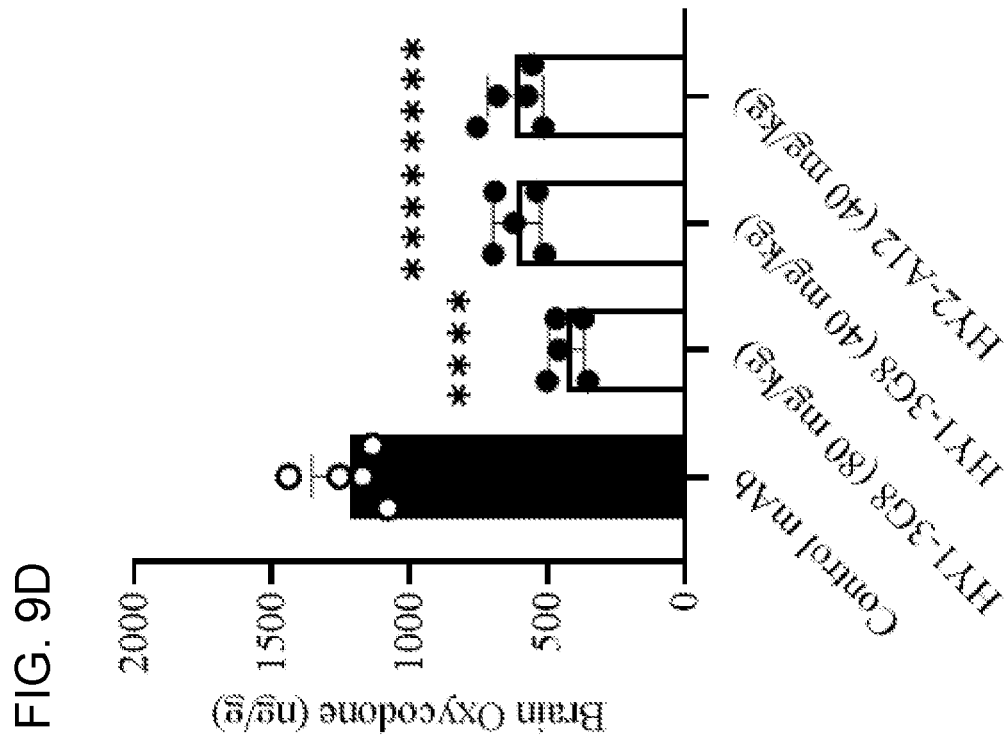
Figure 9C:
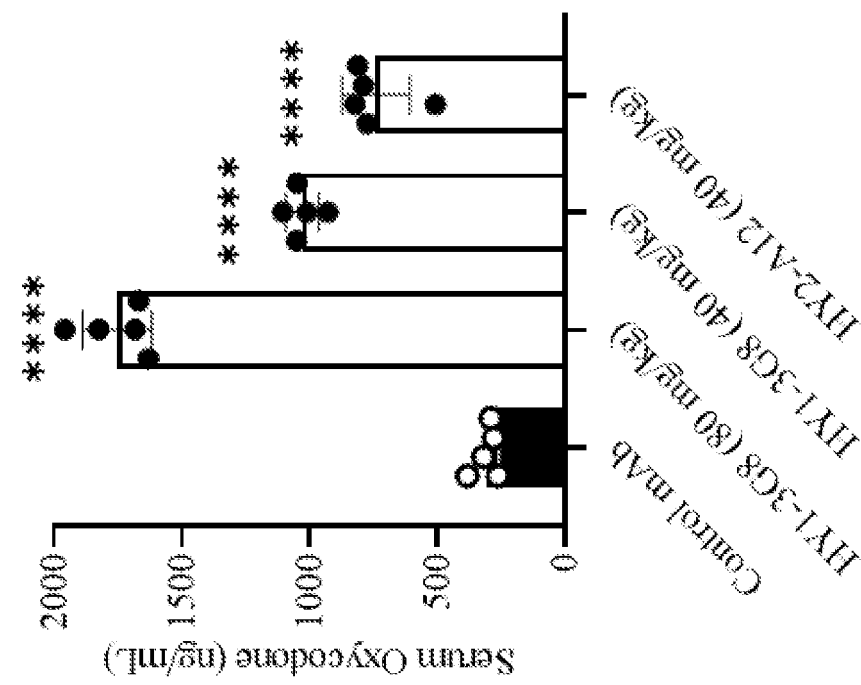

ELISA. FIG. 9B-FIG. 9D show passive immunization with anti-oxycodone mAb reduces oxycodone distribution to the brain. Mice (n=5/group) were passively immunized i.p. with 40 mg/kg or 80 mg/kg anti-oxycodone mAb i.p. After 24 hours, mice were challenged with 5.0 mg/kg oxycodone s.c., and antinociception was evaluated by latency to respond on a hot plate (FIG. 9B). Oxycodone levels in serum (FIG. 9C) and brain (FIG. 9D) were determined by GC-MS. Mean±SD; *p<0.05; ****p<0.0001.

Figure 10A:
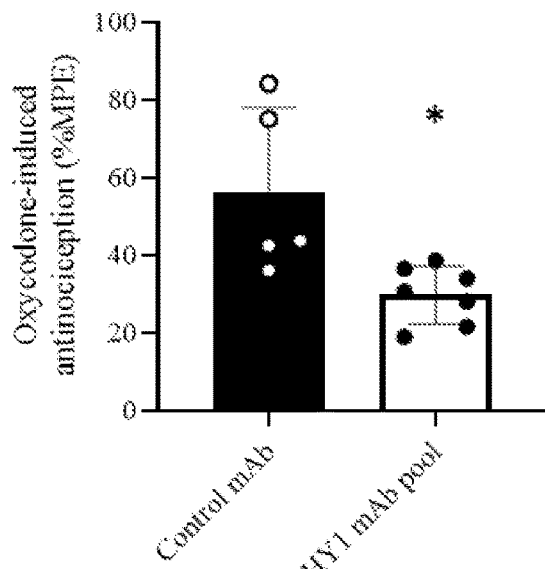
Figure 10D:
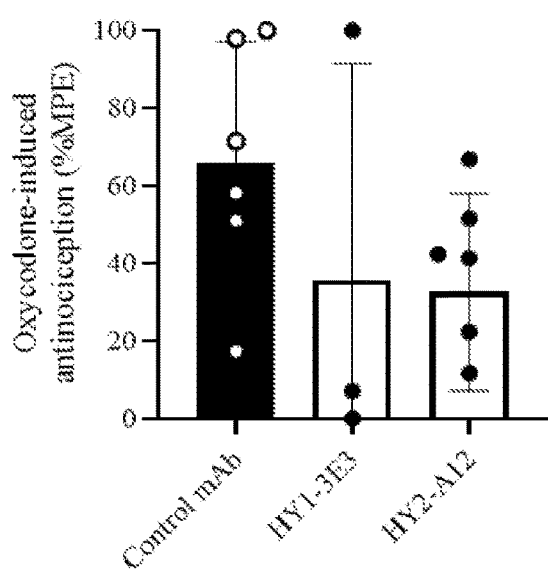
Figure 10B:
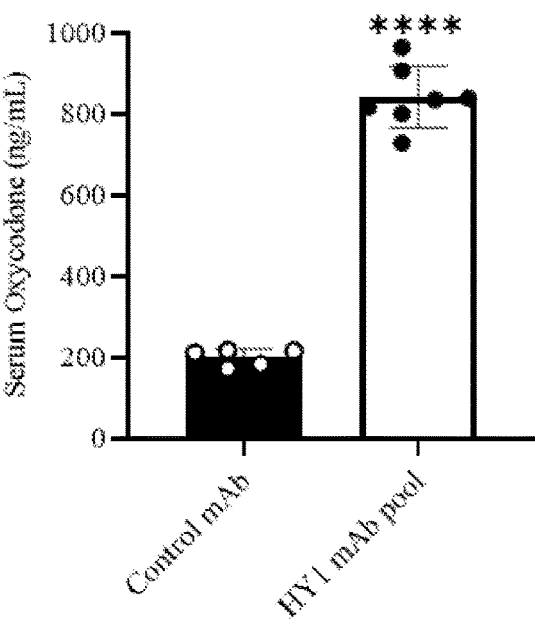
Figure 10E:
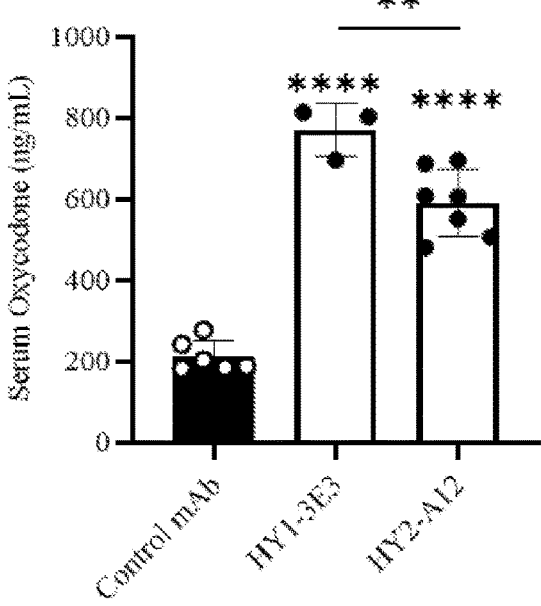

FIG. 10A-FIG. 10F show evidence of a-oxycodone mAb efficacy in vivo. Mice (n=3-7 per group) were passively immunized i.p. with control mAb or α-oxycodone mAb, and 24 hours later were challenged with 2.25 mg/kg oxycodone s.c. FIG. 10A-FIG. 10C, 40 mg/kg control mAb or combination of multiple HY1 a-oxycodone mAb; FIG. 10D-FIG. 10F, 40 mg/kg control mAb or α-oxycodone IgG$_1$ (HY1-3E3), or IgG$_{2a}$ (HY2-A12). Antinociception was first evaluated on a hot plate at t=30 min post-challenge (FIG. 10A, FIG. 10D). Effect of mAb on oxycodone concentration in serum (FIG. 10B, FIG. 10E) and brain (FIG. 10C, FIG. 10F). Mean±SD; p<0.01; *p<0.001; ****p<0.0001.

Figure 11A:
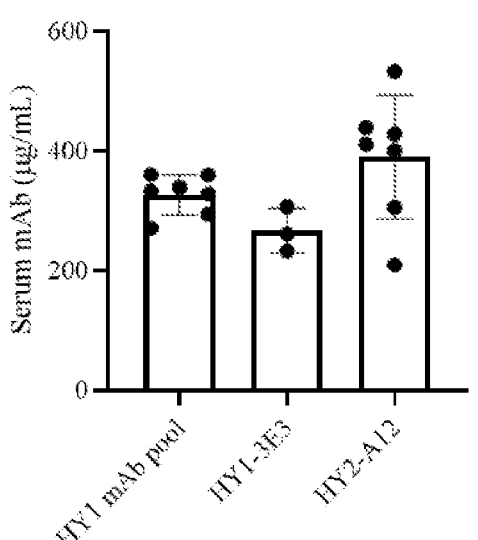
Figure 11B:
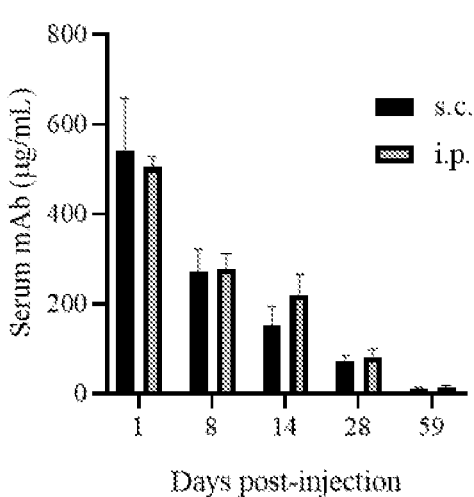
Figure 11C:
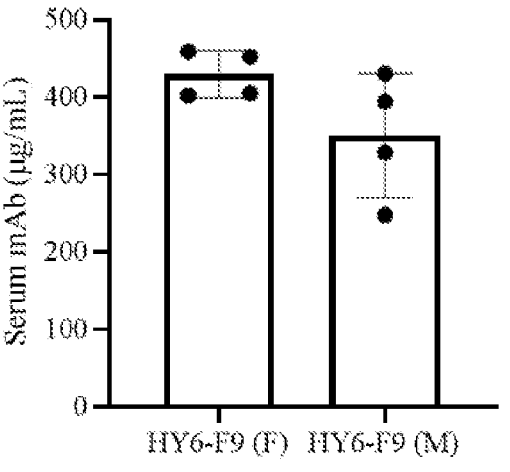
Figure 11D:
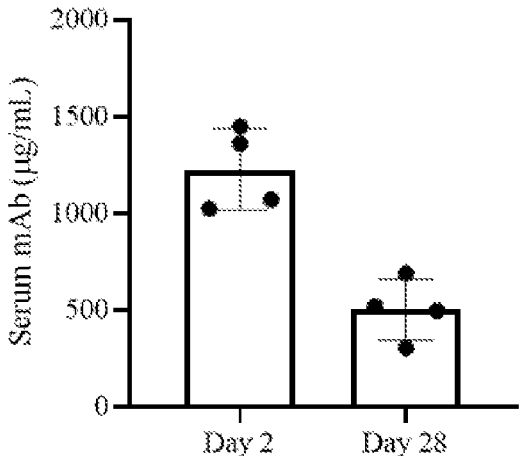

FIG. 11A-FIG. 11D shows serum levels of mAb in mice after passive immunization. Mice were passively immunized with a-opioid mAb, and serum concentrations post-immunization were evaluated by ELISA. Plates were coated with OXY-OVA, M-BSA or F-BSA, blocked with 1% gelatin, and incubated with serum serially diluted in PBS-T, and purified mAb as a standard to quantitate serum concentrations. FIG. 11A. a-oxycodone mAb 24 hours after passive immunization, 40 mg/kg i.p. FIG. 11B. a-heroin mAb 1-59 days after passive immunization, 40 mg/kg either s.c. or i.p. FIG. 11C. a-fentanyl mAb in female (F) or male (M) mice 24 hours after passive immunization, 40 mg/kg i.p. FIG. 11D. a-fentanyl mAb in rats 2-28 days after passive immunization with 60 mg/kg i.p. Bars represent mean±SD.

Figure 12A:
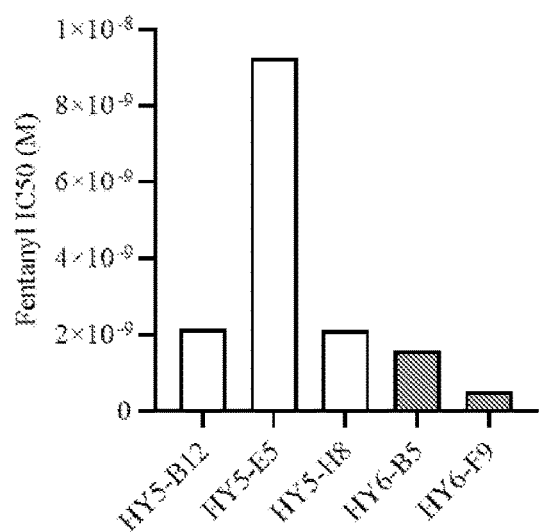
Figure 12B:
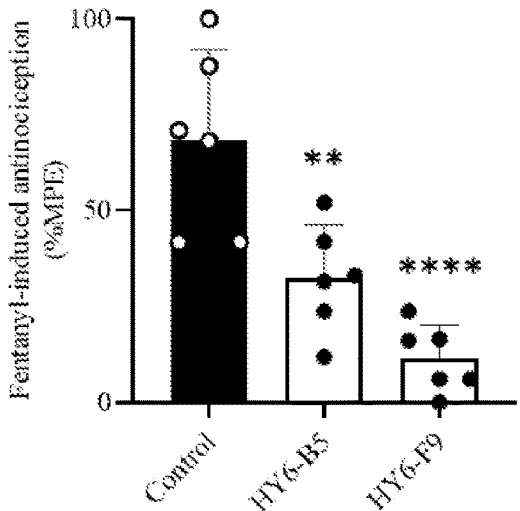
Figure 12C:
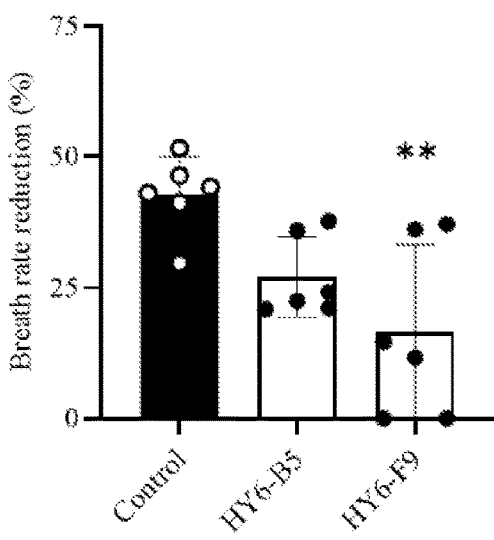
Figure 12D:
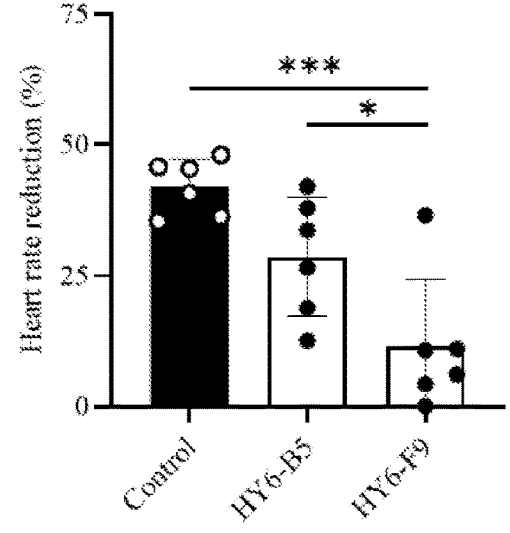

FIG. 12A-FIG. 12D show characterization and efficacy of anti-fentanyl mAb. FIG. 12A. Dissociation constants of anti-fentanyl mAb were determined by biolayer interferometry. FIG. 12B-FIG. 12D. Passive immunization with anti-fentanyl mAb reduces fentanyl-induced antinociception, respiratory depression and bradycardia. Mice (n=3 male and 3 female per group) were passively immunized with 40 mg/kg anti-fentanyl mAb i.p. After 24 hours, mice were challenged with 0.1 mg/kg heroin s.c., and antinociception was evaluated by latency to respond on a hot plate (FIG. 12B); breath rate (FIG. 12C) and heart rate (FIG. 12D) were measured by oximetry at 30 min post-injection. Mean±SD; p<0.01; *p<0.001; ****p<0.0001.

Figure 13A:
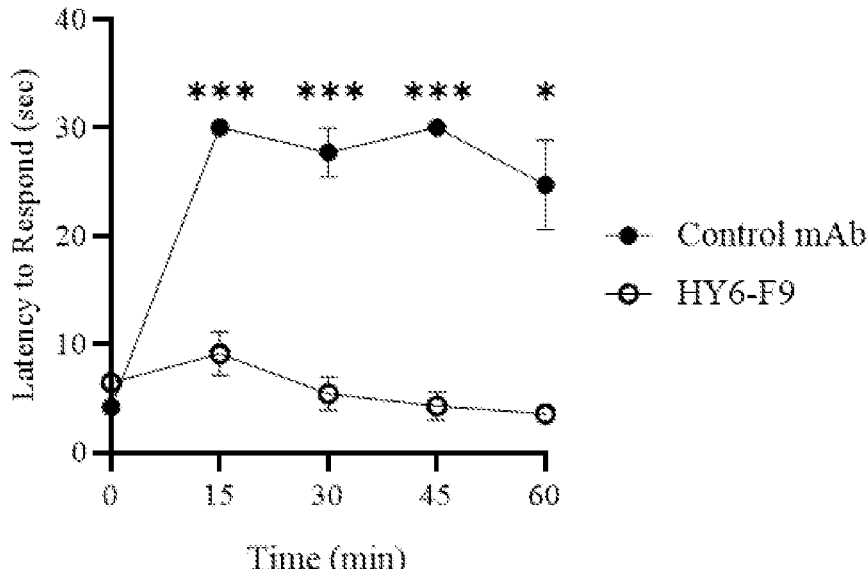
Figure 13B:
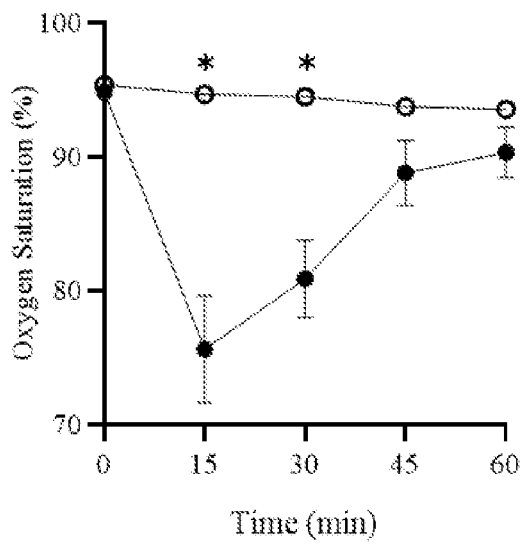
Figure 13C:
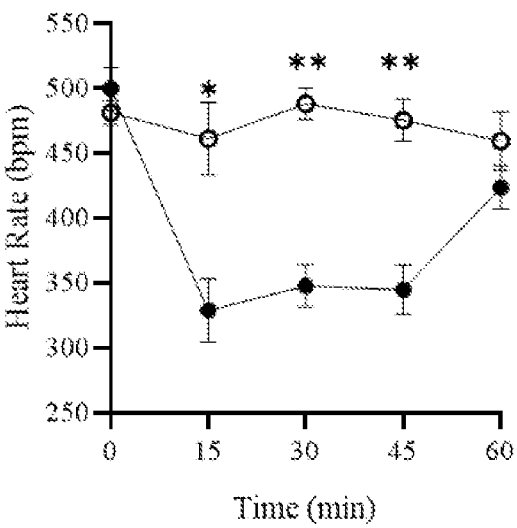

FIG. 13A-FIG. 13C show efficacy of anti-fentanyl mAb in rats. Rats (n=4/group) were passively immunized with 60 mg/kg anti-fentanyl mAb i.p. After 24 hours, rats were challenged with 0.1 mg/kg fentanyl s.c., and antinociception by latency to respond on a hot plate (FIG. 13A), oxygen saturation (FIG. 13B), and heart rate (FIG. 13C) were evaluated every 15 minutes up to 1 hour post-injection. Mean±SD; *p<0.05; p<0.01; *p<0.001.

DETAILED DESCRIPTION OF ILLUSTRATIVE EMBODIMENTS

This disclosure describes opioid-specific monoclonal antibodies (mAb) and antigen binding fragments thereof, methods of making those antibodies and antigen binding fragments thereof, and methods of using those antibodies and antigen binding fragment thereof including, for example, to treat opioid use disorder, to prevent opioid overdose, or to reverse opioid overdose.

In one aspect, further described below, this disclosure describes hybridomas expressing opioid-specific mAb generated by magnetic enrichment of opioid-specific B cells prior to fusion. Using this strategy, murine hybridomas expressing mAb specific for oxycodone, morphine, and fentanyl were identified. Passive immunization with purified oxycodone mAb was effective in reducing opioid distribution to the brain in mice.

As further described in Example 1, mAb of different IgG subclasses were compared for efficacy against oxycodone. Immunization with the OXY-KLH vaccine in combination with an anti-IL-4 mAb increased the likelihood of obtaining IgG2a and IgG3 mAb. Sequencing of opioid-specific mAb showed limited variability in antigen-binding regions.

High affinity opioid-specific antibodies block opioid distribution to the brain and reduce opioid-induced behavioral and toxic effects in mice and rats. Because of their selectivity, mAb do not interfere with endogenous opioid signaling and may be co-administered with an opioid agonist partial agonist, and/or antagonist such as methadone, buprenorphine, naltrexone, naloxone, nalmefene, etc.

Antibodies and Antigen Binding Fragments Thereof

In some aspects, this disclosure describes an antibody or an antigen binding fragment thereof that binds to an opioid. Such antibodies may be referred to herein as an anti-opioid antibody or an opioid-specific antibody. In some embodiments, the antibody or antigen binding fragment thereof binds to a naturally occurring opioid. In some embodiments, the antibody or antigen binding fragment thereof binds to a synthetic opioid. Exemplary opioids include, for example, heroin, a heroin metabolite, 6-acetylmorphine, morphine, fentanyl, a fentanyl analogue, oxycodone, oxymorphone, hydrocodone, etc.

In some embodiments, an antibody that binds to an opioid is a monoclonal antibody. In some embodiments, antibodies that bind to opioid include monoclonal antibodies produced by the hybridoma cell lines (also referred to herein as clones) listed in Table 1, Table 5, or Table 7 and/or by recombinant methods.

In some embodiments, the antigen binding fragments of a monoclonal antibody include antigen binding fragments of the monoclonal antibodies produced by the hybridoma cell lines (also referred to herein as clones) listed in Table 1, Table 5, or Table 7. In an exemplary embodiment, the antigen binding fragments include light and heavy chains of the monoclonal antibodies produced by a hybridoma cell line of Table 1, Table 5, or Table 7. In a further exemplary embodiment, the antigen binding fragments include the complementary determining regions (CDRs) of a monoclonal antibody produced by hybridoma cell lines of Table 1, Table 5, or Table 7. In another exemplary embodiment, as further described herein, the antigen binding fragments include CDRs having high homology to the complementary determining regions (CDRs) of a monoclonal antibody produced by hybridoma cell lines of Table 1, Table 5, or Table 7.

In some embodiments, an antigen binding fragment incudes a Fab fragment, a Fab' fragment, a F(ab)$_2$ fragment, and/or a Fv fragment.

In some embodiments, the antibody or antigen binding fragment thereof is an isolated antibody or antigen binding fragment thereof. In some embodiments, the antibodies or antigen binding fragments thereof may be isolated or purified by conventional immunoglobulin purification procedures, such as protein A- or G-Sepharose, hydroxyapatite chromatography, gel electrophoresis, dialysis, or affinity chromatography.

In some embodiments, an antibody or an antigen binding fragment thereof that binds to an opioid may include a derivative of an antibody that is modified or conjugated by the covalent attachment of any type of molecule to the antibody. Such antibody derivatives include, for example, antibodies or an antigen binding fragment thereof that have been modified by glycosylation, acetylation, pegylation, phosphorylation, amidation, polymerization, derivatization by known protecting/blocking groups, proteolytic cleavage, toxins, or linkage to a cellular ligand or other protein. Any of numerous chemical modifications may be carried out by known techniques, including, but not limited to, specific chemical cleavage, acetylation, formylation, and metabolic synthesis of tunicamycin. Additionally, the derivatives may contain one or more non-classical amino acids.

An antibody or an antigen binding fragment thereof that binds to an opioid may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, coenzymes, colored particles, biotin, or digoxigenin. A detectable marker often generates a measurable signal, such as radioactivity, fluorescent light, color, or enzyme activity. Antibodies or an antigen binding fragments thereof conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin;

examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such therapeutic moieties to antibodies are well-known.

In another aspect, this disclosure describes monoclonal antibodies and antigen binding fragments thereof produced by progeny or derivatives of these hybridoma cell lines, monoclonal antibodies or antigen binding fragments thereof produced by equivalent or similar hybridoma cell lines, and/or recombinant derivatives made thereof.

An intact antibody molecule has two heavy (H) chain variable regions (abbreviated herein as $V_H$) and two light (L) chain variable regions (abbreviated herein as $V_L$). The $V_H$ and $V_L$ regions can be further subdivided into regions of hypervariability, termed "complementarity determining regions" ("CDRs"), interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242, and Chothia et al. (1987) *J. Mol. Biol.* 196: 901-917). Each $V_H$ and $V_L$ is composed of three CDRs and four FRs, arranged from amino-terminus to carboxy-terminus in the following order: FR1, CDR1, FR2, CDR2, FR3, CDR3, FR4.

In some embodiments, a monoclonal antibody includes a monoclonal antibody having the same heavy chain as a monoclonal antibody produced by at least one of the clones of Table 1. In some embodiments, a monoclonal antibody includes a monoclonal antibody having the same light chain as a monoclonal antibody produced by at least one of the clones of Table 1. In some embodiments, a monoclonal antibody includes a monoclonal antibody having the same heavy chain and the same light chain as a monoclonal antibody produced by at least one of the clones of Table 1. In some embodiments, a monoclonal antibody may contain one, two, three, four, five, six, or more amino acid substitutions in the heavy and/or the light chains identified above wherein the amino acid substitutions do not substantially affect selective binding of the antibody to a target opioid. In some embodiments, the target opioid for a monoclonal antibody produced by at least one of the clones of Table 1 includes oxycodone, hydrocodone, an oxycodone derivative, a hydrocodone derivative, an oxycodone metabolite, or a hydrocodone metabolite.

In some embodiments, a monoclonal antibody or antigen binding fragment thereof includes a monoclonal antibody or antigen binding fragment thereof having the same $V_H$ domain as a monoclonal antibody produced by at least one of the clones of Table 1. In some embodiments, a monoclonal antibody or antigen binding fragment thereof includes a monoclonal antibody or antigen binding fragment thereof having the same $V_L$ domain as a monoclonal antibody produced by at least one of the clones of Table 1. In some embodiments, a monoclonal antibody or antigen binding fragment thereof includes a monoclonal antibody or antigen binding fragment thereof having the same $V_H$ domain and the same $V_L$ domain as a monoclonal antibody produced by at least one of the clones of Table 1. In some embodiments, a monoclonal antibody or antigen binding fragment thereof may contain one, two, three, four, five, six, or more amino acid substitutions in the $V_H$ domains and/or the $V_L$ domains identified above which do not substantially affect selective binding of the antibody or antigen binding fragment thereof to a target opioid.

In some embodiments, a monoclonal antibody or antigen binding fragment thereof includes a monoclonal antibody or antigen binding fragment thereof having at least one CDR of the $V_H$ domain of a monoclonal antibody produced by at least one of the clones of Table 1. In some embodiments, a monoclonal antibody or antigen binding fragment thereof includes a monoclonal antibody or antigen binding fragment thereof having at least two CDRs of the $V_H$ domain of a monoclonal antibody produced by at least one of the clones of Table 1. In some embodiments, a monoclonal antibody or antigen binding fragment thereof includes a monoclonal antibody or antigen binding fragment thereof having at least three CDRs of the $V_H$ domain of a monoclonal antibody produced by at least one of the clones of Table 1. Exemplary CDRs of the $V_H$ domains of monoclonal antibodies produced by the clones of Table 1 are shown in Table 2A.

In an exemplary embodiment, a monoclonal antibody or antigen binding fragment thereof includes FDFSRYWMS (SEQ ID NO: 1) as heavy chain CDR1, WIGEINPDSSTINY (SEQ ID NO: 2) as heavy chain CDR2, and/or SRVLLYYGSNPHWHFDV (SEQ ID NO: 3) as heavy chain CDR3 (the heavy chain CDRs of HY1-3G8).

In a further exemplary embodiment, a monoclonal antibody or antigen binding fragment thereof may include a heavy chain CDR1 sequence which differs by one or two amino acids from FDFSRYWMS (SEQ ID NO: 1), a heavy chain CDR2 sequence which differs by one or two amino acids from WIGEINPDSSTINY (SEQ ID NO: 2), and/or a heavy chain CDR3 sequence which differs by one or two amino acids from SRVLLYYGSNPHWHFDV (SEQ ID NO: 3).

In another exemplary embodiment, a monoclonal antibody or antigen binding fragment thereof includes FDFSRYWMS (SEQ ID NO: 1) as heavy chain CDR1, WIGEINPDSSTINY (SEQ ID NO: 2) or WIGEVNPDSSTINS (SEQ ID NO: 47) as heavy chain CDR2, and/or SRVLLYYGSNPHWHFDV (SEQ ID NO: 3) or ARLYYNYVDYYYAMDY (SEQ ID NO: 51).

In another exemplary embodiment, a monoclonal antibody or antigen binding fragment thereof may include a heavy chain CDR1 sequence which differs by one or two amino acids from FDFSRYWMS (SEQ ID NO: 1), a heavy chain CDR2 sequence which differs by one or two amino acids from WIGEINPDSSTINY (SEQ ID NO: 2) or from WIGEVNPDSSTINS (SEQ ID NO: 47), and/or a heavy chain CDR3 sequence which differs by one or two amino acids from SRVLLYYGSNPHWHFDV (SEQ ID NO: 3) or from ARLYYNYVDYYYAMDY (SEQ ID NO: 51).

In another exemplary embodiment, a monoclonal antibody or antigen binding fragment thereof includes GYTSTDYYIN (SEQ ID NO: 4) as heavy chain CDR1, WIGEIYPGSGNTYY (SEQ ID NO: 5) as heavy chain CDR2, and/or TRGGVYYGYDDAWFVY (SEQ ID NO: 6) as heavy chain CDR3 (the heavy chain CDRs of HY1-A12).

In a further exemplary embodiment, a monoclonal antibody or antigen binding fragment thereof may include a heavy chain CDR1 sequence which differs by one or two amino acids from GYTSTDYYIN (SEQ ID NO: 4), a heavy chain CDR2 sequence which differs by one or two amino acids from WIGEIYPGSGNTYY (SEQ ID NO: 5), and/or a heavy chain CDR3 sequence which differs by one or two amino acids from TRGGVYYGYDDAWFVY (SEQ ID NO: 6).

In yet another exemplary embodiment, a monoclonal antibody or antigen binding fragment thereof includes DHTFTDYYIN (SEQ ID NO: 29) as heavy chain CDR1, WIGEIYPGSGYTYY (SEQ ID NO: 36) as heavy chain CDR2, and/or ARGDGYYFWFGY (SEQ ID NO: 45) as heavy chain CDR3.

In a further exemplary embodiment, a monoclonal antibody or antigen binding fragment thereof may include a heavy chain CDR1 sequence which differs by one or two amino acids from DHTFTDYYIN (SEQ ID NO: 29), a heavy chain CDR2 sequence which differs by one or two amino acids from WIGEIYPGSGYTYY (SEQ ID NO: 36), and/or a heavy chain CDR3 sequence which differs by one or two amino acids from ARGDGYYFWFGY (SEQ ID NO: 45).

In yet another exemplary embodiment, a monoclonal antibody or antigen binding fragment thereof includes DHTFTDYYIN (SEQ ID NO: 29) as heavy chain CDR1, WIGEIYPGSGYTYY (SEQ ID NO: 36) as heavy chain CDR2, and/or ARGDGYYFWFGY (SEQ ID NO: 45) as heavy chain CDR3.

In a further exemplary embodiment, a monoclonal antibody or antigen binding fragment thereof may include a heavy chain CDR1 sequence which differs by one or two amino acids from YTFSNYWIE (SEQ ID NO: 30), a heavy chain CDR2 sequence which differs by one or two amino acids from WIGEILPGSGSTYH (SEQ ID NO: 37), and/or a heavy chain CDR3 sequence which differs by one or two amino acids from ATGSRLAWFVY (SEQ ID NO: 46).

In yet another exemplary embodiment, a monoclonal antibody or antigen binding fragment thereof includes DHTFTDYYIN (SEQ ID NO: 29) as heavy chain CDR1, WIGEIYPGSGYTYY (SEQ ID NO: 36) as heavy chain CDR2, and/or ARGDGYYFWFGY (SEQ ID NO: 45) as heavy chain CDR3.

In a further exemplary embodiment, a monoclonal antibody or antigen binding fragment thereof may include a heavy chain CDR1 sequence which differs by one or two amino acids from YTFTSQWMQ (SEQ ID NO: 23), a heavy chain CDR2 sequence which differs by one or two amino acids from WIGEINPSSGRTHY (SEQ ID NO: 38), and/or a heavy chain CDR3 sequence which differs by one or two amino acids from ARGDGDYVWFAY (SEQ ID NO: 47).

In yet another exemplary embodiment, a monoclonal antibody or antigen binding fragment thereof includes ATQSRSYWIE (SEQ ID NO: 31) or YTISSYWIE (SEQ ID NO: 32) as heavy chain CDR1, WIGEILPGSGSTTY (SEQ ID NO: 39) as heavy chain CDR2, and/or ARARTGTNYYTMDY (SEQ ID NO: 48) as heavy chain CDR3.

In a further exemplary embodiment, a monoclonal antibody or antigen binding fragment thereof may include a heavy chain CDR1 sequence which differs by one or two amino acids from ATQSRSYWIE (SEQ ID NO: 31) or from YTISSYWIE (SEQ ID NO: 32), a heavy chain CDR2 sequence which differs by one or two amino acids from WIGEILPGSGSTTY (SEQ ID NO: 39), and/or a heavy chain CDR3 sequence which differs by one or two amino acids from ARARTGTNYYTMDY (SEQ ID NO: 48).

Additionally or alternatively, in some embodiments, a monoclonal antibody or antigen binding fragment thereof includes a monoclonal antibody or antigen binding fragment thereof having at least one CDR of the $V_L$ domain of a monoclonal antibody produced by at least one of the clones of Table 1. In some embodiments, a monoclonal antibody or antigen binding fragment thereof includes a monoclonal antibody or antigen binding fragment thereof having at least two CDRs of the $V_L$ domain of a monoclonal antibody produced by at least one of the clones of Table 1. In some embodiments, a monoclonal antibody or antigen binding fragment thereof includes a monoclonal antibody or antigen binding fragment thereof having at least three CDRs of the $V_L$ domain of a monoclonal antibody produced by at least one of the clones of Table 1. Exemplary CDRs of the $V_L$ domains of monoclonal antibodies produced by the clones of Table 1 are shown in Table 2B. In some embodiments, the monoclonal antibody or antigen binding fragment thereof may include the $V_L$ domain of a monoclonal antibody produced by a clone of Table 1, and the corresponding $V_H$ domain of a monoclonal antibody produced by the same clone.

In an exemplary embodiment, a monoclonal antibody or antigen binding fragment thereof includes YRASKSVST-SGYSYMH (SEQ ID NO: 7) as light chain CDR1, LLI- YAASNLES (SEQ ID NO: 8) as light chain CDR2, and QHIRELT (SEQ ID NO: 9 as light chain CDR3 (the light chain CDRs of HY1-3G8).

In a further exemplary embodiment, a monoclonal antibody or antigen binding fragment thereof may include a light chain CDR1 sequence which differs by one or two amino acids from YRASKSVSTSGYSYMH (SEQ ID NO: 7), a light chain CDR2 sequence which differs by one or two amino acids from LLIYAASNLES (SEQ ID NO: 8), and/or a light chain CDR3 sequence which differs by one or two amino acids from QHIRELT (SEQ ID NO: 9).

In another exemplary embodiment, a monoclonal antibody or antigen binding fragment thereof includes YRASKSVSTSGYSYMH (SEQ ID NO: 7) as light chain CDR1, LLIYLVSNLES (SEQ ID NO: 10) as light chain CDR2, and QHIRELTR (SEQ ID NO: 11) as light chain CDR3.

In yet another exemplary embodiment, a monoclonal antibody or antigen binding fragment thereof may include a light chain CDR1 sequence which differs by one or two amino acids from YRASKSVSTSGYSYMH (SEQ ID NO: 7), a light chain CDR2 sequence which differs by one or two amino acids from LLIYLVSNLES (SEQ ID NO: 10), and/or a light chain CDR3 sequence which differs by one or two amino acids from QHIRELTR (SEQ ID NO: 11).

In another exemplary embodiment, a monoclonal antibody or antigen binding fragment thereof includes YRASKSVSTSGYSYMH (SEQ ID NO: 7) as light chain CDR1; LLIYLVSNLES (SEQ ID NO: 10) as light chain CDR2; and HHIRELTR (SEQ ID NO: 59), HRSLGSLR (SEQ ID NO: 60), or HHIRELTS (SEQ ID NO: 61) as light chain CDR3.

In yet another exemplary embodiment, a monoclonal antibody or antigen binding fragment thereof may include a light chain CDR1 sequence which differs by one or two amino acids from YRASKSVSTSGYSYMH (SEQ ID NO: 7), a light chain CDR2 sequence which differs by one or two amino acids from LLIYLVSNLES (SEQ ID NO: 10), and/or a light chain CDR3 sequence which differs by one or two amino acids from HHIRELTR (SEQ ID NO: 59), from HRSLGSLR (SEQ ID NO: 60), or from HHIRELTS (SEQ ID NO: 61).

In some embodiments, a monoclonal antibody or antigen binding fragment thereof may contain one, two, three, four, five, six, or more amino acid substitutions in one or more CDRs identified above which do not substantially affect selective binding of the antibody or antigen binding fragment thereof to a target opioid.

In some embodiments, a monoclonal antibody or antigen binding fragment thereof may contain one, two, three, four, five, six, or more amino acid substitutions in one or more framework regions (FRs). In some embodiments, the substitutions or substitutions in the framework regions (FRs) do not substantially affect selective binding of the antibody or antigen binding fragment thereof to a target opioid.

In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least one CDR of a $V_H$ domain of an antibody produced by one of the clones of Table 1. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least two CDRs of a $V_H$ domain of an antibody produced by one of the clones of Table 1. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least three CDRs of a $V_H$ domain of an antibody produced by one of the clones of Table 1.

In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least one CDR of a $V_L$ domain of an antibody produced by one of the clones of Table 1. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least two CDRs of a $V_L$ domain of an antibody produced by one of the clones of Table 1. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least three CDRs of a $V_L$ domain of an antibody produced by one of the clones of Table 1. In some embodiments, the monoclonal antibody or antigen binding fragment thereof may include one, two, or three of the CDRs of the $V_L$ domain of a monoclonal antibody produced by a clone of Table 1, and one, two, or three of the CDRs of the corresponding $V_H$ domain of a monoclonal antibody produced by the same clone. In some embodiments, the monoclonal antibody or antigen binding fragment thereof may include the CDRs of the $V_L$ domain of a monoclonal antibody produced by a clone of Table 1 or CDRs that differ by one or two amino acids from the CDRs of the $V_L$ domain of a monoclonal antibody produced by a clone of Table 1 and/or the CDRs of the corresponding $V_H$ domain of a monoclonal antibody produced by the same clone or CDRs that differ by one or two amino acids from the CDRs of the corresponding $V_H$ domain of a monoclonal antibody produced by the same clone.

In some embodiments, an anti-opioid antibody or antigen binding fragment thereof includes an antibody or antigen binding fragment thereof that binds to the same epitope as an antibody or antigen binding fragment thereof produced by one of the clones of Table 1.

In some embodiments, an antibody or antigen binding fragment thereof may contain one, two, three, four, five, six, or more amino acid substitutions relative to an antibody produced by one of the clones of Table 1, wherein the substitutions do not substantially affect selective binding of the antibody or antigen binding fragment thereof to a target opioid and/or the function of the antibody or antigen binding fragment thereof against a target opioid.

In some embodiments, a monoclonal antibody includes a monoclonal antibody having the same heavy chain as a monoclonal antibody produced by at least one of the clones of Table 5. In some embodiments, a monoclonal antibody includes a monoclonal antibody having the same light chain as a monoclonal antibody produced by at least one of the clones of Table 5. In some embodiments, a monoclonal antibody includes a monoclonal antibody having the same heavy chain and the same light chain as a monoclonal antibody produced by at least one of the clones of Table 5. In some embodiments, a monoclonal antibody may contain one, two, three, four, five, six, or more amino acid substitutions in the heavy and/or the light chains identified above wherein the amino acid substitutions do not substantially affect selective binding of the antibody to a target opioid. In some embodiments, the target opioid for a monoclonal antibody produced by at least one of the clones of Table 5 includes heroin; a heroin metabolite including, for example, morphine; or a heroin derivative, including, for example, a morphine derivative.

In some embodiments, a monoclonal antibody or antigen binding fragment thereof includes a monoclonal antibody or antigen binding fragment thereof having the same $V_H$ domain as a monoclonal antibody produced by at least one of the clones of Table 5. In some embodiments, a monoclonal antibody or antigen binding fragment thereof includes a monoclonal antibody or antigen binding fragment thereof having the same $V_L$ domain as a monoclonal antibody produced by at least one of the clones of Table 5. In some embodiments, a monoclonal antibody or antigen binding fragment thereof includes a monoclonal antibody or antigen binding fragment thereof having the same $V_H$ domain and the same $V_L$ domain as a monoclonal antibody produced by at least one of the clones of Table 5. In some embodiments, a monoclonal antibody or antigen binding fragment thereof may contain one, two, three, four, five, six, or more amino acid substitutions in the $V_H$ domains and/or the $V_L$ domains identified above which do not substantially affect selective binding of the antibody or antigen binding fragment thereof to a target opioid.

In some embodiments, a monoclonal antibody or antigen binding fragment thereof includes a monoclonal antibody or antigen binding fragment thereof having at least one CDR of the $V_H$ domain of a monoclonal antibody produced by at least one of the clones of Table 5. In some embodiments, a monoclonal antibody or antigen binding fragment thereof includes a monoclonal antibody or antigen binding fragment thereof having at least two CDRs of the $V_H$ domain of a monoclonal antibody produced by at least one of the clones of Table 5. In some embodiments, a monoclonal antibody or antigen binding fragment thereof includes a monoclonal antibody or antigen binding fragment thereof having at least three CDRs of the $V_H$ domain of a monoclonal antibody produced by at least one of the clones of Table 5. Exemplary CDRs of the $V_H$ domains of monoclonal antibodies produced by the clones of Table 5 are shown in Table 6A.

In an exemplary embodiment, a monoclonal antibody or antigen binding fragment thereof includes FNIKDYYIH (SEQ ID NO: 12) as heavy chain CDR1, WIGWIDPENGDTEYD (SEQ ID NO: 13) as heavy chain CDR2, and/or SSTMITTALFAY (SEQ ID NO: 14) as heavy chain CDR3 (the heavy chain CDRs of HY3-1G4).

In a further exemplary embodiment, a monoclonal antibody or antigen binding fragment thereof may include a heavy chain CDR1 sequence which differs by one or two amino acids from FNIKDYYIH (SEQ ID NO: 12), a heavy chain CDR2 sequence which differs by one or two amino acids from WIGWIDPENGDTEYD (SEQ ID NO: 13), and/or a heavy chain CDR3 sequence which differs by one or two amino acids from SSTMITTALFAY (SEQ ID NO: 14).

In another exemplary embodiment, a monoclonal antibody or antigen binding fragment thereof includes YKFSSYWID (SEQ ID NO: 15) as heavy chain CDR1, WIGEILPGSSSSYY (SEQ ID NO: 16) as heavy chain CDR2, and/or RWDTYYWYFDV (SEQ ID NO: 17) as heavy chain CDR3.

In yet another exemplary embodiment, a monoclonal antibody or antigen binding fragment thereof may include a heavy chain CDR1 sequence which differs by one or two amino acids from YKFSSYWID (SEQ ID NO: 15), a heavy chain CDR2 sequence which differs by one or two amino acids from WIGEILPGSSSSYY (SEQ ID NO: 16), and/or a heavy chain CDR3 sequence which differs by one or two amino acids from RWDTYYWYFDV (SEQ ID NO: 17).

Additionally or alternatively, in some embodiments, a monoclonal antibody or antigen binding fragment thereof includes a monoclonal antibody or antigen binding fragment thereof having at least one CDR of the $V_L$ domain of a monoclonal antibody produced by at least one of the clones of Table 5. In some embodiments, a monoclonal antibody or antigen binding fragment thereof includes a monoclonal antibody or antigen binding fragment thereof having at least two CDRs of the $V_L$ domain of a monoclonal antibody produced by at least one of the clones of Table 5. In some embodiments, a monoclonal antibody or antigen binding fragment thereof includes a monoclonal antibody or antigen binding fragment thereof having at least three CDRs of the $V_L$ domain of a monoclonal antibody produced by at least one of the clones of Table 5. Exemplary CDRs of the $V_L$ domains of monoclonal antibodies produced by the clones of Table 5 are shown in Table 6B. In some embodiments, the monoclonal antibody or antigen binding fragment thereof may include the $V_L$ domain of a monoclonal antibody produced by a clone of Table 5, and the corresponding $V_H$ domain of a monoclonal antibody produced by the same clone.

In an exemplary embodiment, a monoclonal antibody or antigen binding fragment thereof includes CKASHSVDYDGDRYMN (SEQ ID NO: 18) as light chain CDR1, LLIYVASNLEC (SEQ ID NO: 19) as light chain CDR2 and QRSNEDPF (SEQ ID NO: 20) as light chain CDR3.

In a further exemplary embodiment, a monoclonal antibody or antigen binding fragment thereof may include a light chain CDR1 sequence which differs by one or two amino acids from CKASHSVDYDGDRYMN (SEQ ID NO: 18), a light chain CDR2 sequence which differs by one or two amino acids from LLIYVASNLEC (SEQ ID NO: 19), and/or a light chain CDR3 sequence which differs by one or two amino acids from QRSNEDPF (SEQ ID NO: 20).

In another exemplary embodiment, a monoclonal antibody or antigen binding fragment thereof includes CRASQSIGTSTH (SEQ ID NO: 21) as light chain CDR1, IIIYFVSNLEF (SEQ ID NO: 22) as light chain CDR2, and QHIRELTR (SEQ ID NO: 11) or QHIREITR (SEQ ID NO: 98) as light chain CDR3.

In yet another exemplary embodiment, a monoclonal antibody or antigen binding fragment thereof may include a light chain CDR1 sequence which differs by one or two amino acids from CRASQSIGTSTH (SEQ ID NO: 21), a light chain CDR2 sequence which differs by one or two amino acids from IIIYFVSNLEF (SEQ ID NO: 22) or from IIIYFESILEF (SEQ ID NO: 96), and/or a light chain CDR3 sequence which differs by one or two amino acids from QHIRELTR (SEQ ID NO: 11) or QHIREITR (SEQ ID NO: 98).

In another exemplary embodiment, a monoclonal antibody or antigen binding fragment thereof includes YRASKSVSTSGYSYMH (SEQ ID NO: 7) as light chain CDR1, LLIYLVSNLES (SEQ ID NO: 10) as light chain CDR2 and QHIRELTR (SEQ ID NO: 11) or SHIRELTR (SEQ ID NO: 97) as light chain CDR3.

In yet another exemplary embodiment, a monoclonal antibody or antigen binding fragment thereof may include a light chain CDR1 sequence which differs by one or two amino acids from YRASKSVSTSGYSYMH (SEQ ID NO: 7), a light chain CDR2 sequence which differs by one or two amino acids from LLIYLVSNLES (SEQ ID NO: 10), and/or a light chain CDR3 sequence which differs by one or two amino acids from QHIRELTR (SEQ ID NO: 11) or from SHIRELTR (SEQ ID NO: 97).

In some embodiments, a monoclonal antibody or antigen binding fragment thereof may contain one, two, three, four, five, six, or more amino acid substitutions in one or more CDRs identified above which do not substantially affect selective binding of the antibody or antigen binding fragment thereof to a target opioid.

In some embodiments, a monoclonal antibody or antigen binding fragment thereof may contain one, two, three, four, five, six, or more amino acid substitutions in one or more framework regions (FRs). In some embodiments, the substitutions or substitutions in the framework regions (FRs) do not substantially affect selective binding of the antibody or antigen binding fragment thereof to a target opioid.

In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least one CDR of a $V_H$ domain of an antibody produced by one of the clones of Table 5. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least two CDRs of a $V_H$ domain of an antibody produced by one of the clones of Table 5. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least three CDRs of a $V_H$ domain of an antibody produced by one of the clones of Table 5.

In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least one CDR of a $V_L$ domain of an antibody produced by one of the clones of Table 5. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least two CDRs of a $V_L$ domain of an antibody produced by one of the clones of Table 5. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least three CDRs of a $V_L$ domain of an antibody produced by one of the clones of Table 5. In some embodiments, the monoclonal antibody or antigen binding fragment thereof may include one, two, or three of the CDRs of the $V_L$ domain of a monoclonal antibody produced by a clone of Table 5, and one, two, or three of the CDRs of the corresponding $V_H$ domain of a monoclonal antibody produced by the same clone. In some embodiments, the monoclonal antibody or antigen binding fragment thereof may include the CDRs of the VL domain of a monoclonal antibody produced by a clone of Table 5 or CDRs that differ by one or two amino acids from the CDRs of the VL domain of a monoclonal antibody produced by a clone of Table 5 and/or the CDRs of the corresponding $V_H$ domain of a monoclonal antibody produced by the same clone or CDRs that differ by one or two amino acids from the CDRs of the corresponding $V_H$ domain of a monoclonal antibody produced by the same clone.

In some embodiments, an anti-opioid antibody or antigen binding fragment thereof includes an antibody or antigen binding fragment thereof that binds to the same epitope as an antibody or antigen binding fragment thereof produced by one of the clones of Table 5.

In some embodiments, an antibody or antigen binding fragment thereof may contain one, two, three, four, five, six, or more amino acid substitutions relative to an antibody produced by one of the clones of Table 5, wherein the substitutions do not substantially affect selective binding of the antibody or antigen binding fragment thereof to a target opioid and/or the function of the antibody or antigen binding fragment thereof against a target opioid.

In some embodiments, a monoclonal antibody includes a monoclonal antibody having the same heavy chain as a monoclonal antibody produced by at least one of the clones of Table 7. In some embodiments, a monoclonal antibody includes a monoclonal antibody having the same light chain as a monoclonal antibody produced by at least one of the clones of Table 7. In some embodiments, a monoclonal antibody includes a monoclonal antibody having the same heavy chain and the same light chain as a monoclonal antibody produced by at least one of the clones of Table 7. In some embodiments, a monoclonal antibody may contain one, two, three, four, five, six, or more amino acid substitutions in the heavy and/or the light chains identified above wherein the amino acid substitutions do not substantially affect selective binding of the antibody to a target opioid. In some embodiments, the target opioid for a monoclonal antibody produced by at least one of the clones of Table 7 includes fentanyl, a fentanyl analogue, a fentanyl derivative, or a fentanyl metabolite.

In some embodiments, a monoclonal antibody or antigen binding fragment thereof includes a monoclonal antibody or antigen binding fragment thereof having the same $V_H$ domain as a monoclonal antibody produced by at least one of the clones of Table 7. In some embodiments, a monoclonal antibody or antigen binding fragment thereof includes a monoclonal antibody or antigen binding fragment thereof having the same $V_L$ domain as a monoclonal antibody produced by at least one of the clones of Table 7. In some embodiments, a monoclonal antibody or antigen binding fragment thereof includes a monoclonal antibody or antigen binding fragment thereof having the same $V_H$ domain and the same $V_L$ domain as a monoclonal antibody produced by at least one of the clones of Table 7. In some embodiments, a monoclonal antibody or antigen binding fragment thereof may contain one, two, three, four, five, six, or more amino acid substitutions in the $V_H$ domains and/or the $V_L$ domains identified above which do not substantially affect selective binding of the antibody or antigen binding fragment thereof to a target opioid.

In some embodiments, a monoclonal antibody or antigen binding fragment thereof includes a monoclonal antibody or antigen binding fragment thereof having at least one CDR of the $V_H$ domain of a monoclonal antibody produced by at least one of the clones of Table 7. In some embodiments, a monoclonal antibody or antigen binding fragment thereof includes a monoclonal antibody or antigen binding fragment thereof having at least two CDRs of the $V_H$ domain of a monoclonal antibody produced by at least one of the clones of Table 7. In some embodiments, a monoclonal antibody or antigen binding fragment thereof includes a monoclonal antibody or antigen binding fragment thereof having at least three CDRs of the VH domain of a monoclonal antibody produced by at least one of the clones of Table 7. Exemplary CDRs of the $V_H$ domains of monoclonal antibodies produced by the clones of Table 7 are shown in Table 8A.

In an exemplary embodiment, a monoclonal antibody or antigen binding fragment thereof includes YTFTSQWMQ (SEQ ID NO: 23) as heavy chain CDR1, WIGEINPSSGR-THYN (SEQ ID NO: 24) as heavy chain CDR2, and/or RGDGDYVWFAY (SEQ ID NO: 25) as heavy chain CDR3 (the heavy chain CDRs of HY6-F9).

In a further exemplary embodiment, a monoclonal antibody or antigen binding fragment thereof may include a heavy chain CDR1 sequence which differs by one or two amino acids from YTFTSQWMQ (SEQ ID NO: 23), a heavy chain CDR2 sequence which differs by one or two amino acids from WIGEINPSSGRTHYN (SEQ ID NO: 24), and/or a heavy chain CDR3 sequence which differs by one or two amino acids from RGDGDYVWFAY (SEQ ID NO: 25).

In another exemplary embodiment, a monoclonal antibody or antigen binding fragment thereof includes YAFT-SYNIY (SEQ ID NO: 99) as heavy chain CDR1, WIGYIDPYNGGTTYN (SEQ ID NO: 100) as heavy chain CDR2, and/or SEIYYDYGGRFAY (SEQ ID NO: 102) as heavy chain CDR3 (the heavy chain CDRs of HY6-B5).

In a further exemplary embodiment, a monoclonal antibody or antigen binding fragment thereof may include a heavy chain CDR1 sequence which differs by one or two amino acids from YAFTSYNIY (SEQ ID NO: 99), a heavy chain CDR2 sequence which differs by one or two amino acids from WIGYIDPYNGGTTYN (SEQ ID NO: 100), and/or a heavy chain CDR3 sequence which differs by one or two amino acids from SEIYYDYGGRFAY (SEQ ID NO: 102).

Additionally or alternatively, in some embodiments, a monoclonal antibody or antigen binding fragment thereof includes a monoclonal antibody or antigen binding fragment thereof having at least one CDR of the $V_L$ domain of a monoclonal antibody produced by at least one of the clones of Table 7. In some embodiments, a monoclonal antibody or antigen binding fragment thereof includes a monoclonal antibody or antigen binding fragment thereof having at least two CDRs of the $V_L$ domain of a monoclonal antibody produced by at least one of the clones of Table 7. In some embodiments, a monoclonal antibody or antigen binding fragment thereof includes a monoclonal antibody or antigen binding fragment thereof having at least three CDRs of the $V_L$ domain of a monoclonal antibody produced by at least one of the clones of Table 7. Exemplary CDRs of the $V_L$ domains of monoclonal antibodies produced by the clones of Table 7 are shown in Table 8B. In some embodiments, the monoclonal antibody or antigen binding fragment thereof may include the $V_L$ domain of a monoclonal antibody produced by a clone of Table 7, and the corresponding $V_H$ domain of a monoclonal antibody produced by the same clone.

In an exemplary embodiment, a monoclonal antibody or antigen binding fragment thereof includes YRASKSVST-SGYSYMH (SEQ ID NO: 7) as light chain CDR1, LLIYL-VSNLES (SEQ ID NO: 10) as light chain CDR2 and/or QHIRELTR (SEQ ID NO: 11) as light chain CDR3 (the light chain CDRs of HY6-F9 and HY6-B5).

In a further exemplary embodiment, a monoclonal antibody or antigen binding fragment thereof may include a light chain CDR1 sequence which differs by one or two amino acids from YRASKSVSTSGYSYMH (SEQ ID NO: 7), a light chain CDR2 sequence which differs by one or two amino acids from LLIYLVSNLES (SEQ ID NO: 10), and/or a light chain CDR3 sequence which differs by one or two amino acids from QHIRELTR (SEQ ID NO: 11).

In some embodiments, a monoclonal antibody or antigen binding fragment thereof may contain one, two, three, four, five, six, or more amino acid substitutions in one or more CDRs identified above which do not substantially affect selective binding of the antibody or antigen binding fragment thereof to a target opioid.

In some embodiments, a monoclonal antibody or antigen binding fragment thereof may contain one, two, three, four, five, six, or more amino acid substitutions in one or more framework regions (FRs). In some embodiments, the substitutions or substitutions in the framework regions (FRs) do not substantially affect selective binding of the antibody or antigen binding fragment thereof to a target opioid.

In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least one CDR of a $V_H$ domain of an antibody produced by one of the clones of Table 7. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least two CDRs of a $V_H$ domain of an antibody produced by one of the clones of Table 7. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least three CDRs of a $V_H$ domain of an antibody produced by one of the clones of Table 7.

In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least one CDR of a $V_L$ domain of an antibody produced by one of the clones of Table 7. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least two CDRs of a $V_L$ domain of an antibody produced by one of the clones of Table 7. In some embodiments, a monoclonal antibody or antigen binding fragment thereof includes a monoclonal antibody or antigen binding fragment thereof having an amino acid sequence at least 70%, at least 80%, at least 85%, at least 90%, at least 95%, at least 96%, at least 97%, at least 98%, or at least 99% identical to an amino acid sequence of at least three CDRs of a $V_L$ domain of an antibody produced by one of the clones of Table 7. In some embodiments, the monoclonal antibody or antigen binding fragment thereof may include one, two, or three of the CDRs of the $V_L$ domain of a monoclonal antibody produced by a clone of Table 7, and one, two, or three of the CDRs of the corresponding $V_H$ domain of a monoclonal antibody produced by the same clone. In some embodiments, the monoclonal antibody or antigen binding fragment thereof may include the CDRs of the $V_L$ domain of a monoclonal antibody produced by a clone of Table 7 or CDRs that differ by one or two amino acids from the CDRs of the $V_L$ domain of a monoclonal antibody produced by a clone of Table 7 and/or the CDRs of the corresponding $V_H$ domain of a monoclonal antibody produced by the same clone or CDRs that differ by one or two amino acids from the CDRs of the corresponding $V_H$ domain of a monoclonal antibody produced by the same clone.

In some embodiments, an anti-opioid antibody or antigen binding fragment thereof includes an antibody or antigen binding fragment thereof that binds to the same epitope as an antibody produced by one of the clones of Table 7.

In some embodiments, an antibody or antigen binding fragment thereof may contain one, two, three, four, five, six, or more amino acid substitutions relative to an antibody produced by one of the clones of Table 7, wherein the substitutions do not substantially affect selective binding of the antibody or antigen binding fragment thereof to a target opioid and/or the function of the antibody or antigen binding fragment thereof against a target opioid.

The antibody or antigen binding fragment thereof may be an antibody from or derived from an antibody of any suitable species. In some embodiments, the antibody may be a mouse antibody. In some embodiments, the antibody may be a rat antibody. In some embodiments, the antibody may be a rabbit antibody. In some embodiments, the antibody may be a human antibody.

In some embodiments, the antibody is an IgG antibody. In some embodiments, the antibody may be an antibody or an IgG subclass including, for example, IgG1, IgG2, IgG3 or IgG4. In some embodiments, the antibody may be a mouse IgG of one of the following sub-classes: IgG1, IgG2A, IgG2B, IgG2C and IgG3. In some embodiments, the antibody may be a rat IgG of one of the following sub-classes: IgG1, IgG2A, IgG2B, or IgG2C.

In some embodiments, the antibody may include a kappa light chain. In some embodiments, the antibody may include a lambda light chain. A monoclonal antibody may be obtained by any suitable technique. In some embodiments, an antibody that binds to an opioid may be made by recombinant DNA methods, produced by phage display, and/or produced by combinatorial methods. DNA encoding an antibody that binds to an opioid may be readily isolated and sequenced using conventional procedures. In some embodiments, a hybridoma cell described herein may serve as a source of such DNA. In some embodiments, an opioid-specific B cell described herein may serve as a source of such DNA. Once isolated, the DNA may be transfected into a host cell (including, for example, simian COS cells, Chinese hamster ovary (CHO) cells, human embryonic kidney cells (HEK), or myeloma cells that do not otherwise produce immunoglobulin protein) or introduced into a host cell by genome editing (for example, using a CRISPR-Cas system) to obtain the synthesis of monoclonal antibodies in a recombinant host cells. The DNA encoding an antibody that binds to an opioid may be modified to, for example, humanize the antibody.

In some embodiments, a monoclonal antibody may be obtained by a method that includes administering a vaccine to a subject wherein the vaccine includes an opioid hapten conjugated to a carrier polypeptide; isolating antibody-producing cells from the subject (for example, B cells); and enriching the antibody-producing cells for cells that bind to the opioid hapten. In some embodiments, the opioid hapten may include, for example, heroin, a heroin metabolite, 6-acetylmorphine, morphine, fentanyl, a fentanyl analogue, oxycodone, oxymorphone, or hydrocodone, or a fragment thereof.

In some embodiments, the vaccine may be co-administered with a cytokine-signaling immunomodulator. As used herein, a "cytokine-signaling immunomodulator" refers to a compound that directly induces or inhibits cytokine signaling in contrast to, for example, an adjuvant (for example, alum, CpG, or imidoazoquinoline amines) that affect cytokine signaling only indirectly through another signaling pathway. A "cytokine-signaling immunomodulator" may be a biological compound, such as, for example, interleukin, an antibody against an interleukin, an antibody against an interleukin receptor, an interleukin/monoclonal antibody complex, or a peptide ligand for an interleukin receptor. In other cases, a "cytokine-signaling immunomodulator" may be a small molecule (for example, STAT or mTOR ligand) that directly induces or inhibits cytokine signaling. For instance, the anti-IL-4 mAb inhibits exogenous or endogenous IL-4 from binding to the IL-4 receptor may be a "cytokine-signaling immunomodulator". In certain embodiments, a "cytokine-signaling immunomodulator" may include a compound that targets the anti-IL-4 receptor (for example, a peptide, antibody, antibody fragment, or small molecule ligand). In some embodiments, the cytokine-signaling immunomodulator may include a cytokine neutralizing antibody.

In some embodiments, a subject's immune response to a vaccine co-administered with a cytokine-signaling immunomodulator increases production of IgG2a antibody subclass and/or IgG3 antibody subclass compared to the subject's immune response to the vaccine without the cytokine-signaling immunomodulator. For example, as described in Example 1, immunization with the OXY-KLH vaccine in combination with an anti-IL-4 mAb increased the likelihood of obtaining IgG2a and IgG3 mAb.

In some embodiments, the method may further include co-administering an adjuvant with the vaccine. Adjuvants may include, for example, alum, CpG, imidoazoquinoline amines, etc.

The carrier polypeptide may include, for example, keyhole limpet hemocyanin (KLH), subunit keyhole limpet hemocyanin (sKLH), bovine serum albumin (BSA), ovalbumin (OVA), CRM197, tetanus toxoid, diphtheria toxoid, meningococcal outer membrane protein complex (OMPC), *H. influenzae* protein D (HiD), etc. KLH may include native decamer KLH or subunit KLH (sKLH). sKLH may include a monomer or dimer KLH product. The carrier protein may be conjugated to the opioid hapten by any suitable mean. In some embodiments, the carrier protein may be conjugated to the opioid hapten by a tetraglycine linker (SEQ ID NO: 26).

In some embodiments, a monoclonal antibody may be obtained by a method that includes identifying a subject that has been exposed to an opioid; isolating antibody-producing cells from the subject; and enriching the antibody-producing cells for a cell or cells that bind to an opioid hapten. In some embodiments, such a method may further include exposing the subject to the opioid. In some embodiments, the opioid and/or the opioid hapten may include, for example, heroin, a heroin metabolite, 6-acetylmorphine, morphine, fentanyl, a fentanyl analogue, oxycodone, oxymorphone, or hydrocodone, or a fragment thereof.

In some embodiments, a method of obtaining a monoclonal antibody further includes sequencing a B cell receptor, cloning a B cell receptor, or both sequencing and cloning a B cell receptor of an antibody-producing cell that binds to an opioid hapten. In some embodiments, the method further includes expression of the B cell receptor in a vector.

In some embodiments, a method of obtaining a monoclonal antibody includes enriching the antibody-producing cells comprises antigen-based magnetic enrichment or flow cytometry, or both. In some embodiments, the subject is a human, a mouse, a rat, or a rabbit.

In some embodiments, the antibody may be a humanized antibody. An antibody that binds to an opioid may be humanized by any suitable method. Techniques for producing humanized monoclonal antibodies may be found, for example, in Jones et al. (1986) Nature 321:522 and Singer et al. (1993) J. Immunol. 150:2844. For example, humanization of the antibody may include changes to the antibody to reduce the immunogenicity of the antibody when used in humans. In some embodiments, a humanized antibody that binds to an opioid may include at least a portion of an immunoglobulin constant region (Fc) of a human immunoglobulin. A humanized antibody that binds to an opioid may include, in some embodiments, a human immunoglobulin (recipient antibody) in which residues from one or more complementary determining regions (CDRs) of the recipient antibody are replaced by residues from one or more CDRs of a non-human species antibody (donor antibody), such as mouse, rat, or rabbit antibody, that binds to an opioid. In some embodiments, Fv framework residues of a human immunoglobulin may be replaced by corresponding non-human residues from an antibody that binds to an opioid.

In some embodiments, a monoclonal antibody includes a chimeric antibody, that is, an antibody in which different portions are derived from different animal species. A chimeric antibody may be obtained by, for example, splicing the genes from a mouse antibody molecule with appropriate antigen specificity together with genes from a human antibody molecule of appropriate biological specificity. See, for example, Takeda et al. (1985) Nature 314:544.

In some embodiments, an antibody includes a bispecific or a bifunctional antibody. A bispecific or bifunctional antibody is an artificial hybrid antibody having two different heavy/light chain pairs and two different binding sites. A bispecific antibody may be produced by a variety of methods including fusion of hybridomas or linking of F(ab') fragments. See, for example, Songsivilai and Lachmann (1990) Clin. Exp. Immunol. 79:315; Kostelny et al. (1992) J. Immunol. 148:1547. In addition, bispecific antibodies may be formed as "diabodies" (Holliger et al. (1993) PNAS USA 90:6444) or "Janusins" (Traunecker et al. (1991) EMBO J. 10:3655; Traunecker et al. (1992) Int. J Cancer Suppl. 7:51).

In some embodiments, an antibody that binds to an opioid or an antigen binding fragment thereof may be expressed through a viral (for example, AAV) vector system suitable for injection into a human or mammal and expression of the antibody or antigen binding fragment thereof.

In some embodiments, an antibody may be produced by an animal (including, but not limited to, human, mouse, rat, rabbit, hamster, goat, horse, chicken, or turkey), produced by a cell from an animal, chemically synthesized, or recombinantly expressed. The antibody may be purified by any method known in the art for purification of an immunoglobulin molecule, for example, by chromatography (for example, ion exchange, affinity, or size exclusion chromatography), centrifugation, differential solubility, or by any other standard technique for the purification of proteins. In addition, an antibody may be fused to a heterologous polypeptide sequence, as described herein or otherwise known in the art, including, for example, to facilitate purification.

A monoclonal antibody may be assayed for immunospecific binding by the methods described herein and by any suitable method known in the art. The immunoassay that may be used includes but is not limited to a competitive and/or a non-competitive assay system using a technique such as BIACORE analysis, fluorescence activated cell sorter (FACS) analysis, immunofluorescence, immunocytochemistry, Western blot, radio-immunoassay, enzyme linked immunosorbent assay (ELISA), "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see for example, Ausubel et al., eds, Current Protocols in Molecular Biology, Vol. 1, John Wiley & Sons, Inc., N.Y. (1994)).

In some embodiments, an antibody that binds to an opioid includes an antibody that abrogates binding of an opioid to an opioid ligand. An opioid ligand may include an opioid receptor. In some embodiments, an opioid ligand may include more than one opioid receptor. Opioid receptors may include, for example, a μ opioid receptor (MOR), a κ Opioid receptor (KOR), a δ opioid receptor (DOR), or an opioid receptor like-1 (also called a nociceptin or orphanin FQ) receptor. In some embodiments, the antibody may decrease the binding of an opioid to an opioid ligand (including, for example, an opioid receptor) by at least 10 percent (%), at least 15%, at least 20%, at least 25%, at least 30%, at least 40%, at least 50%, at least 60%, at least 70%, at least 80%, at least 90%, at least 95%, or at least 98%. In some embodiments, the antibody may decrease the binding of an opioid to an opioid receptor by up to 20%, up to 25%, up to 30%, up to 40%, up to 50%, up to 60%, up to 70%, up to 80%, up to 90%, up to 95%, up to 98%, or up to 99%.

In some embodiments, an antibody that binds to an opioid includes an antibody that sequesters the target opioid in serum. Sequestration of an opioid drug in serum may prevent drug distribution to the brain, drug-induced pharmacological effects, drug-induced behavioral effects, and/or drug-induced toxicity (such as opioid-induced respiratory depression or bradycardia). In some embodiments, when passive administered to a subject, the antibody may sequester at least 10 percent (%), at least 15%, at least 20%, at least 25%, at least 30%, at least 40%, at least 50%, at least 60%, at least 70%, at least 80%, at least 90%, at least 95%, or at least 98% of an opioid in the subject's serum.

In some embodiments, an antibody that binds to an opioid includes an antibody that binds to an opioid and exhibits a dissociation constant ($K_D$) of less than or equal to $5\times10^{-6}$ M, less than or equal to $1\times10^{-6}$ M, less than or equal to $5\times10^{-7}$ M, less than or equal to $1\times10^{-7}$ M, less than or equal to $5\times10^{-8}$ M, less than or equal to $1\times10^{-8}$ M, less than or equal to $5\times10^{-9}$ M, less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$M, less than or equal to $1\times10^{12}$M, less than or equal to $5\times10^{-13}$M, less than or equal to $1\times10^{-13}$ M, less than or equal to $5\times10^{-14}$ M, less than or equal to $1\times10^{-14}$M, less than or equal to $5\times10^{-15}$ M, or less than or equal to $1\times10^{-15}$ M. Exemplary opioids include heroin, a heroin metabolite, 6-acetylmorphine, morphine, fentanyl, a fentanyl analogue, oxycodone, oxymorphone, and hydrocodone.

For example, in an exemplary embodiment, an antibody that binds to an opioid includes an antibody that binds to oxycodone and exhibits a dissociation constant of less than or equal to $5\times10^{-6}$ M, as measured by competitive ELISA.

In some embodiments, an antibody that binds to an opioid includes a monoclonal antibody produced by at least one of the hybridoma cell lines (also referred to as clones or antibody clones) of Table 1. In some embodiments, an antibody that binds to an opioid includes a monoclonal antibody produced by at least one of the hybridoma cell lines (also referred to as clones or antibody clones) of Table 5. In some embodiments, an antibody that binds to an opioid includes a monoclonal antibody produced by at least one of the hybridoma cell lines (also referred to as clones or antibody clones) of Table 7.

In another aspect, this disclosure describes an isolated polynucleotide molecule. In some embodiments, the isolated polynucleotide molecule includes a nucleotide sequence encoding an antibody. In some embodiments, the isolated polynucleotide molecule includes a nucleotide sequence that has at least 75%, at least 80%, at least 85%, at least 90%, at least 95%, at least 96%, at least 97%, at least 98%, or at least 99% sequence identity to nucleotide sequence encoding an antibody described herein. In some embodiments, the isolated polynucleotide molecule includes polynucleotides that hybridize under high stringency to a nucleotide sequence encoding an antibody or a complement thereof. As used herein "stringent conditions" refer to the ability of a first polynucleotide molecule to hybridize, and remain bound to, a second, filter-bound polynucleotide molecule in 0.5 M NaHPO₄, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). In some embodiments, the isolated polynucleotide molecule includes polynucleotides that encode one or more of the CDRs or the heavy and/or light chains of a monoclonal antibody of Table 1. In some embodiments, the isolated polynucleotide molecule includes polynucleotides that encode one or more of the CDRs of Table 2. General techniques for cloning and sequencing immunoglobulin variable domains and constant regions are well known. See, for example, Orlandi et al. (1989) *Proc. Nat'l Acad. Sci. USA* 86:3833.

In another aspect, this disclosure describes recombinant vectors including an isolated polynucleotide. The vector may be, for example, in the form of a plasmid, a viral particle, or a phage. The appropriate DNA sequence may be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector may be used.

In a further aspect, this disclosure also includes a host cell containing at least one of the above-described vectors. The host cell may be a higher eukaryotic cell, such as a mammalian or insect cell, or a lower eukaryotic cell, such as a yeast cell. Or, the host cell may be a prokaryotic cell, such as a bacterial cell, or a plant cell. Introduction of a vector construct into the host cell may be effected by any suitable techniques, such as, for example, calcium phosphate transfection, DEAE-Dextran mediated transfection, or electroporation. (Davis et al., Basic Methods in Molecular Biology (1986)).

A monoclonal antibody may be expressed in mammalian cells, yeast, bacteria, virus, plant or other cells under the control of appropriate promoters. Cell-free translation systems may also be employed to produce such proteins using RNAs derived from the DNA constructs. Appropriate cloning and expression vectors for use with prokaryotic and eukaryotic hosts are described by Sambrook et al., Molecular Cloning: A Laboratory Manual, Second Edition, Cold Spring Harbor, N.Y. (1989).

In another aspect this disclosure described a phage display library that express one or more hypervariable regions from an antibody described herein and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries may be prepared, for example, using the PH.D.-7 Phage Display Peptide Library Kit (Catalog #E8100S) or the PH.D.-12 Phage Display Peptide Library Kit (Catalog #E8110S) available from New England Biolabs Inc., Ipswich, MA. See, for example, Smith and Petrenko (1997) Chem Rev. 97:391-410.

Hybridoma Cell Lines

This disclosure further describes hybridoma cell lines (also referred to herein as "clones" or "antibody clones") expressing monoclonal antibodies including, for example, the hybridoma cell lines of Table 1. In some embodiments, a monoclonal antibody produced by a hybridoma cell line binds to an opioid.

In some embodiments, a monoclonal antibody produced by a hybridoma cell line abrogates binding of the opioid to an opioid receptor. Opioid receptors may include, for example, a μ opioid receptor (MOR), a κ Opioid receptor (KOR), a δ opioid receptor (DOR), or an opioid receptor like-1 (also called a nociceptin or orphanin FQ receptor. In some embodiments, the antibody may decrease the binding of an opioid to an opioid receptor by at least 10 percent (%), at least 15%, at least 20%, at least 25%, at least 30%, at least 40%, at least 50%, at least 60%, at least 70%, at least 80%, at least 90%, at least 95%, or at least 98%. In some embodiments, the antibody may decrease the binding of an opioid to an opioid receptor by up to 20%, up to 25%, up to 30%, up to 40%, up to 50%, up to 60%, up to 70%, up to 80%, up to 90%, up to 95%, up to 98%, or up to 99%.

Hybridoma cell lines may be obtained by various techniques familiar to those skilled in the art. For example, cells from an animal immunized with a desired antigen are immortalized, commonly by fusion with a myeloma cell (see, for example, Kohler and Milstein (1976) *Eur. J. Immunol.* 6:511; J. Goding in "Monoclonal Antibodies: Principles and Practice," Academic Press, pp 59-103 (1986); and Harlow et al., Antibodies: A Laboratory Manual, page 726 (Cold Spring Harbor Pub. 1988). In some embodiments, the immunized animal is preferably a mammal. In some embodiments, the immunized animal is a rat including, for example, a Wistar rat, or a mouse including, for example, a BALB/C mouse. In some embodiments, the cells from the animal are spleen cells. In some embodiments, the cells from the animal are preferably lymphocytes. In some embodiments, the myeloma cell includes a Sp2/0 myeloma cell.

In some embodiments, hybridomas may preferably be generated after magnetic enrichment for antigen-specific cells as in Taylor et al. (J Immunol Methods. 2014; 405:74-86).

Other known methods of producing transformed B cell lines that produce monoclonal antibodies may also be used.

Recombinant Antibodies

This disclosure further describes recombinantly-derived monoclonal antibodies. Recombinantly derived monoclonal antibodies may include, for example, rabbit B cell derived monoclonal antibodies. Monoclonal antibodies of the present disclosure may be produced by any suitable recombinant technique including, for example, by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Such methods may be used to generate human monoclonal antibodies.

Uses for the Anti-Opioid Antibodies

An antibody that binds to an opioid, as described herein, or an antigen binding fragment of such an antibody may be used for any suitable application. For example, a monoclonal antibody may be used in an in vitro or an in vivo method. Methods may include, for example, detection methods, diagnostic methods, or therapeutic methods.

Detection Methods

In one aspect, this disclosure describes the use of an anti-opioid antibody or an antigen binding fragment thereof in a detection method including, for example, a detection assay. In some embodiments, the anti-opioid antibody or an antigen binding fragment thereof includes an anti-opioid antibody or an antigen binding fragment thereof as further described herein.

In some embodiments, a detection method may include detection of an unknown opioid. In some embodiments, a detection method may include detection of a small amount of an opioid. For example, in an exemplary embodiments, a detection method includes detection of less than 10 picograms per milliliter (pg/mL), less than 5 pg/mL, or less than 1 pg/mL or an opioid.

In some embodiments, a detection method may be used in a screening assay including, for example, as part of customs or airport security screening. In such embodiments, the screening assay may include rapid detection of an opioid including, for example, an assay that may be completed in less than 1 hour, less than 30 minutes, less than 20 minutes, less than 10 minutes, less than 5 minutes, or less than 1 minute.

In some embodiments, a detection method may include an immunoassay. Exemplary imunoassays include a radioimmunoassay (RIA), a counting immunoassay (CIA), an enzyme-linked immunosorbent assay (ELISA), a fluoroimmunoassay (FIA), a lateral flow immunoassay (LFIA), a chemiluminescence-immunoassay (CLIA), etc.

In some embodiments, the detection method may include the use of a kit including an anti-opioid antibody or an antigen binding fragment thereof, as further described herein.

Diagnostic Methods

In one aspect, this disclosure describes the use of an anti-opioid antibody or an antigen binding fragment thereof in a diagnostic method including, for example, a diagnostic or forensic assay. In some embodiments, the anti-opioid antibody or an antigen binding fragment thereof preferably includes an anti-opioid antibody or an antigen binding fragment thereof as further described herein.

In some embodiments, a diagnostic or forensic assay may include detection of an unknown opioid. In some embodiments, a diagnostic or forensic assay may include a panel of opioid-specific mAb or mAb fragments to determine whether a sample includes opioids and/or which opioid types. In some embodiments, a diagnostic or forensic assay may be designed to determine if an opioid is present in a subject's bodily fluid including, for example, to determine if the subject has been exposed to or has used an opioid.

Therapeutic or Prophylactic Methods

In one aspect, this disclosure describes the use of an anti-opioid antibody or an antigen binding fragment thereof as a therapeutic. In some embodiments, the anti-opioid antibody or an antigen binding fragment thereof preferably includes an anti-opioid antibody or an antigen binding fragment thereof as further described herein.

Monoclonal antibodies (mAb) have the potential to provide a powerful therapeutic or prophylactic option for substance use disorders because they may selectively sequester the target drug in serum, preventing drug distribution to the brain and drug-induced toxicity including re-narcotization—a phenomenon entailing re-circulation of opioids beyond half-life of opioid antagonists.

Although there are multiple pharmacological interventions available to treat opioid use disorders, issues such as access, side effects, and compliance limit their clinical use. For example, opioid receptor antagonists (for example, naloxone) are pan antidotes; in contrast, antibodies may be selective for the target opioid. Because of their selectivity for the target opioid, opioid-specific mAb may be co-administered with known approved medications for opioid use disorders or opioid overdose reversal (for example, mAb plus naloxone or nalmefene, mAb plus methadone, buprenorphine or naltrexone). Additionally, in contrast to opioid receptor antagonists, opioid-specific antibodies do not interfere with endogenous opioid signaling. Further, mAb may have a longer half-life than opioid receptor antagonists, providing additional protection in overdose scenarios and preventing re-narcotization or the need for multiple doses of opioid antagonists. In further contrast to opioid receptor antagonists, mAb do not cross the blood brain barrier and mAb are not expected to induce severe withdrawal symptoms.

In addition, and in further contrast to an anti-opioid mAb, clinical efficacy of vaccines for substance use disorder may be limited (none has yet been approved or is on the market), as up to 70% of subjects may not achieve antibody levels sufficient for efficacy. Passive immunization with opioid-specific mAb circumvents this limitation. Passive immunization may also allow for greater control over serum antibody concentration while granting near-immediate protection (without the needs for weeks or months and multiple immunizations that may be required for successful vaccination). Additionally or alternatively, in some embodiments, anti-opioid mAb might be administered with an anti-opioid vaccine to protect patients with suboptimal responses to vaccines.

In some embodiments, administration of an anti-opioid antibody or an antigen binding fragment thereof may be used in a method of passive immunization against an opioid. In some embodiments, the anti-opioid antibody or an antigen binding fragment thereof may be administered at least 6 hours, at least 12 hours, or at least 24 hours before an anticipated exposure to an opioid. In some embodiments, the anti-opioid antibody or an antigen binding fragment thereof may be administered after suspected exposure to an opioid or after a known exposure to an opioid. In some embodiments, passive immunization may include the expression of the anti-opioid antibody or an antigen binding fragment thereof by viral-mediated expression of the antibody in a subject. That is, the relevant sequences of the anti-opioid antibody or an antigen binding fragment thereof could be cloned into a suitable viral vector (for example, AAV), and then the viral vector may be introduced into the subject where it is expressed.

In some embodiments, co-administration of multiple anti-opioid antibodies or antigen binding fragments thereof could be used to provide protection against multiple opioids at once. Exemplary combinations include anti-fentanyl mAb+ anti-heroin mAb, anti-fentanyl mAb+anti-oxycodone mAb, anti-heroin mAb+anti-oxycodone mAb, or anti-fentanyl mAb+anti-heroin mAb+anti-oxycodone mAb.

In some embodiments, administration of an anti-opioid antibody or an antigen binding fragment thereof may be used to treat a subject who may be exposed to an opioid, a subject who is suspected of being exposed to an opioid, or a subject who has been exposed to an opioid. In some embodiments, such a subject may include, for example, a soldier, a law enforcement professional, a health profession, a first responder, etc. In some embodiments, a subject may include a victim of a mass casualty incident. In some embodiments, a subject may include an opioid user. In some embodiments, a subject may include a victim of a chemical attack (for example, a drone dispersing carfentanil or an aerosolized fentanyl analog). In some embodiment, a subject may include an infant born to an opioid user including, for example, an infant suffering from neonatal opioid syndrome. Compositions Including Anti-Opioid Antibodies In some embodiments, this disclosure describes a composition including at least one of the antibodies described herein.

In some embodiments, the composition may also include, for example, buffering agents to help to maintain the pH in an acceptable range or preservatives to retard microbial growth. A composition may also include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zinc (Zn)-protein complexes); and/or non-ionic surfactants such as TWEEN, PLURONICS, or polyethylene glycol (PEG).

In some embodiments, the composition is a pharmaceutical composition and includes the monoclonal antibody and a pharmaceutically acceptable carrier, diluent or excipient. In the preparation of the pharmaceutical compositions comprising the antibodies described in the teachings herein, a variety of vehicles and excipients may be used, as will be apparent to the skilled artisan.

The pharmaceutical compositions will generally comprise a pharmaceutically acceptable carrier and a pharmacologically effective amount of an antibody, or mixture of antibodies.

The pharmaceutical composition may be formulated as a powder, a granule, a solution, a suspension, an aerosol, a solid, a pill, a tablet, a capsule, a gel, a topical cream, a suppository, a transdermal patch, and/or another formulation known in the art.

For the purposes described herein, pharmaceutically acceptable salts of an antibody are intended to include any art-recognized pharmaceutically acceptable salts including organic and inorganic acids and/or bases. Examples of salts include but are not limited to sodium, potassium, lithium, ammonium, calcium, as well as primary, secondary, and tertiary amines, esters of lower hydrocarbons, such as methyl, ethyl, and propyl. Other salts include but are not limited to organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. For example, the antibody may be prepared as a formulation in a pharmaceutically acceptable diluent, including for example, saline, phosphate buffer saline (PBS), aqueous ethanol, or solutions of glucose, mannitol, dextran, propylene glycol, oils (for example, vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as a solid formulation in an appropriate excipient.

A pharmaceutical composition will often further comprise one or more buffers (for example, neutral buffered saline or phosphate buffered saline), carbohydrates (for example, glucose, sucrose or dextrans), mannitol, proteins, polypeptides or amino acids such as glycine, antioxidants (for example, ascorbic acid, sodium metabisulfite, butylated hydroxytoluene, butylated hydroxyanisole, etc.), bacteriostats, chelating agents such as EDTA or glutathione, adjuvants (for example, aluminum hydroxide), solutes that render the formulation isotonic, hypotonic or weakly hypertonic with the blood of a recipient, suspending agents, thickening agents and/or preservatives. Alternatively, compositions of the present disclosure may be formulated as a lyophilizate.

Any suitable carrier known to those of ordinary skill in the art may be employed in a composition including at least one of the antibodies describes herein. Antibody compositions may be formulated for any appropriate manner of administration, including for example, oral, nasal, mucosal, intravenous, intraperitoneal, intradermal, subcutaneous, and intramuscular administration.

Kits

In another aspect, this disclosure describes a kit including an anti-opioid antibody. The antibodies in the kit may be labeled with one or more detectable markers, as described herein.

A kit may include one or more containers filled with one or more of the monoclonal antibodies of the invention. Additionally, the kit may include other reagents such as buffers and solutions. Optionally associated with such container(s) may be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide.

Delivery Devices

In yet another aspect, this disclosure describes a delivery device including an anti-opioid antibody. In some embodiments, the anti-opioid antibody preferably includes an anti-opioid antibody as further described herein. In some embodiments, the anti-opioid antibody may include multiple anti-opioid antibodies against different opioids.

Any suitable delivery device may be used. Exemplary delivery devices include a syrette, a syringe, an auto-injector, an inhaler, and/or a nasal spray. In some embodiments, the delivery device may further include an opioid antagonist such as methadone, buprenorphine, naltrexone, naloxone, nalmefene, etc.

Administration and Treatment

The compositions of the present disclosure may be formulated in pharmaceutical preparations in a variety of forms adapted to the chosen route of administration. One of skill will understand that the composition will vary depending on mode of administration and dosage unit. For example, for parenteral administration, isotonic saline may be used. Other suitable carriers include, but are not limited to alcohol, phosphate buffered saline, and other balanced salt solutions. The compounds of this invention may be administered in a variety of ways, including, but not limited to, intravenous, topical, oral, subcutaneous, intraperitoneal, intranasal, and intramuscular delivery. In some aspects, the compounds of the present disclosure may be formulated for controlled or sustained release. In some aspects, a formulation for controlled or sustained release is suitable for subcutaneous implantation. In some aspects, a formulation for controlled or sustained release includes a patch. A compound may be formulated for enteral administration, for example, formulated as a capsule or tablet.

Administration may be as a single dose or in multiple doses. In some embodiments, the dose is an effective amount as determined by the standard methods, including, but not limited to, those described herein. Those skilled in the art of clinical trials will be able to optimize dosages of particular compounds through standard studies. Additionally, proper dosages of the compositions may be determined without undue experimentation using standard dose-response protocols. Administration includes, but is not limited to, any of the dosages and dosing schedules, dosing intervals, and/or dosing patterns described in the examples included herewith.

The composition including an antibody according to the present disclosure may be administered by any suitable means including, but not limited to, for example, oral, rectal, nasal, topical (including transdermal, aerosol, buccal and/or sublingual), vaginal, parenteral (including subcutaneous, intramuscular, and/or intravenous), intradermal, intravesical, intra joint, intra-arteriole, intraventricular, intracranial, intraperitoneal, intranasal, or by inhalation.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that may be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparations may be pyrogen-free. Many suitable formulations are known, including polymeric or protein microparticles encapsulating drug to be released, ointments, gels, or solutions which may be used topically or locally to administer drug, and even patches, which provide controlled release over a prolonged period of time. These may also take the form of implants.

The compounds may also be provided in a lyophilized form. Such compositions may include a buffer, for example, bicarbonate, for reconstitution prior to administration, or the buffer may be included in the lyophilized composition for reconstitution with, for example, water. The lyophilized composition may further comprise a suitable vasoconstrictor, for example, epinephrine. The lyophilized composition may be provided in a syringe, optionally packaged in combination with the buffer for reconstitution, such that the reconstituted composition may be immediately administered to a patient.

As used herein "treating" or "treatment" may include therapeutic and/or prophylactic treatments. "Treating a disorder," as used herein, is not intended to be an absolute term. Treatment may lead to an improved prognosis or a reduction in the frequency or severity of symptoms. A "therapeutically effective" concentration or amount as used herein is an amount that provides some improvement or benefit to the subject. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder including, for example, opioid-induced respiratory depression and/or bradycardia. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90%, 80%, 70%, 60%, 50%, 40%, 30%, 20%, 10%, 5%, or 1% as frequent or severe as symptoms experienced by an untreated individual.

In some embodiments, for example, a composition including an antibody according to the present disclosure may be given before a subject is exposed to an opioid to prevent or mitigate the effects of opioid exposure. Additionally or alternatively, a composition including an antibody according to the present disclosure may be given after a subject is exposed to an opioid to reverse or mitigate the effects of opioid exposure.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compositions may be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio between $LD_{50}$ and $ED_{50}$. Compositions that exhibit high therapeutic indices may be preferred. The data obtained from cell culture assays and animal studies may be used in formulating a range of dosage for use in humans. The dosage of such compositions may preferably lie within a range of circulating concentrations that include the $ED_{50}$ with little or no toxicity. The dosage may vary within this range depending upon the dosage form employed and the route of administration utilized. The exact formulation, route of administration and dosage may be chosen by the individual physician in view of the patient's condition.

A composition as described herein may be administered at once, or may be divided into a number of smaller doses to be administered at intervals of time. For example, compositions may be administered repeatedly, for example, at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects, an effective amount is an amount that is effective to achieve a reduction of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to the expected reduction in the parameter in an individual not treated with the agent.

In some aspects, a method further includes the administration of one or more additional therapeutic agents. One or more additional therapeutic agents may be administered before, after, and/or coincident to the administration of a monoclonal antibody as described herein. An additional therapeutic agent may include, for example, another treatment for opioid use disorder such as an opioid agonist or antagonist. Exemplary opioid agonists and antagonists include methadone, buprenorphine, naltrexone, naloxone, nalmefene, etc. Additional therapeutic agents may be administered separately or as part of a mixture or cocktail. In some aspects, the administration of an antibody may allow for the effectiveness of a lower dosage of other therapeutic modalities when compared to the administration of the other therapeutic modalities alone, providing relief from the toxicity observed with the administration of higher doses of the other modalities. In some aspects, anti-opioid mAb may be given with anti-opioid vaccines to protect patients with suboptimal responses to vaccines.

In some aspects, the administration of a composition as described herein and the at least one additional therapeutic agent demonstrate therapeutic synergy. In some aspects, a measurement of response to treatment observed after administering both an antibody as described herein and the additional therapeutic agent is improved over the same measurement of response to treatment observed after administering either the antibody or the additional therapeutic agent alone.

Exemplary Anti-Oxycodone Antibody Embodiments

1. An anti-opioid antibody or antigen binding fragment thereof, the antibody or antigen binding fragment thereof comprising
    an antibody or antigen binding fragment thereof that binds to the same epitope as an antibody produced by one of the clones of Table 1; or
    an antibody produced by one of the clones of Table 1.

2. An anti-opioid antibody or antigen binding fragment thereof, wherein the anti-opioid antibody or antigen binding fragment thereof comprises a monoclonal antibody or antigen binding fragment thereof comprising
    a heavy chain variable region of an antibody produced by one or more of the clones of Table 1; or
    a light chain variable region of an antibody produced by one or more of the clones of Table 1; or
    both.

3. An anti-opioid antibody or antigen binding fragment thereof, wherein the anti-opioid antibody or antigen binding fragment thereof comprises a monoclonal antibody or antigen binding fragment thereof comprising
    a heavy chain variable region comprising one or more complementary determining regions (CDRs) of Table 2A; or
    a light chain variable region comprising one or more CDRs of Table 2B; or
    both.

4. An anti-opioid antibody or antigen binding fragment thereof, wherein the anti-opioid antibody or antigen binding fragment thereof comprises a monoclonal antibody or antigen binding fragment thereof comprising each of the complementary determining regions (CDRs) of a heavy chain variable region of a monoclonal antibody produced by one of the clones of Table 1; or each of the CDRs of a light chain variable region of a monoclonal antibody produced by one of the clones of Table 1;

each of the CDRs of a heavy chain variable region of a monoclonal antibody produced by one of the clones of Table 1 and each of the CDRs of a light chain variable region of a monoclonal antibody produced by one of the clones of Table 1; or each of the CDRs of a heavy chain variable region of a monoclonal antibody produced by one of the clones of Table 1, and each of the CDRs of a light chain variable region of a monoclonal antibody produced by the same clone.

5. The anti-opioid antibody or antigen binding fragment thereof of Embodiment 4, wherein the CDRs of the heavy chain variable region have an amino acid sequence set forth in Table 2A; or wherein the CDRs of the light chain variable region have an amino acid sequence set forth in Table 2B; or both.

6. An anti-opioid antibody or antigen binding fragment thereof, wherein the anti-opioid antibody or antigen binding fragment thereof comprises a monoclonal antibody or antigen binding fragment thereof comprising an amino acid sequence having at least 75%, at least 80%, at least 85%, at least 90%, at least 95%, at least 96%, at least 97%, at least 98%, or at least 99% sequence identity to one or more complementary determining regions (CDRs) of the heavy chain variable region of a monoclonal antibody produced by a clone of Table 1; or at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 1; or at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 1 and at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 1.

7. The anti-opioid antibody or antigen binding fragment thereof of any one of Embodiments 2 to 6, wherein the anti-opioid antibody comprises a humanized antibody.

8. The anti-opioid antibody or antigen binding fragment thereof of any one of Embodiments 2 to 6, wherein the anti-opioid antibody or antigen binding fragment thereof comprises an antibody or antigen binding fragment thereof produced by one or more of the clones of Table 1.

9. The anti-opioid antibody or antigen binding fragment thereof of any one of the preceding Embodiments, wherein the anti-opioid antibody or antigen binding fragment thereof decreases the binding of an opioid to an opioid receptor by at least 10 percent (%), at least 15%, at least 20%, at least 25%, at least 30%, at least 40%, at least 50%, at least 60%, at least 70%, at least 80%, at least 90%, at least 95%, or at least 98%.

10. The anti-opioid antibody or antigen binding fragment thereof of any one of the preceding Embodiments, wherein the anti-opioid antibody or antigen binding fragment thereof comprises an antibody or antigen binding fragment thereof that selectively binds to oxycodone, hydrocodone, an oxycodone derivative, a hydrocodone derivative, an oxycodone metabolite, or a hydrocodone metabolite.

11. A composition comprising the anti-opioid antibody or antigen binding fragment thereof of any one of Embodiments 1 to 10.

12. A method comprising administering the anti-opioid antibody or antigen binding fragment thereof of any one of Embodiments 1 to 10 to a subject.

13. The method of Embodiment 12, wherein the subject may be exposed to an opioid, is suspected of being exposed to an opioid, or has been exposed to an opioid.

14. The method of Embodiment 13, the method further comprising treating the subject with an opioid antagonist.

15. A method comprising detecting an opioid using the anti-opioid antibody or antigen binding fragment thereof of any one of Embodiments 1 to 10, the method comprising detecting the opioid in sample using an immunoassay.

16. The method of Embodiment 15, wherein the immunoassay may be completed in less than 1 hour, less than 30 minutes, less than 20 minutes, less than 10 minutes, less than 5 minutes, or less than 1 minute.

17. A kit comprising the anti-opioid antibody or antigen binding fragment thereof of any one of Embodiments 1 to 10.

Exemplary Anti-Heroin Antibody Embodiments

1. An anti-opioid antibody or antigen binding fragment thereof, the antibody or antigen binding fragment thereof comprising an antibody or antigen binding fragment thereof that binds to the same epitope as an antibody produced by one of the clones of Table 5; or an antibody produced by one of the clones of Table 5.

2. An anti-opioid antibody or antigen binding fragment thereof, wherein the anti-opioid antibody or antigen binding fragment thereof comprises a monoclonal antibody or antigen binding fragment thereof comprising a heavy chain variable region of an antibody produced by one or more of the clones of Table 5; or a light chain variable region of an antibody produced by one or more of the clones of Table 5; or both.

3. An anti-opioid antibody or antigen binding fragment thereof, wherein the anti-opioid antibody or antigen binding fragment thereof comprises a monoclonal antibody or antigen binding fragment thereof comprising a heavy chain variable region comprising one or more complementary determining regions (CDRs) of Table 6A; or a light chain variable region comprising one or more CDRs of Table 6B; or both.

4. An anti-opioid antibody or antigen binding fragment thereof, wherein the anti-opioid antibody or antigen binding fragment thereof comprises a monoclonal antibody or antigen binding fragment thereof comprising each of the complementary determining regions (CDRs) of a heavy chain variable region of a monoclonal antibody produced by one of the clones of Table 5; or each of the CDRs of a light chain variable region of a monoclonal antibody produced by one of the clones of Table 5;

each of the CDRs of a heavy chain variable region of a monoclonal antibody produced by one of the clones of Table 5 and each of the CDRs of a light chain variable region of a monoclonal antibody produced by one of the clones of Table 5; or each of the CDRs of a heavy chain variable region of a monoclonal antibody produced by one of the clones of Table 5, and each of the CDRs of a light chain variable region of a monoclonal antibody produced by the same clone.

5. The anti-opioid antibody or antigen binding fragment thereof of Embodiment 4, wherein the CDRs of the heavy chain variable region have an amino acid sequence set forth in Table 6A; or wherein the CDRs of the light chain variable region have an amino acid sequence set forth in Table 6B; or both.

6. An anti-opioid antibody or antigen binding fragment thereof, wherein the anti-opioid antibody or antigen binding fragment thereof comprises a monoclonal antibody or antigen binding fragment thereof comprising an amino acid sequence having at least 75%, at least 80%, at least 85%, at least 90%, at least 95%, at least 96%, at least 97%, at least 98%, or at least 99% sequence identity to one or more complementary determining regions (CDRs) of the heavy chain variable region of a monoclonal antibody produced by a clone of Table 5; or at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 5, or at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 5 and at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 5.

7. The anti-opioid antibody or antigen binding fragment thereof of any one of Embodiments 2 to 6, wherein the anti-opioid antibody comprises a humanized antibody.

8. The anti-opioid antibody or antigen binding fragment thereof of any one of Embodiments 2 to 6, wherein the anti-opioid antibody or antigen binding fragment thereof comprises an antibody or antigen binding fragment thereof produced by one or more of the clones of Table 5.

9. The anti-opioid antibody or antigen binding fragment thereof of any one of the preceding Embodiments, wherein the anti-opioid antibody or antigen binding fragment thereof decreases the binding of an opioid to an opioid receptor by at least 10 percent (%), at least 15%, at least 20%, at least 25%, at least 30%, at least 40%, at least 50%, at least 60%, at least 70%, at least 80%, at least 90%, at least 95%, or at least 98%.

10. The anti-opioid antibody or antigen binding fragment thereof of any one of the preceding Embodiments, wherein the anti-opioid antibody or antigen binding fragment thereof comprises an antibody or antigen binding fragment thereof that selectively binds to heroin, a heroin metabolite, or a heroin derivative.

11. The anti-opioid antibody of Embodiment 10, wherein the anti-opioid antibody or antigen binding fragment thereof comprises an antibody that selectively binds to morphine.

12. A composition comprising the anti-opioid antibody or antigen binding fragment thereof of any one of Embodiments 1 to 11.

13. A method comprising administering the anti-opioid antibody or antigen binding fragment thereof of any one of Embodiments 1 to 11 to a subject.

14. The method of Embodiment 13, wherein the subject may be exposed to an opioid, is suspected of being exposed to an opioid, or has been exposed to an opioid.

15. The method of Embodiment 14, the method further comprising treating the subject with an opioid antagonist.

16. A method comprising detecting an opioid using the anti-opioid antibody or antigen binding fragment thereof of any one of Embodiments 1 to 11, the method comprising detecting the opioid in sample using an immunoassay.

17. The method of Embodiment 16, wherein the immunoassay may be completed in less than 1 hour, less than 30 minutes, less than 20 minutes, less than 10 minutes, less than 5 minutes, or less than 1 minute.

18. A kit comprising the anti-opioid antibody or antigen binding fragment thereof of any one of Embodiments 1 to 11.

Exemplary Anti-Fentanyl Antibody Embodiments

1. An anti-opioid antibody or antigen binding fragment thereof, the antibody or antigen binding fragment thereof comprising an antibody or antigen binding fragment thereof that binds to the same epitope as an antibody produced by one of the clones of Table 7; or an antibody produced by one of the clones of Table 7.

2. An anti-opioid antibody or antigen binding fragment thereof, wherein the anti-opioid antibody or antigen binding fragment thereof comprises a monoclonal antibody or antigen binding fragment thereof comprising a heavy chain variable region of an antibody produced by one or more of the clones of Table 7; or a light chain variable region of an antibody produced by one or more of the clones of Table 7; or both.

3. An anti-opioid antibody or antigen binding fragment thereof, wherein the anti-opioid antibody or antigen binding fragment thereof comprises a monoclonal antibody or antigen binding fragment thereof comprising a heavy chain variable region comprising one or more complementary determining regions (CDRs) of Table 8A; or a light chain variable region comprising one or more CDRs of Table 8B; or both.

4. An anti-opioid antibody or antigen binding fragment thereof, wherein the anti-opioid antibody or antigen binding fragment thereof comprises a monoclonal antibody or antigen binding fragment thereof comprising each of the complementary determining regions (CDRs) of a heavy chain variable region of a monoclonal antibody produced by one of the clones of Table 7; or each of the CDRs of a light chain variable region of a monoclonal antibody produced by one of the clones of Table 7;

each of the CDRs of a heavy chain variable region of a monoclonal antibody produced by one of the clones of Table 7 and each of the CDRs of a light chain variable region of a monoclonal antibody produced by one of the clones of Table 7; or each of the CDRs of a heavy chain variable region of a monoclonal antibody produced by one of the clones of Table 7, and each of the CDRs of a light chain variable region of a monoclonal antibody produced by the same clone.

5. The anti-opioid antibody or antigen binding fragment thereof of Embodiment 4, wherein the CDRs of the heavy chain variable region have an amino acid sequence set forth in Table 8A; or wherein the CDRs of the light chain variable region have an amino acid sequence set forth in Table 8B; or both.

6. An anti-opioid antibody or antigen binding fragment thereof, wherein the anti-opioid antibody or antigen binding fragment thereof comprises a monoclonal antibody or antigen binding fragment thereof comprising an amino acid sequence having at least 75%, at least 80%, at least 85%, at least 90%, at least 95%, at least 96%, at least 97%, at least 98%, or at least 99% sequence identity to one or more complementary determining regions (CDRs) of the heavy chain variable region of a monoclonal antibody produced by a clone of Table 7; or at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 7, or at least 75%, at least 80%, at least 85%, at least 90%, at least 95%, at least 96%, at least 97%, at least 98%, or at least 99% sequence identity to one or more CDRs of the heavy chain variable region of a monoclonal antibody produced by a clone of Table 7 and at least 75%, at least 80%, at least 85%, at least 90%, at least 95%, at least 96%, at least 97%, at least 98%, or at least 99% sequence identity to one or more CDRs of the light chain variable region of a monoclonal antibody produced by a clone of Table 7.

7. The anti-opioid antibody or antigen binding fragment thereof of any one of Embodiments 2 to 6, wherein the anti-opioid antibody comprises a humanized antibody.

8. The anti-opioid antibody or antigen binding fragment thereof of any one of Embodiments 2 to 6, wherein the anti-opioid antibody or antigen binding fragment thereof comprises an antibody or antigen binding fragment thereof produced by one or more of the clones of Table 7.

9. The anti-opioid antibody or antigen binding fragment thereof of any one of the preceding Embodiments, wherein the anti-opioid antibody or antigen binding fragment thereof decreases the binding of an opioid to an opioid receptor by at least 10 percent (%), at least 15%, at least 20%, at least 25%, at least 30%, at least 40%, at least 50%, at least 60%, at least 70%, at least 80%, at least 90%, at least 95%, or at least 98%.

10. The anti-opioid antibody or antigen binding fragment thereof of any one of the preceding Embodiments, wherein the anti-opioid antibody or antigen binding fragment thereof comprises an antibody or antigen binding fragment thereof that selectively binds to fentanyl, a fentanyl analogue, a fentanyl derivative, or a fentanyl metabolite.

11. A composition comprising the anti-opioid antibody or antigen binding fragment thereof of any one of Embodiments 1 to 10.

12. A method comprising administering the anti-opioid antibody or antigen binding fragment thereof of any one of Embodiments 1 to 10 to a subject.

13. The method of Embodiment 12, wherein the subject may be exposed to an opioid, is suspected of being exposed to an opioid, or has been exposed to an opioid.

14. The method of Embodiment 13, the method further comprising treating the subject with an opioid antagonist.

15. A method comprising detecting an opioid using the anti-opioid antibody or antigen binding fragment thereof of any one of Embodiments 1 to 10, the method comprising detecting the opioid in sample using an immunoassay.

16. The method of Embodiment 15, wherein the immunoassay may be completed in less than 1 hour, less than 30 minutes, less than 20 minutes, less than 10 minutes, less than 5 minutes, or less than 1 minute.

17. A kit comprising the anti-opioid antibody or antigen binding fragment thereof of any one of Embodiments 1 to 10.

Exemplary Method of Making Embodiments

1. A method comprising co-administering to a subject:

a vaccine comprising an opioid hapten conjugated to a carrier polypeptide; and a cytokine-signaling immunomodulator;

isolating antibody-producing cells from the subject; and enriching the antibody-producing cells for cells that bind to the opioid hapten.

2. The method of Embodiment 1, wherein the carrier polypeptide comprises keyhole limpet hemocyanin (KLH).

3. The method of Embodiment 2, wherein the KLH is conjugated to the opioid hapten by a tetraglycine linker (SEQ ID NO: 26).

4. The method of any one of the preceding Embodiments, the method further comprising administering an alum adjuvant.

5. The method of any one of the preceding Embodiments, wherein the cytokine-signaling immunomodulator comprises a cytokine neutralizing antibody.

6. The method of any one of the preceding Embodiments, wherein the cytokine-signaling immunomodulator modulates IL-4.

7. The method of any one of the preceding Embodiments, wherein the cytokine-signaling immunomodulator comprises anti-IL-4 antibody.

8. A method comprising identifying a subject, wherein the subj ect has been exposed to an opioid;

isolating antibody-producing cells from the subject; and enriching the antibody-producing cells for a cell or cells that bind to an opioid hapten.

9. The method of any one of the preceding Embodiments, wherein the method further comprises sequencing a B cell receptor, cloning a B cell receptor, or both sequencing and cloning a B cell receptor of an antibody-producing cell that binds to an opioid hapten.

10. The method of Embodiment 9, wherein the method further comprises expression of the B cell receptor in a vector.

11. The method of any one of the preceding Embodiments, wherein enriching the antibody-producing cells comprises antigen-based magnetic enrichment or flow cytometry, or both.

12. A method comprising co-administering to a subject:

a vaccine comprising an opioid hapten conjugated to a carrier polypeptide; and a cytokine-signaling immunomodulator; and isolating plasma from the subject.

13. The method of any one Embodiments 1 to 9 or 12, wherein the method further comprises passive immunization of a second subject with plasma or a component of the plasma from the subject.

14. The method of Embodiment 13, wherein the component of the plasma from the subject comprises hyperimmune human plasma, hyperimmune globulin, or intravenous immunoglobulin (IVIG).

15. The method of Embodiment 13 or 14, wherein the second subject is a human.

15. The method of any one of the preceding Embodiments, wherein the opioid hapten comprises heroin, a heroin metabolite, 6-acetylmorphine, morphine, fentanyl, a fentanyl analogue, oxycodone, oxymorphone, or hydrocodone, or a fragment thereof.

16. The method of any one of the preceding Embodiments, wherein the subject is a human.

EXAMPLES

Example 1

This Example describes the development and characterization of anti-oxycodone monoclonal antibodies.

Methods

Figures 1B, 1C:
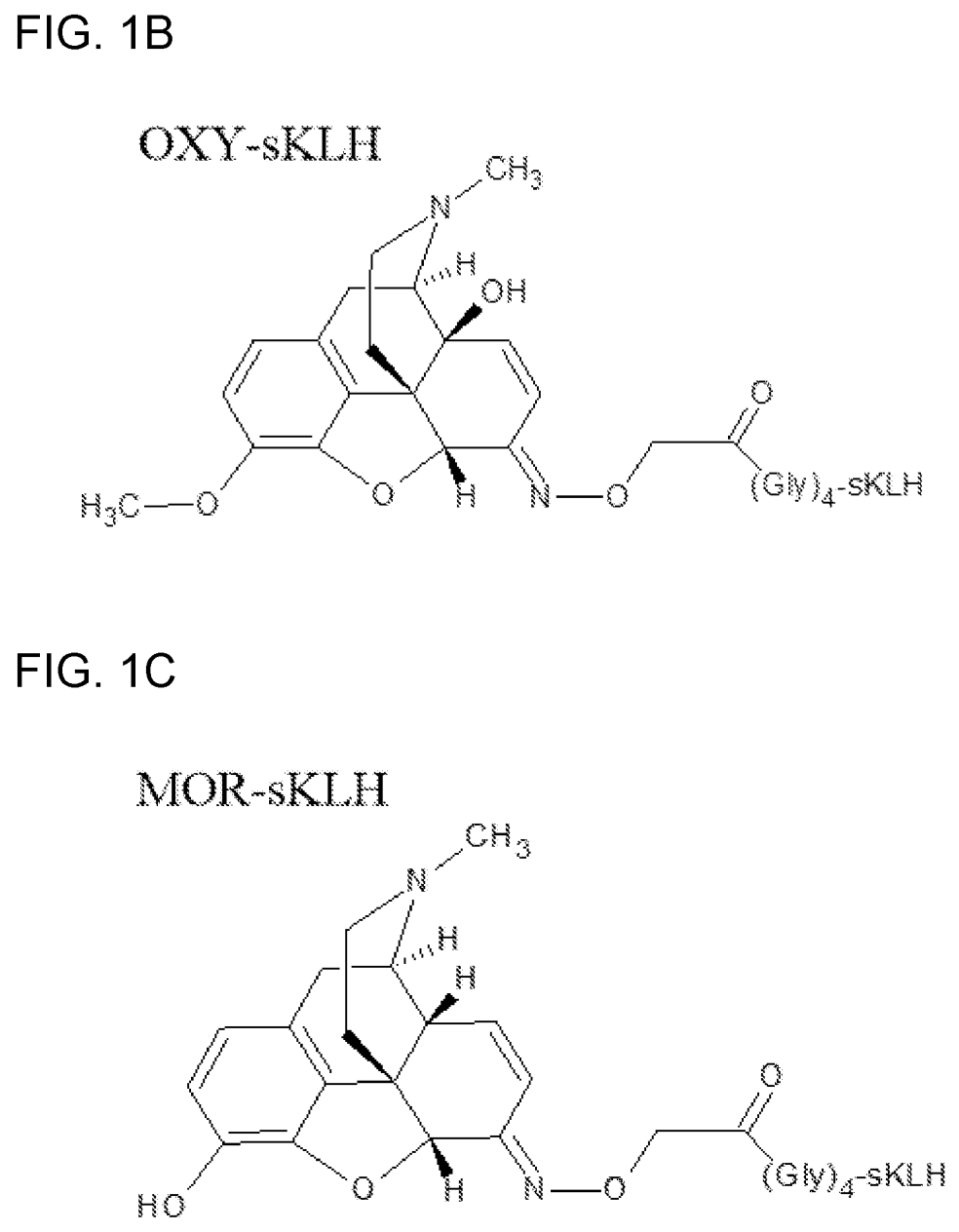

A schematic of the methods used to generate the antibodies is shown in FIG. 1A.

Animals. All procedures were approved by the Institutional Animal Care and Use Committees of the University of Minnesota and Hennepin Healthcare Research Institute, and conducted in accordance with the Guide for the Care and Use of Laboratory Animals (8th Edition, National Academies Press). Male and female Balb/c mice (Jackson Laboratory, Bar Harbor, ME) were 7 weeks on arrival, and male Sprague Dawley rats (Envigo, Indianapolis, IN) were 8-10 weeks on arrival. All animals were housed under standard conditions with a 12/12 hour light/dark cycle and given food and water ad libitum.

Hapten and conjugates. The oxycodone (OXY) hapten containing a tetraglycine [(Gly)$_4$] linker (SEQ ID NO: 26) were synthesized as previously described (Pravetoni et al., *J Pharmacol Exp Ther.* 2012; 341:225-232; Raleigh et al., *J Pharmacol Exp Ther.* 2013, 344(2):397-406; Raleigh et al., *J Pharmacol Exp Ther.* 2019; 368(2):282-291), and then conjugated via carbodiimide chemistry (Baruffaldi et al., *Mol Phar.* 2018; 15(11):4947-4962) to keyhole limpet hemocyanin (KLH) carrier protein for immunogens, to phycoerythrin (PE) for magnetic enrichment, or to ovalbumin (OVA) or bovine serum albumin (BSA) for screening.

Immunizations. Mice (n=4 per group) were immunized on days 0 and 28 with oxycodone-based hapten conjugated to keyhole limpet hemocyanin (KLH) through a tetraglycine linker (SEQ ID NO: 26) (OXY-KLH) vaccine with alum adjuvant (FIG. 1B), with or without depletion of interleukin-4 (IL-4) by neutralizing antibody as described in (Laudenbach et al. *Sci Rep.* 2018; 8(1):5508). Four days after the second vaccination, lymph nodes and spleens were collected and pooled prior to hybridoma fusion. For hybridomas with the prefix HY1, immunization was with OXY-KLH adsorbed on alum; for hybridomas with the prefix HY2, immunization was with OXY-KLH adsorbed on alum in conjunction with IL-4 depletion.

Hybridoma fusion. Hybridomas were generated essentially as described in Spanier et al. (*Nat Commun.* 2016; 7:11804) following magnetic enrichment for antigen-specific cells as in Taylor et al. (*J Immunol Methods.* 2014; 405:74-86). (See also Laudenbach et al. Journal of Immunology 2015; 194:5926-5936. ) Briefly, lymph nodes and spleens from immunized mice were processed to a single-cell suspension, and pelleted at 1600 rpm for 5 minutes. Pellets were resuspended in DMEM, opioid-based hapten conjugated to PE was added to a final concentration of 6.7 nM, and the mixture was incubated 25 minutes at room temperature. Cells were washed with 10 mL DMEM and resuspended in 125 µl DMEM, and 25 µl anti-PE microbeads (Miltenyi Biotech, Auburn, CA) were added and incubated for 15 minutes at room temperature. Cells were suspended in 3 mL DMEM and passed through a magnetic column. Columns were washed three times with DMEM, removed from magnet, and eluted with 5 mL ClonaCell-HY Medium A (StemCell Technologies, Cambridge, MA). Eluted cells were counted, washed with serum free media, and combined with Sp2/0Ag14 (ATCC® CRL1581™, American Type Culture Collection, Manassas, VA) in a 1:5 ratio (myeloma: splenocyte), and washed three times to remove residual serum. Fusion was performed using a ClonaCell-HY Hybridoma kit (StemCell Technologies, Cambridge, MA), according to manufacturer's instructions.

Hybridoma fusions were plated on semisolid methylcellulose medium with HAT selection (ClonaCell-HY Medium D). After 10-14 days at 37° C. and 5% $CO_2$, visible hybridoma colonies were isolated and transferred to 96-well plates containing 100 µL culture medium per well and incubated for 2-4 days prior to screening.

Hybridoma screening. Colonies were screened for antibody expression by ELISA. 96-well plates were coated with 5 ng/well conjugated opioid (OXY-OVA) blocked with 1% gelatin. For each clone, 50 µL conditioned medium was diluted 1:1 with PBS-T and incubated with the coated plate for 2 hours. Plates were washed and incubated overnight with goat-α-mouse-HRP secondary antibody (Jackson ImmunoResearch, West Grove, PA), and peroxidase activity was measured with o-phenylenediamine substrate (Millipore Sigma, Burlington, MA). Absorbance was read at 492 nm on Tecan Infinite M1000 microplate reader (Tecan, Mannedorf, Switzerland).

Determination of relative antibody affinity. For competitive ELISA, 96-well plates were coated with 5 ng/well cognate antigen overnight and blocked with 1% gelatin. Plates were incubated with purified antibody, 0.04-0.06 µg/mL, for 2 hours in the presence of free opioid as competitor in a range of concentrations from 1 mM to 1 pM. Plates were washed and incubated overnight with HRP-conjugated goat anti-mouse secondary antibody, and HRP activity was measured using SigmaFast OPD substrate. Biolayer interferometry was performed using ForteBio BLItz system (Molecular Devices, San Jose, CA) with streptavidin biosensors. Biosensors were loaded with 2 µM fentanyl-biotin for 60 sec, binding was measured with 100 nM mAb for 2 min, and dissociation was measured in PBS for 2 min.

Antibody scale up and purification. Hybridomas were adapted to DMEM (Corning Inc, Corning, NY) supplemented with 10% fetal bovine serum, hypoxanthine/thymidine (Sigma), and 2-mercaptoethanol and inoculated into Integra Celline 1000 bioreactors (Wheaton, Millville, NJ).

Supernatant containing secreted mAb was purified by affinity chromatography with Protein A Sepharose (GE Healthcare, Chicago, IL). Antibody was sterilized by 0.2 µm filtration, aliquoted in preservative-free PBS, pH 7.2, and stored at 4° C.

Sequencing. RNA was purified from hybridomas with RNeasy Micro kit (Qiagen) according to manufacturer's instructions. Sequencing of B cell receptor heavy and light chains was performed using primers sets described in Ho et al. (J Immunol Methods. 2016; 438:67-70).

Drug challenges and pharmacokinetics. For drug challenges, mice were passively immunized with control antibody (Gammagard, Baxalta Inc) or anti-opioid mAb in sterile PBS, 40-80 mg/kg as indicated in figure legends. To determine bioavailability and serum stability of mAb, approximately 50 μL of blood was collected by facial vein sampling at least 1 hour prior to drug challenge and 20-24 hours after passive immunization. Mice were injected s.c. with 2.25 mg/kg or 5.0 mg/kg oxycodone, 1.0 mg/kg heroin, or 0.1 mg/kg fentanyl, and antinociception was evaluated by latency to respond on a hot plate set to 54° C. (Columbus Instruments, Columbus, OH) 30 min post-injection. Antinociception was reported as percent maximum possible effect (% MPE), and was calculated as (latency post injection–baseline latency)/(60–baseline latency)×100. For oxycodone and heroin, mice were euthanized by $CO_2$ inhalation and decapitated, and brain and whole trunk blood were collected for drug concentration analysis. Brain and serum oxycodone concentrations were measured by GC-MS, and concentration of heroin, 6-monoacetyl morphine (6MAM), and morphine were analyzed by LC-MS in the Pharmacokinetics Laboratory Core at University of Minnesota. For fentanyl, mice were evaluated for heart rate and breath rate using a MouseOx Plus pulse oximeter (Starr Life Sciences, Oakmont, PA). Rats were passively immunized with 60 mg/kg anti-fentanyl mAb i.p. and 24 hours later challenged with 0.1 mg/kg fentanyl s.c. Antinociception, heart rate, and respiratory behavior were measured every 15 min post-injection.

Subclass ELISA. Plates were coated with 5 ng/well OXY-OVA, M-BSA, or F-BSA, blocked with 1% gelatin, and incubated for 2 hours with 50 μL conditioned media from positive hybridoma clones. Plates were washed and incubated with HRP-conjugated subclass-specific goat anti-mouse secondary antibodies (Alpha Diagnostics International) to identify clones expressing $IgG_1$, $IgG_{2a}$, or $IgG_3$ mAb.

Data analysis. Statistical analysis was performed using Prism (GraphPad, La Jolla, CA). Mean % MPE, drug concentrations, oxygen saturation (% $SaO_2$), heart rate (beats per minute, bpm) and breath rate (breaths per minute, brpm) were analyzed by ordinary one-way ANOVA followed by post-hoc analysis by Tukey's multiple comparisons test.

Results

This Example describes the use of a platform to rapidly generate hybridomas expressing opioid-specific antibodies from mice immunized with an anti-oxycodone vaccine OXY-KLH. Antibody-expressing B cells were magnetically enriched prior to hybridoma fusion, increasing the number of successful clones expressing opioid-specific mAb. Using this method, 22 clones expressing high-affinity mAb against oxycodone were generated (Table 1) and were characterized (see, for example, FIG. 2). Clones generated using OXY-KLH vaccine with alum adjuvant without depletion of interleukin-4 (IL-4) labeled with/include the prefix HY1 or HY-1; clones generated using OXY-KLH vaccine with alum adjuvant with depletion of interleukin-4 (IL-4) labeled with/include the prefix HY2 or HY-2.

Figures 2A, 2B, 2C, 2D:
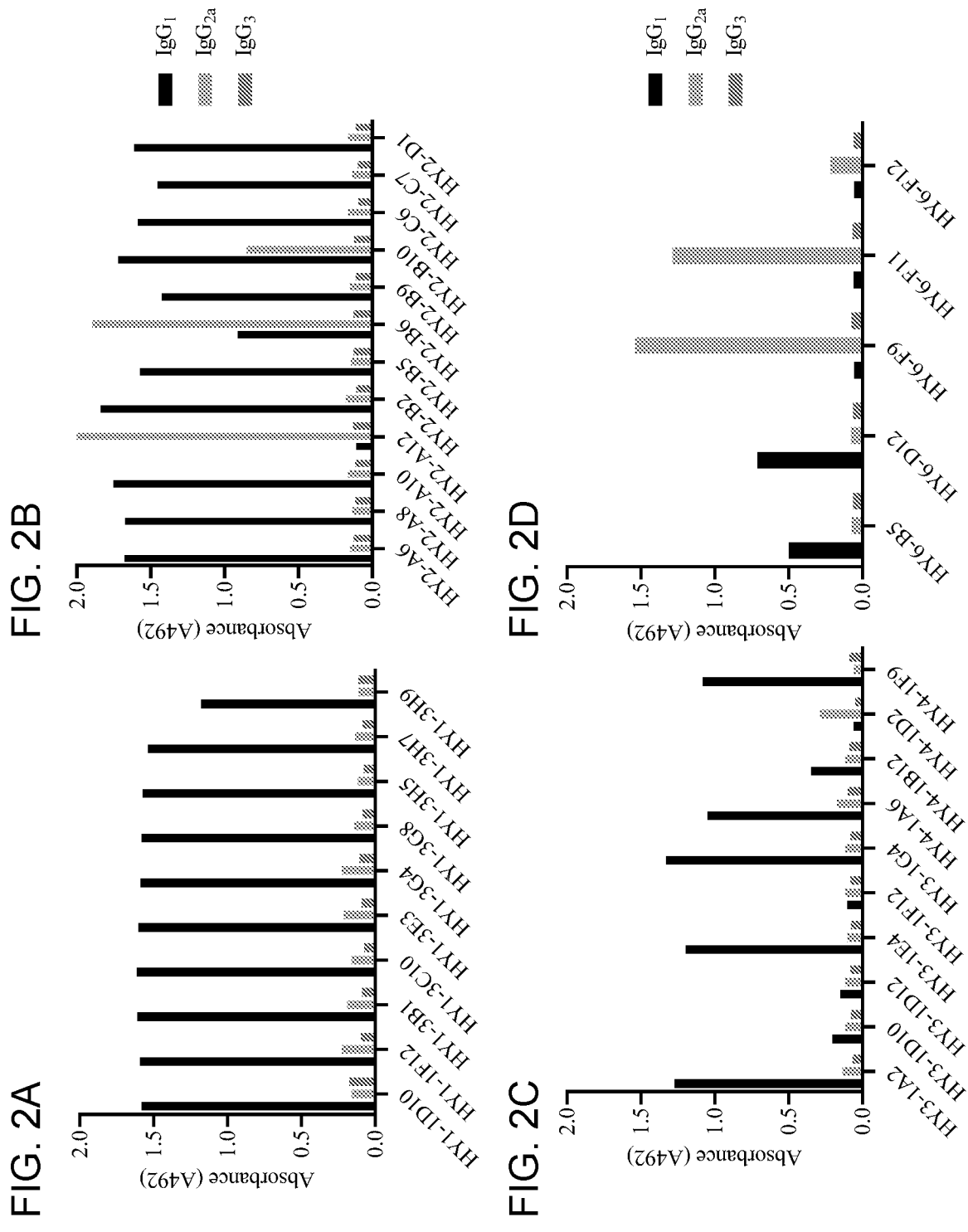
FIG. 2A-FIG. 2D show characterization of exemplary opioid-specific mAb. The IgG subclass (IgG$_1$, IgG$_{2a}$, or IgG$_3$) of the opioid-specific mAb was determined by ELISA. Hybridomas were generated from magnetically enriched opioid-specific B cells from mice immunized with either OXY-KLH adsorbed on alum adjuvant (FIG. 2A, HY1), OXY-KLH adsorbed on alum adjuvant co-administered with an anti-IL-4 mAb (FIG. 2B, HY2), M-sKLH adsorbed on alum (FIG. 2C, HY3), M-sKLH and CpG adjuvant (FIG. 2C, HY4), or F-sKLH adsorbed on alum (FIG. 2D, HY6).
Figures 3A, 3B, 3C:
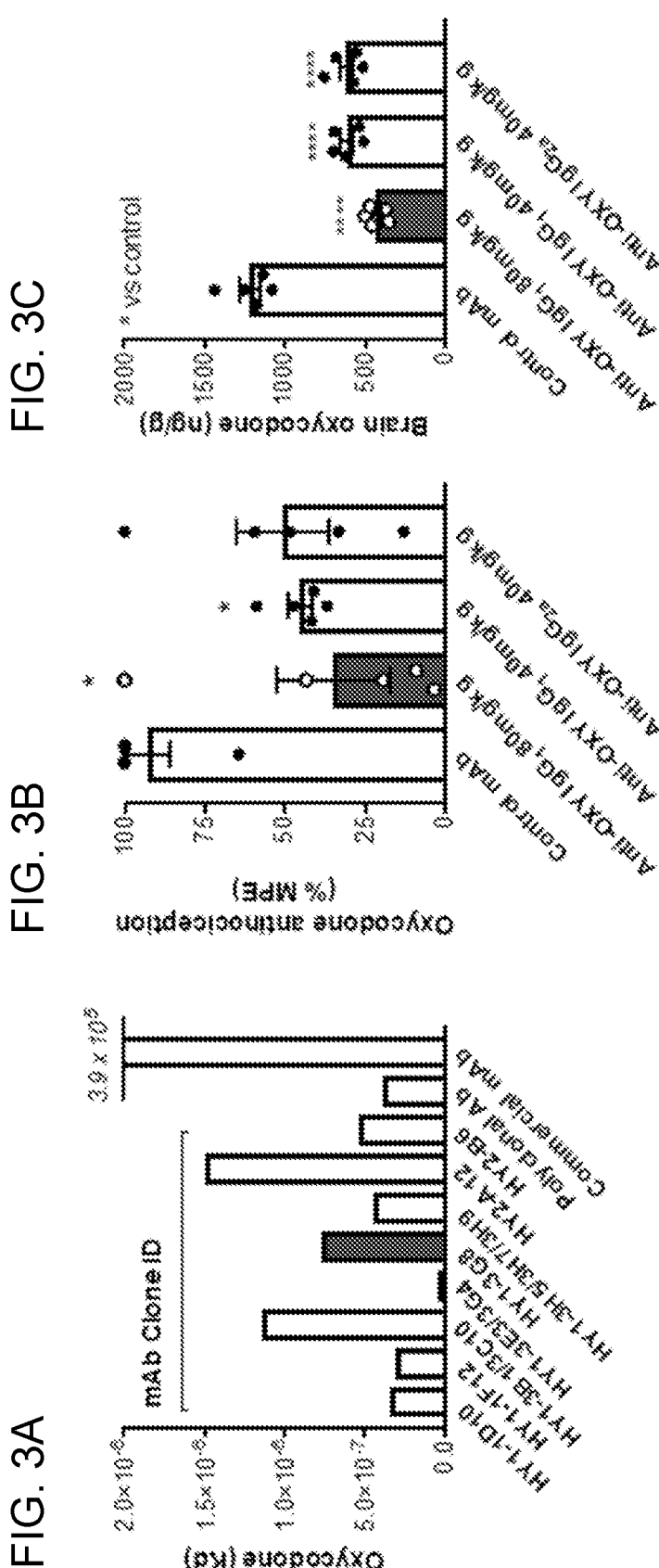
FIG. 3A-FIG. 3C show characterization of exemplary purified opioid-specific mAb.
Figure 4A:
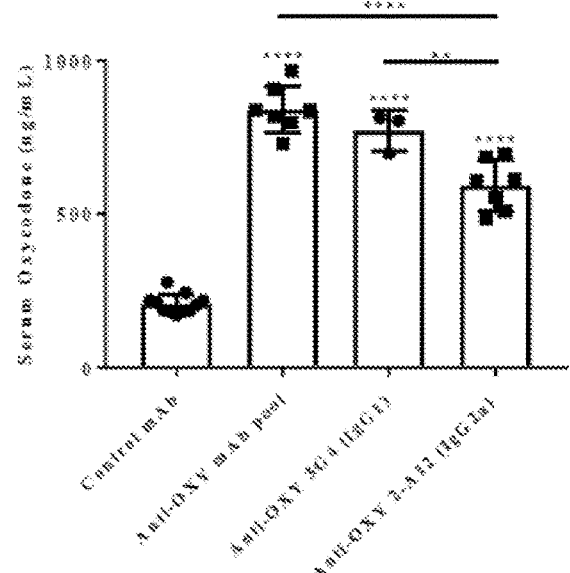
FIG. 4A-FIG. 4D show in vivo efficacy of exemplary anti-oxycodone mAb.
Figure 4B:
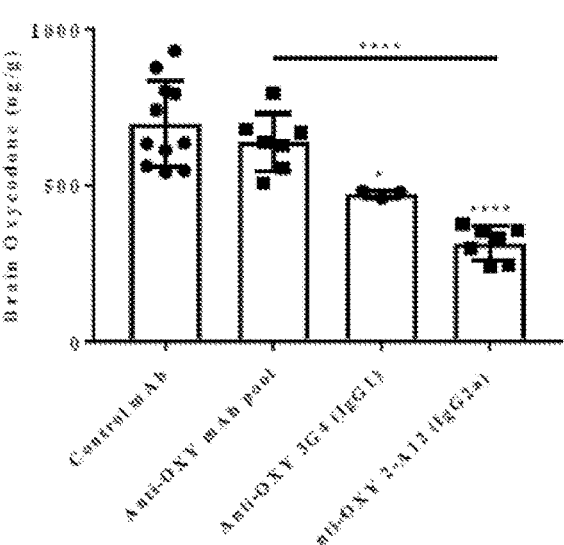
Figure 4C:
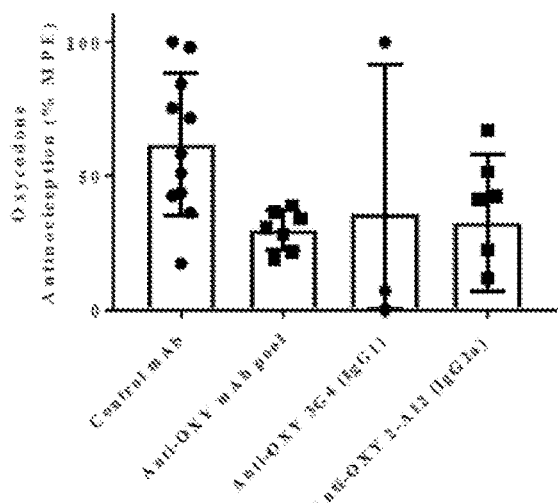
Figure 4D:
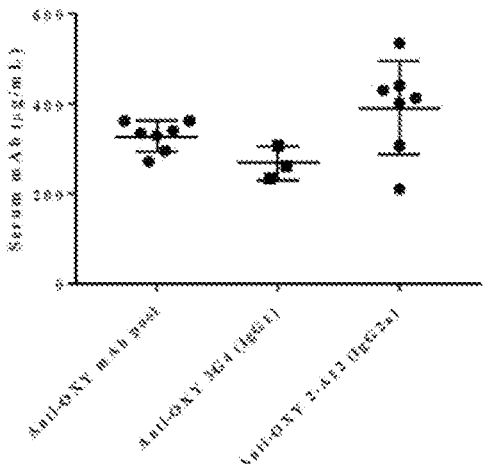

The resulting mAb exhibited low- to mid-nanomolar affinity by competitive ELISA. Subclass ELISA was performed to identify clones expressing $IgG_1$, $IgG_{2a}$, or $IgG_3$ antibodies; results are shown in FIG. 2B. Whereas all clones isolated from immunization with aluminum adjuvant alone expressed $IgG_1$ α-oxycodone mAb (FIG. 2A), immunization with alum with α-IL-4 allowed isolation of several clones expressing IgG2a anti-oxycodone mAb (FIG. 2B), suggesting that choice of adjuvant impacts the profile of mAb generated from hybridomas.

Immunization of mice with OXY-KLH in combination with an antibody to deplete interleukin-4 resulted in an increase in clones expressing IgG2a antibody subclass. (See FIG. 2B.) Passive immunization with purified oxycodone-specific mAb reduced oxycodone-induced antinociception and brain distribution following a dose of oxycodone in mice. (FIG. 3B, FIG. 3C, FIG. 4A-C.) As shown in FIG. 4, administration of pooled mAb reduced oxycodone-induced antinociception and brain distribution following a dose of oxycodone in mice, demonstrating that a a combination of mAb may also be safely administered and effective.

Exemplary protein sequences of the antibodies are shown in FIG. 6 and CDRs of the antibodies are identified in Table 2A-Table 2B. Exemplary DNA sequences of the heavy chains are shown in Table 3A and exemplary DNA sequences of the reverse complements of the light chains are shown in Table 3B. Dissociation constants of the antibodies are shown in Table 4.

Figure 5A:
FIG. 5A shows alignments of the CDR3 region of exemplary anti-oxycodone mAb. Sequences of heavy chain variable regions were determined by RT-PCR/PCR and Sanger sequencing.
Figure 5B:
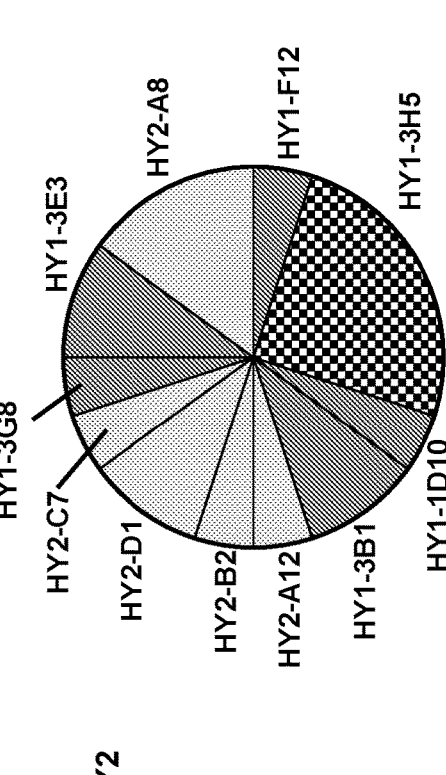
FIG. 5B shows the number of clones found to exhibit the heavy chain CDR3 sequences in A. Dark gray slices indicate CDR3 sequences obtained from HY1 clones; light gray slices indicate sequences obtained from HY2 clones. Checkered slice indicates a sequence identified in clones from both groups.
Figure 5F:
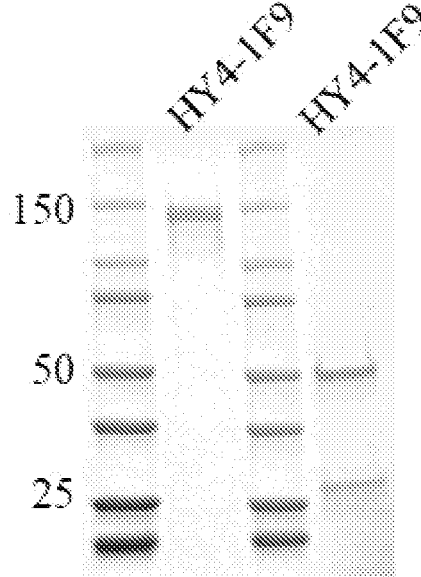
Figure 5G:
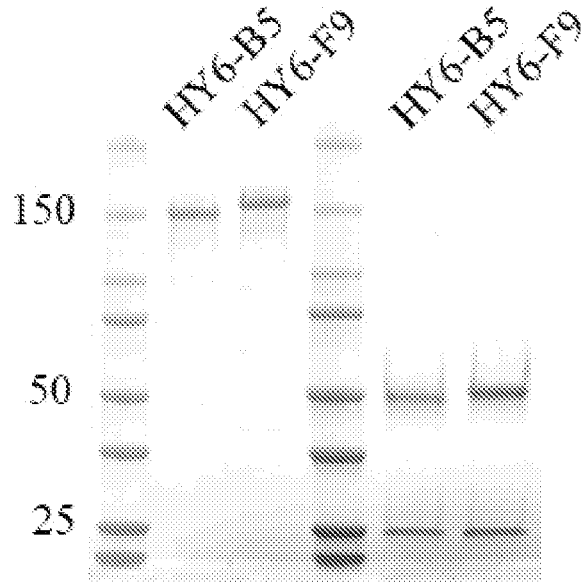

HY1-3G8 antibody was purified and characterized by dynamic light scattering and SDS-PAGE to evaluate aggregation state and molecular weight (FIG. 5D). These data support scalability of the mAb production to support late-stage characterization and in vivo studies in large animal models.

In vivo efficacy of anti-oxycodone mAb. Selected a-oxycodone mAb were purified from hybridoma supernatant, and relative affinity was determined by competitive ELISA (FIG. 9A). Anti-oxycodone mAb exhibited $IC_{50}$ within the 10 nM-1 μM range. Several clones were selected for further scale up and characterization; while clone HY1-3E3 exhibited the highest in vitro affinity, the isolated mAb exhibited poor in vivo efficacy in initial tests (FIG. 10). Therefore, two clones with robust mAb expression were selected as leads, including one $IgG_1$ clone (HY1-3G8), and one $IgG_{2a}$ clone (HY2-A12).

To evaluate whether α-oxycodone mAb is able to reduce the effects of oxycodone in vivo, mice were passively immunized with purified mAb 24 hours before a 5.0 mg/kg oxycodone challenge. Doses of either 40 mg/kg or 80 mg/kg HY1-3G8 significantly reduced antinociception in mice compared to a control mAb (FIG. 9B), and 40 mg/kg HY2-A12 reduced antinociception (p=0.065). Thirty minutes after administration of drug, mice were euthanized and the concentration of oxycodone in the brain and serum were measured by GC-MS. Results are shown in FIG. 9C-FIG. 9D. Passive immunization with 40 mg/kg of either $IgG_1$ or $IgG_{2a}$ α-oxycodone mAb reduced brain distribution of drug by approximately 49% (FIG. 9D), whereas 80 mg/kg of $IgG_1$ α-oxycodone mAb reduced brain distribution by 65%. These data suggest that IgG subclass may be not be a major contributor to antibody efficacy in vivo, and that mAb efficacy is dose-dependent.

TABLE 1

| Clone Name | Antibody Name | HY-1 or HY-2 | IgG1 or IgG2a |
|---|---|---|---|
| HY1-1D10 | HY1-1D10 or 1D10 | HY-1 | IgG1 |
| HY1-1F12 | HY1-1F12 or 1F12 | HY-1 | IgG1 |
| HY1-3B1 | HY1-3B1 or 3B1 | HY-1 | IgG1 |
| HY1-3C10 | HY1-3C10 or 3C10 | HY-1 | IgG1 |
| HY1-3E3 | HY1-3E3 or 3E3 | HY-1 | IgG1 |
| HY1-3G4 | HY1-3G4 or 3G4 | HY-1 | IgG1 |
| HY1-3G8 | HY1-3G8 or 3G8 | HY-1 | IgG1 |
| HY1-3H5 | HY1-3H5 or 3H5 | HY-1 | IgG1 |
| HY1-3H7 | HY1-3H7 or 3H7 | HY-1 | IgG1 |
| HY1-3H9 | HY1-3H9 or 3H9 | HY-1 | IgG1 |
| HY2-A6 | HY2-A6 or A6 | HY-2 | IgG1 |

TABLE 1-continued

| Clone Name | Antibody Name | HY-1 or HY-2 | IgG1 or IgG2a |
|---|---|---|---|
| HY2-A8 | HY2-A8 or A8 | HY-2 | IgG1 |
| HY2-A10 | HY2-A10 or A10 | HY-2 | IgG1 |
| HY2-A12 | HY2-A12 or A12 | HY-2 | IgG2a |
| HY2-B2 | HY2-B2 or B2 | HY-2 | IgG1 |
| HY2-B5 | HY2-B5 or B5 | HY-2 | IgG1 |
| HY2-B6 | HY2-B6 or B6 | HY-2 | IgG2a |
| HY2-B9 | HY2-B9 or B9 | HY-2 | IgG1 |
| HY2-B10 | HY2-B10 or B9 | HY-2 | IgG2a |
| HY2-C6 | HY2-C6 or C6 | HY-2 | IgG1 |
| HY2-C7 | HY2-C7 or C7 | HY-2 | IgG1 |
| HY2-D1 | HY2-D1 or D1 | HY-2 | IgG1 |

TABLE 4

| Clone ID | Dissociation Constant |
|---|---|
| HY1-1D10 | 3.39E−07 |
| HY1-1F12 | 3.12E−07 |
| HY1-3B1 | 9.58E−07 |
| HY1-3C10 | 1.32E−06 |
| HY1-3E3 | 5.17E−08 |
| HY1-3G4 | 3.03E−08 |
| HY1-3G8 | 7.68E−07 |
| HY1-3H5 | 5.15E−07 |
| HY1-3H7 | 5.75E−07 |
| HY1-3H9 | 3.36E−07 |
| HY2-A12 | 1.50E−06 |
| HY2-B6 | 5.36E−07 |
| Immunized Serum | 3.86E−07 |
| Commercial mAb* | 4.10E−05 |

*Clone B892M, mouse IgG1 from ascites;
Catalog# MBS312891

TABLE 2A

| | | | Heavy Chain | | | |
|---|---|---|---|---|---|---|
| Clone | CDR1 | SEQ ID NO: | CDR2 | SEQ ID NO: | CDR3 | SEQ ID NO: |
| HY1-1D10 | GYNFSDYYIN | 27 | WIGEIYPGSGTTYY | 34 | AGGSSLYVW.....FAY | 43 |
| HY1-1F12 | VYTFSSHWIE | 28 | WIGEILPGSGSTNY | 35 | ARYE........YGNYV | 44 |
| HY1-3B1 | DHTFTDYYIN | 29 | WIGEIYPGSGYTYY | 36 | ARGDGYYFW.....FGY | 45 |
| HY1-3C10 | DHTFTDYYIN | 29 | WIGEIYPGSGYTYY | 36 | ARGDGYYFW.....FGY | 45 |
| HY1-3E3 | YTFSNYWIE | 30 | WIGEILPGSGSTYH | 37 | ATGSRLA.W.....FVY | 46 |
| HY1-3G4 | YTFSNYWIE | 30 | WIGEILPGSGSTYH | 37 | ATGSRLA.W.....FVY | 46 |
| HY1-3G8 | FDFSRYWMS | 1 | WIGEINPDSSTINY | 2 | SRVLLYYGSNPHWHFDV | 3 |
| HY1-3H5 | YTFTSQWMQ | 23 | WIGEINPSSGRTHY | 38 | ARGDGDYVW.....FAY | 47 |
| HY1-3H7 | YTFTSQWMQ | 23 | WIGEINPSSGRTHY | 38 | ARGDGDYVW.....FAY | 47 |
| HY1-3H9 | YTFTSQWMQ | 23 | WIGEINPSSGRTHY | 38 | ARGDGDYVW.....FAY | 47 |
| HY2-A6 | ATQSRSYWIE | 31 | WIGEILPGSGSTTY | 39 | ARARTGTNYYT...MDY | 48 |
| HY2-A8 | YTISSY.WIE | 32 | WIGEILPGSGSTTY | 39 | ARARTGTNYYT...MDY | 48 |
| HY2-A10 | | | | | | |
| HY2-A12 | GYTSTDYYIN | 4 | WIGEIYPGSGNTYY | 5 | TRGGVYYGYDDAW.FVY | 6 |
| HY2-B2 | YSITSDYAWN | 33 | WMGYIGYSGGTSY | 40 | AREITTTGC.....FAY | 49 |
| HY2-B5 | YTISSY.WIE | 32 | WIGEILPGSGSTTY | 39 | ARARTGTNYYT    MDY | 48 |
| HY2-B6 | | | | | | |
| HY2-B9 | YTFTSQWMQ | 23 | WIGEINPSSGRTHY | 38 | ARGDGDYVW.....FAY | 47 |
| HY2-B10 | YTFTSQWMQ | 23 | WIGEINPSSGRTHY | 38 | ARGDGDYVW.....FAY | 47 |
| HY2-C6 | | | WLGYISYSGTTSY | 41 | AREVTTTGW.....FVY | 50 |
| HY2-C7 | FDFSRYWMS | 1 | WIGEVNPDSSTINS | 42 | ARLYYNYVDYYYA.MDY | 51 |
| HY2-D1 | | | WLGYISYSGTTSY | 41 | AREVTTTGW.....FVY | 50 |

TABLE 2B

| | | Light Chain | | | | | |
|---|---|---|---|---|---|---|---|
| Clone | Light Chain | CDR1 | SEQ ID NO: | CDR2 | SEQ ID NO: | CDR3 | SEQ ID NO: |
| HY1-1D10 | 1D10 | YRASKSVSTSGYSYMH | 7 | LLIYLVSNLES | 10 | QHIRELTR | 11 |
| HY1-1F12 | 1F12 | | | | | | |
| HY1-3B1 | 3B1 | YRASKSVSTSGYSYMH | 7 | LLIYLVSNLES | 10 | | |
| HY1-3C10 | 3C10 | | | | | | |
| HY1-3E3 | 3E3 | YRASKSVSTSGYSYMH | 7 | LLIYLVSNLES | 10 | QHIRELTR | 11 |
| HY1-3G4 | 3G4 | YRASKSVSTSGYSYMH | 7 | LLIYLVSNLES | 10 | QHIRELTR | 11 |
| HY1-3G8 | 3G8 | YRASKSVSTSGYSYMH | 7 | LLIYAASNLES | 8 | QHIRELT | 9 |
| HY1-3H5 | 3H5 | YRASKSVSTSGYSYMH | 7 | LLIYLVSNLES | 10 | QHIRELTR | 11 |
| HY1-3H7 | 3H7 | | | | | | |
| HY1-3H9 | 3H9 | | | | | | |
| HY2-A6 | A6 | | | | | | |
| HY2-A8 | A8 | ........RSSVSYMY | 52 | LLIYDTSNLDS | 54 | QHIREFTR | 58 |
| HY2-A10 | A10 | | | | | | |
| HY2-A12 | A12 | YRASKSVSTSGYSYMH | 7 | LLIYLVSNLES | 10 | QHIRELTR | 11 |
| HY2-B2 | B2 | YRASKSVSTSGKSYMH | 53 | SYMLYPTSNV | 55 | | |
| HY2-B5 | B5 | YRASKSVSTSGYSYMH | 7 | LLIYLVSNLES | 10 | HHIRELTR | 59 |
| HY2-B6 | B6 | YRASKSVSTSGYSYMH | 7 | LFIYLVSNLES | 56 | | |
| HY2-B9 | B9 | YRASKSVSTSGYSYMH | 7 | LLIYLVSNLES | 10 | HRSLGSLR | 60 |
| HY2-B10 | B10 | | | LVIYDTSNLAS | 57 | QHIREFTR | 58 |
| HY2-C6 | C6 | | | | | | |
| HY2-C7 | C7 | YRASKSVSTSGYSYMH | 7 | LLIYLVSNLES | 10 | HHIRELTS | 61 |
| HY2-D1 | D1 | | | | | | |

TABLE 3A

| | Heavy Chain | SEQ ID NO: |
|---|---|---|
| 1D10 | AGGCTGTCTAGGCTACAACTTCAGTGACTACTATATAAACTGGGTGAAGCAGAGGACTGG ACAGGGCCTTGAGTGGATTGGAGAGATTTATCCTGGAAGTGGTACTACTTACTACAATGA GAAGTTCAAGGGCAAGGCCACACTGACTGCAGACAAATCCTCCAGCACAGCCTACATGCA GCTCAGCAGCCTGACATCTGAGGACTCTACAGTCTATTTCTGTGCAGGAGGCAGTAGTCT CTACGTCTGGTTTGCTTACTGGGGCCAAGGGACTCTGGTCACTGTCTCTGCAGCCAAAAC GACACCCCCATCTGTCTATCCACTGGCCCCTGGATCTGCTGCCCAAACTAACTCCATGGT GACCCTGGGATGCCTGGTCAAGGGCTATTTCCCTGAGCCAGTGACAGTGACCTGGAACTC TGGATCCCTGTCCAGCGGTGTG | 62 |
| 1F12 | ATGAAGGTATCCTGCAAGGCTACTGTCTACACATTCAGTAGTCACTGGATAGAGTGGATA AAGCAGAGGCCTGGACATGGCCTTGAGTGGATTGGAGAGATTTTACCTGGAAGTGGTAGT ACTAACTACAATGAGAAGTTCAAGGGCAAGGCCACATTCACTGCAGATACATCCTCCAAC GTGGCCTACATGCAACTCACCAGCCTGACATCTGAGGACTCTGCCGTCTATTACTGTGCA AGATATGAATATGGTAACTACGTCTGGGGCCAAGGGACTCTGGTCACTGTCTCTGCTGCC AAAACGACACCCCCATCTGTCTATCCACTGGCCCCTGGATCTGCTGCCCAAACTAACTCC ATGGTGACCCTGGGATGCCTGGTCAAGGGCTATTTCCCTGAGCCAGTGACAGTGACCTGG AACTCTGGATCCCTGTCCAGCGGTGTGCACA | 63 |
| 3B1 | ACTGTCCTGCAAGGCTTCTGATCACACCTTCACTGACTACTATATAAATTGGATGAAGCA GAGGACTGGACAGGGCCTTGAGTGGATTGGAGAGATTTATCCTGGAAGTGGTTATACTTA CTACAATGAGAAGTTCAAGGGCAAGGCCACACTGACTGCAGACAAATCCTCCAGCACAGC CTACATGCAGCTCAGCAGCCTGACATCTGAGGACTCTGCAGTCTATTTCTGTGCAAGAGG TGATGGTTACTACTTCTGGTTTGGTTACTGGGGCCAAGGGACTCTGGTCACTGTCTCTGC | 64 |

TABLE 3A-continued

| | Heavy Chain | SEQ ID NO: |
|---|---|---|
| | AGCCAAAACGACACCCCCATCTGTCTATCCACTGGCCCCTGGATCTGCTGCCCAAACTAA<br>CTCCATGGTGACCCTGGGATGCCTGGTCAAGGGCTATTTCACTGAGCCAGTGACAGTGAC<br>C | |
| 3C10 | AAACTGTCCTGCAAGGCTTCTGATCACACCTTCACTGACTACTATATAAATTGGATGAAG<br>CAGAGGACTGGACAGGGCCTTGAGTGGATTGGAGAGATTTATCCTGGAAGTGGTTATACT<br>TACTACAATGAGAAGTTCAAGGGCAAGGCCACACTGACTGCAGACAAATCCTCCAGCACA<br>GCCTACATGCAGCTCAGCAGCCTGACATCTGAGGACTCTGCAGTCTATTTCTGTGCAAGA<br>GGTGATGGTTACTACTTCTGGTTTGGTTACTGGGGCCAAGGGACTCTGGTCACTGTCTCT<br>GCAGCCAAAACGACACCCCCATCTGTCTATCCACTGGCCCCTGGATCTGCTGCCCAAACT<br>AACTCCATGGTGACCCTGGGATGCCTGGTCAAGGGCTATTTCCCTGAGCCAGTGACAGTG<br>ACCTGGAACTCTGGATCCCTGTCCAGCGGTGTGCA | 65 |
| 3E3 | ATATGATCAGTGTCCTCTCCAAAGTCCTTGAACATAGACTCTAACCATGGAATGGACCTGG<br>GTCTTTCTCTTCCTCCTGTCAGTAACTGCAGGTGTCCACTCCCAGGTTCAGCTGCAGCAGT<br>CTGGAGCTGAGCTGATGAAGCCTGGGGCCTCAGTGAAGATATCCTGCAAGGCTACTGGCTA<br>CACATTCAGTAACTACTGGATAGAGTGGGTAAAACAGAGGCCTGGACATGGCCTTGAGTGG<br>ATTGGAGAGATTTTACCTGGAAGTGGTAGTACTTACCACAATGAGAATTTCAAGGGCAAGG<br>CCACATTCACTGCAGATACATCCTCCAACACAGCCTATATGCAATTGACTCACCCTGACATC<br>TGAGGACTCTGCCGTCTATTACTGTGCAACCGGTAGTCGCCTCGCCTGGTTTGTTTACTGG<br>GGCCAAGGGACTCTGGTCAATGTCTCTGCAGCCAAAACGACACCCCCATCTGTCTATCCAC<br>TGGCCCCTGGATCTGCTGCCCAAACTAACTCCATGGTGACCCTGGGATGCCTGGTCAAGGG<br>CTATTTCCCTGAGCCAGTGACAGTGACCTGGAACTCTGGATCCCTGTCCCGCGGTGTGCA | 66 |
| 3G4 | TGAAGATATCCTGCAAGGCTACTGGCTACACATTCAGTAACTACTGGATAGAGTGGGTAA<br>AACAGAGGCCTGGACATGGCCTTGAGTGGATTGGAGAGATTTTACCTGGAAGTGGTAGTA<br>CTTACCACAATGAGAATTTCAAGGGCAAGGCCACATTCACTGCAGATACATCCTCCAACA<br>CAGCCTATATGCAATTGATCACCCTGACATCTGAGGACTCTGCCGTCTATTACTGTGCAA<br>CCGGTAGTCGCCTCGCCTGGTTTGTTTACTGGGGCCAAGGGACTCTGGTCAATGTCTCTG<br>CAGCCAAAACGACACCCCCATCTGTCTATCCACTGGCCCCTGGATCTGCTGCCCAAACTA<br>ACTCCATGGTGACCCTGGGATGCCTGGTCAAGGGCTATTTCCCTGAGCCAGTGACAGTGA<br>CCTGGAACTCTGGATCCCTGTGG | 67 |
| 3G8 | AAGCAAAGGGGATCAGCCCGAGATTCTCATTCAGTGATCAACACTGAACACACATCCCTT<br>ATCATGGATTTTGGGCTGATTTTTTTTTATTGTTGCTCTTTTAAAAGGGGTCCAGTGTGAG<br>GTGAAGCTTCTCGAGTCTGGAGGTGGCCTGGTGCAGCCTGGAGGGATCCCTGAAACTCTCC<br>TGTGCAGCCTCAGGATTCGATTTTAGTAGATACTGGATGAGTTGGGTCCGGCAGGCTCCA<br>GGGAAAGGGCTAGAATGGATTGGAGAAATTAATCCAGATAGCAGTACGATAAACTATACG<br>CCATCTCTAAAGGATAAATTCATCATCTCCAGAGACAACGCCAAAAATACGCTGTACCTG<br>CAAATGAGCAAAAGTGAGATCTGAGGACACAGCCCTTTATTACTGTTCAAGAGTCCTCCTT<br>TACTACGGTAGTAACCCCCACTGGCACTTCGATGTCTGGGGCGCAGGGACCACGGTCACC<br>GTCTCCTCAGCCAAAACGACACCCCCATCTGTCTATCCACTGGCCCCTGGATCTGCTGCC<br>CAAACTAACTCCATGGTGACCCTGGGATGCCTGGTCAAGGGCTATTTCCCTGAGCCAGTG<br>ACAGTGACCTGGAACTCTGGATCCCTGTCCAGCGGTGTGACCACCCTTCC | 68 |
| 3H5 | GGACAAGGCCTTGAGTGGATTGGAGAGATTAATCCTAGCAGCGGTCGTACTCACTACAAT<br>GAGAAGTTCAAGACCAAGGCCACACTGACTGTAGACAAATCCTCCAGCACAGCCTACATG<br>CAACTCAGCAGCCTGACATCTGAGGACTCTGCGGTCTATTACTGTGCAAGAGGGGATGGT<br>GACTACGTCTGGTTTGCTTACTGGGGCCAAGGGACTCTGGTCACTGTCTCTGCAGCCAAA<br>ACGACACCCCCATCTGTCTATCCACTGGCCCCTGGATCTGCTGCCCAAACTAACTCCATG<br>GTGACCCTGGGATGCCTGGTCAAGGGCTATTTCCCTGAGCCAGTGACAGTGACCTGGAAC<br>TCTGGATCCCTGTCCAGCGGTGTGCACACCTTCC | 69 |
| 3H7 | TGGGGCTTCAGTGAAGCTGTCCTGCAAGGCTTCTGGCTACACCTTCACCAGCCAATGGAT<br>GCAGTGGGTGAGGCAGAGGCCTGGACAAGGCCTTGAGTGGATTGGAGAGATTAATCCTAG<br>CAGCGGTCGTACTCACTACAATGAGAAGTTCAAGACCAAGGCCACACTGACTGTAGACAA<br>ATCCTCCAGCACAGCCTACATGCAACTCAGCAGCCTGACATCTGAGGACTCTGCGGTCTA<br>TTACTGTGCAAGAGGGGATGGTGACTACGTCTGGTTTGCTTACTGGGGCCAAGGGACTCT<br>GGTCACTGTCTCTGCAGCCAAAACGACACCCCCATCTGTCTATCCACTGGCCCCTGGATC<br>TGCTGCCCAAACTAACTCCATGGTGACCCTGGGATGCCTGGTCAAGGGCTATTTCCCTGA<br>GCCAGTGACAGTGACCTGGAACTCTGGATCCCTGTCCAGCGGTGTGCACACCTTCC | 70 |
| 3H9 | GACAAGGCCTTGAGTGGATTGGAGAGATTAATCCTAGCAGCGGTCGTACTCACTACAATG<br>AGAAGTTCAAGACCAAGGCCACACTGACTGTAGACAAATCCTCCAGCACAGCCTACATGC<br>AACTCAGCAGCCTGACATCTGAGGACTCTGCGGTCTATTACTGTGCAAGAGGGGATGGTG<br>ACTACGTCTGGTTTGCTTACTGGGGCCAAGGGACTCTGGTCACTGTCTCTGCAGCCAAAA<br>CGACACCCCCATCTGTCTATCCACTGGCCCCTGGATCTGCTGCCCAAACTAACTCCATGG<br>TGACCCTGGGATGCCTGGTCAAGGGCTATTTCCCTGAGCCAGTGACAGTGACCTGGAACT<br>CTGGATCCCTGTCCAGCGGTGTGCACACCTTC | 71 |
| A6 | TGAAGATATCCTGCGAGGCTACTGGCTACACAATCAGTAGCTACTGGATAGAGTGGGTAA<br>AGCAGAGGCCTGGACATGGCCTTGAGTGGATTGGAGAGATTTTACCTGGAAGTGGTAGTA<br>CTACCTACAATGAAAAGTTCAAGGGCAAGGCCACATTCACTGCAGATACATCCTCCAACA<br>CAGCCTACATGCAACTCAGCAGCCTGACATCTGAGGACTCTGCCGCCTATTACTGTGCAA<br>GGGCACGCACTGGGACCAATTACTATACTATGGACTACTGGGGTCAAGGAACTCAGTCA<br>CCGTCTCCTCAGCCAAAACGACACCCCCATCTGTCTATCCACTGGCCCCTGGATCTGCTG<br>CCCAAACTAACTCCATGGTGACCCTGGGATGCCTGGTCAAGGGCTATTTCCCTGAGCCAG<br>TGACAGTGACCTGGAACTCTGGATCC | 72 |

TABLE 3A-continued

| Heavy Chain | | SEQ ID NO: |
|---|---|---|
| A8 | AGATATCCTGCGAGGCTACTGGCTACACAATCAGTAGCTACTGGATAGAGTGGGTAAAGC AGAGGCCTGGACATGGCCTTGAGTGGATTGGAGAGATTTTACCTGGAAGTGGTAGTACTA CCTACAATGAAAAGTTCAAGGGCAAGGCCACATTCACTGCAGATACATCCTCCAACACAG CCTACATGCAACTCAGCAGCCTGACATCTGAGGACTCTGCCGCCTATTACTGTGCAAGGG CACGCACTGGGACCAATTACTATACTATGGACTACTGGGGTCAAGGAACCTCAGTCACCG TCTCCTCAGCCAAAACGACACCCCATCTGTCTATCCACTGGCCCCTGGATCTGCTGCCC AAACTAACTCCATGGTGACCCTGGGATGCCTGGTCAAGGGCTATTTCCCTGAGCCAGTGA CAGTGACCTGGAACTCTGGATCCCTGTCCAGCGGTGTG | 73 |
| A10 | | |
| A12 | CTGTCCTGCAAGGCTTCTGGCTACAACTCCACTGACTACTATATAAACTGGGTGAAGCAG AGGACTGGACAGGGCCTTGAGTGGATTGGAGAGATTTATCCTGGAAGTGGTAATACTTAT TACAATGAGAAGTTCAAGGGCAAGGCCACACTGACTGCAGACAAATCCTCCAGCACAGCC TACATGCAGCTCAGCAGCCTGACATCTGAGGACTCTGCAGTCTATTTCTGTACAAGAGGG GGGGTCTACTATGGTTACGACGATGCCTGGTTTGTTTACTGGGGCCAAGGGACTCTGGTC ACTGTCTCTGCAGCCAAAACAACAGCCCCATCGGTCTATCCACTGGCCCCTGTGTGTGG | 74 |
| B2 | CATGGGCTGACTGAGCTTCTCAGTCTCTGTCCCTCACCTGCACTGTCACTGAGCTACTCA ATCACCAGTGATTATGCCTGGAACTGGATCCGGCAGTTTCCAGGGAAACAAACTGGAGTGG ATGGGCTACATAGGCTACAGTGGTGGCACTAGCTACAACCCATCTCTCAAAAGTCGAATC TCTATCACTCGAGACACATCCAAGAACCAGTTCTTCCTGCACTTGAATTCTGTGACTACT GAGGACACAGCCACATATTTCTGTGCAAGAGAGATTACGACGACGGGGTGCTTTGCTTAC TGGGGCCAAGGGACTCTGGTCACTGTCTCTGCAGCCAAAACGACACCCCATCTGTCTAT CCACTGGCCCCTGGATCTGCTGCCCAAACTAACTCCATGGTGACCCTGGGATGCCTGGTC AAGGGCTATTTCCCTGAGCCAGTGACAGTGACCTGGAACTCTGGATCC | 75 |
| B5 | GATATCCTGCGAGGCTACTGGCTACACAATCAGTAGCTACTGGATAGAGTGGGTAAAGCA GAGGCCTGGACATGGCCTTGAGTGGATTGGAGAGATTTTACCTGGAAGTGGTAGTACTAC CTACAATGAAAAGTTCAAGGGCAAGGCCACATTCACTGCAGATACATCCTCCAACACAGC CTACATGCAACTCAGCAGCCTGACATCTGAGGACTCTGCCGCCTATTACTGTGCAAGGGC ACGCACTGGGACCAATTACTATACTATGGACTACTGGGGTCAAGGAACCTCAGTCACCGT CTCCTCAGCCAAAACGACACCCCATCTGTCTATCCACTGGCCCCTGGATCTGCTGCCCA AACTAACTCCATGGTGACCCTGGGATGCCTGGTCAAGGGCTATTTCCCTGAGCCAGTGAC AGTGACCTGGAACTCTGGATCCCTGTCCAGCGGTGTGA | 76 |
| B6 | | |
| B9 | GACAAGGCCTTGAGTGGATTGGAGAGATTAATCCTAGCAGCGGTCGTACTCACTACAATG AGAAGTTCAAGACCAAGGCCACACTGACTGTAGACAAATCCTCCAGCACAGCCTACATGC AACTCAGCAGCCTGACATCTGAGGACTCTGCGGTCTATTACTGTGCAAGAGGGGATGGTG ACTACGTCTGGTTTGCTTACTGGGGCCAAGGGACTCTGGTCACTGTCTCTGCAGCCAAAA CGACACCCCATCTGTCTATCCACTGGCCCCTGGATCTGCTGCCCAAACTAACTCCATGG TGACCCTGGGATGCCTGGTCAAGGGCTATTTCCCTGAGCCAGTGACAGTGACCTGGAACT CTGGATCCCTGTCCAGCGGTGTGCA | 77 |
| B10 | GGACAAGGCCTTGAGTGGATTGGAGAGATTAATCCTAGCAGCGGTCGTACTCACTACAAT GAGAAGTTCAAGACCAAGGCCACACTGACTGTAGACAAATCCTCCAGCACAGCCTACATG CAACTCAGCAGCCTGACATCTGAGGACTCTGCGGTCTATTACTGTGCAAGAGGGGATGGT GACTACGTCTGGTTTGCTTACTGGGGCCAAGGGACTCTGGTCACTGTCTCTGCAGCCAAA ACGACACCCCATCTGTCTATCCACTGGCCCCTGGATCTGCTGCCCAAACTAACTCCATG GTGACCCTGGGATGCCTGGTCAAGGGCTATTTCCCTGAGCCAGTGACAGTGACCTGGAAC TCTGGATCCCTGTCCAGCGGTGTG | 78 |
| C6 | GGAACTGGATCCGGGAGATTTCCAGGAAACAAACTGGAGTGGTTGGGCTACATAAGCTAC AGTGGTACCACTAGCTACAACCCATCTCTCAAAAGTCGAATCTCTATCACTCGAGACACA TCCAAGAACCAGTCCTTCCTGCAGTTGAATTCTGTGACTACTGAGGACACAGCCACATAT TACTGTGCAAGAGAGGTTACGACGACGGGGTGGTTTGTTTACTGGGGCCAAGGGACTCTG GTCACTGTCTCTGCAGCCAAAACGACACCCC | 79 |
| C7 | CTCTCCTGTGCAGCCTCAGGATTCGATTTTAGTAGATACTGGATGAGTTGGGTCCGGCAG GCTCCAGGGAAAGGGCTAGAATGGATTGGAGAAGTTAATCCAGATAGCAGTACGATAAAC TCTACGCCATCTCTAAAGGATAAATTCTTCATCTCCAGAGACAACGCCAAAAATACGCTG TACCTGCAGATGATCAAAGTGAGATCTGAGGACACAGCCCTTTATTACTGTGCAAGACTC TACTATAATTACGTCGATTATTACTATGCTATGGACTACTGGGGTCAAGGAACCTCAGTC ACCGTCTCCTCAGCCAAAACGACACCCCATCTGTCTATCCACTGGCCCCTGGATCTGCT GCCCAAACTAACTCCATGGTGACCCTGGGATGCCTGGTCAAGGGCTATTTCCCTGAGCCA GTGACAGTGACCTGGAACTCTGGATCCCTGTCCAGCGGT | 80 |
| D1 | TGATTATGCCTGGAACTGGATCCGGCAGTTTCCAGGGAAACAAACTGGAGTGGTTGGGCTA CATAAGCTACAGTGGTACCACTAGCTACAACCCATCTCTCAAAAGTCGAATCTCTATCAC TCGAGACACATCCAAGAACCAGTCCTTCCTGCAGTTGAATTCTGTGACTACTGAGGACAC AGCCACATATTACTGTGCAAGAGAGGTTACGACGACGGGGTGGTTTGTTTACTGGGGCCA AGGGACTCTGGTCACTGTCTCTGCAGCCAAAACGACACCCCATCTGTCTATCC | 81 |

TABLE 3B

| | Light Chain (reverse complement) | SEQ ID NO: |
|---|---|---|
| 1D10 | ACGTGTAAGCTCCCTAATGTGCTGACAGTAATAGGTTGCAGCATCCTCCTCCTCCACAGG<br>ATGGATGTTGAGGGTGAAGTCTGTCCCAGACCCACTGCCACTGAACCTGGCAGGGACCCC<br>AGATTCTAGGTTGGATACAAGATAGATGAGGAGTCTGGGTGGCTGTCCTGGTTTCTGTTG<br>GTTCCAGTGCATATAACTATAGCCAGATGTACTGACACTTTTGCTGGCCCTGTATGAGAT<br>GGTGGCCCTCTGCCCCAGAGATACAGCTAAGGAAGCAGGAGACTGTGTCAGCACAATGTC<br>ACCAGTGGAACCTGGAACCCAGA | 82 |
| 1F12 | | |
| 3B1 | TTATTCCTCCCATGATTGGGGGTCATTTGTCTTGAAGGGCCTTTCTCCATTTAAATTTAT<br>GGTCCTTCCAGTCTCTTGTTGATCTTCAAATGTTTGTCTTCACATAGAAATAGAGTCCTG<br>TGTCCGCTGCATTTGGATTACCATCACCAATCTGAAATATACTTGTTACCCATGTAATGA<br>TAAGTTTGTGGGTTGGG | 83 |
| 3C10 | | |
| 3E3 | TAACTGCTCACTGGATGGTGGGAAGATGGATACAGTTGGTGCAGCATCAGCCCGTTTTAT<br>TTCCAGCTTGGTCCCCCCTCCGAACGTGTAAGCTCCCTAATGTGCTGACAGTAATAGGTT<br>GCAGCATCCTCCTCCTCCACAGGATGGATGTTGAGGGTGAAGTCTGTCCCAGACCCACTG<br>CCACTGAACCTGGCAGGGACCCCAGATTCTAGGTTGGATACAAGATAGATGAGGAGTCTG<br>GGTGGCTGTCCTGGTTTCTGTTGGTTCCAGTGCATATAACTATAGCCAGATGTACTGACA<br>CTTTTGCTGGCCCTGTATGAGATGGTGGCCCTCTGCCCCAGAGATACAGCTAAGGAAGCA<br>GGAGACTGTGTCAGCACAATGTCACCAGTGGAACCTGGAACCCAGAGCAGCAGTACCCAT<br>AACAGGAGTGTGTCTGTCTCCATCTCTGAGAGCTGGAAGAGAG | 84 |
| 3G4 | CTTGGTCCCCCCTCCGAACGTGTAAGCTCCCTAATGTGCTGACAGTAATAGGTTGCAGCA<br>TCCTCCTCCTCCACAGGATGGATGTTGAGGGTGAAGTCTGTCCCAGACCCACTGCCACTG<br>AACCTGGCAGGGACCCCAGATTCTAGGTTGGATACAAGATAGATGAGGAGTCTGGGTGGC<br>TGTCCTGGTTTCTGTTGGTTCCAGTGCATATAACTATAGCCAGATGTACTGACACTTTTG<br>CTGGCCCTGTATGAGATGGTGGCCCTCTGCCCCAGAGATACAGCTAAGGAAGCAGGAGAC<br>TGTGTCAGCACAATGTCACCAGTGGAACCTGGAACCCAGAGCAGCAGCA | 85 |
| 3G8 | GATTATGATGGTGATCGTTATATGAACTGGTACCAGCAGAAACCAGGACAGCCACCCAAA<br>CTCCTCATCTATGCTGCATCCAATCTAGAATCTGGGATCCCTGCCAGGTTTAGTGGCAGT<br>GGGTCTGGGACAGACTTCACCCTCAACATCCATCCTGTGGAGGAGGAGGATGCTGCAACC<br>TATTACTGTCAGCACATTA | 86 |
| 3H5 | GACAGTAATAGGTTGCAGCATCCTCCTCCTCCACAGGATGGATGTTGAGGGTGAAGTCTG<br>TCCCAGACCCACTGCCACTGAACCTGGCAGGGACCCCAGATTCTAGGTTGGATACAAGAT<br>AGATGAGGAGTCTGGGTGGCTGTCCTGGTTTCTGTTGGTTCCAGTGCATATAACTATAGC<br>CAGATGTACTGACACTTTTGCTGGCCCTGTATGAGATGGTGGCCCTCTGCCCCAGAGATA<br>CAGCTAAGGAAGCAGGAGACTGTGTCAGCACAATGTCACCAGTGGAACCTGGAACCCAGA<br>GCAGCAGCAC | 87 |
| 3H7 | | |
| 3H9 | | |
| A6 | | |
| A8 | AACTCCCTAATGTGCTGACAGTAATAGGTTGCAGCATCCTCCTCCTCCACAGGATGGATG<br>TTGAGGGTGAAGTATGTCCCAGACCCACTGCCACTGAACCTGGCAGGGACCCCAGAATCC<br>AGGTTGGATGTGTCATAAATCAGGAGTCTGGGGGAGGATCCTGGCTTCTGCTGGTACCAG<br>TACATGTAACTTACACTTGATCTGGCACTGCAGGTCATGGTGACCTTCTCCCCTGGAGAT<br>GC | 88 |
| A10 | | |
| A12 | CATCCTCCTCCTCCACAGGATGGATGTTGAGGGTGAAGTCTGTCCCAGACCCACTGCCAC<br>TGAACCTGGCAGGGACCCCAGATTCTAGGTTGGATACAAGATAGATGAGGAGTCTGGGTG<br>GCTGTCCTGGTTTCTGTTGGTTCCAGTGCATATAACTATAGCCAGATGTACTGACACTTT<br>TGCTGGCCCTGTATGAGATGGTGGCCCTCTGCCCCAGAGATACAGCTAAGGAAGCAGGAG<br>ACTGTGTCAGCACAATGCCATCAGTGGAACCTGGAACCCAGAG | 89 |
| B2 | TGTGTACGTTCCATCTTCTTCCTCCTCCGGGGATGGATGTGAAGGGTGAAGCCCCCCCTA<br>GACCCACTGCACTGAATCGCCAGGGACCCCACATTCGAGGTTGGATACAACATATATGAA<br>CATGTGGGTGGCTGTCCTGGTTTCTGTTGGTTCCCGTGCATATAACTTTTTCCAGATGTA<br>CTGACACTTTTGCTGGCCCTGTATGAGATGGTTTTCATATG | 90 |
| B5 | TGACAGTAATAGGTTGCAGCATCCTCCTCCTCCACAGGATGGATGTTGAGGGTGAAGTCT<br>GTCCCAGACCCACTGCCACTGAACCTGGCAGGGACCCCAGATTCTAGGTTGGATACAAGA<br>TAGATGAGGAGTCTGGGTGGCTGTCCTGGTTTCTGTTGGTTCCAGTGCATATAACTATAG<br>CCAGATGTACTGACACTTTTGCTGGCCCTGTATGAGATGGTGGCCCTCTGCCCCAGAGAT<br>ACAGCTAAGGAAGCAGGAGACTGTGTCAGCACAATGTCACCAGTGGAACCTGGAACCCAG<br>AGCAGCAGC | 91 |
| B6 | CGTGTAAGCTCCCTAATGTGTTGACCGTAATAGGTTGCAGCATCCTCCTCCTCCCAGGAT<br>GGATGTTGAGGGTGAAGTCTGTCCCAAACCCCCTGCCCCTGAACCTGGCAGGGACCCCAG | 92 |

TABLE 3B-continued

| | Light Chain (reverse complement) | SEQ ID NO: |
|---|---|---|
| | ATTCCAGGTTGGATACAAGATAGATGAAGAGTCTGGGTGGCTGTCCTGGTTTCTGTTGGT TCCCGTGCATATAACTATAGCCAGATGTACTGACACTTTTGCTGGCCCTGTATGAGATGG TGG | |
| B9 | GCAGCATCCTCCTCCTCCACAGGATGGATGTTGAGGGTGAAGTCTGTCCCAGACCCACTG CCACTGAACCTGGCAGGGACCCCAGATTCTAGGTTGGATACAAGATAGATGAGGAGTCTG GGTGGCTGTCCTGGTTTCTGTTGGTTCCAGTGCATATAACTATAGCCAGATGTACTGACA CTTTTGCTGGCCCTGTATGA | 93 |
| B10 | TATGTCCCAGACCCACTGCCACTGAACCTGACAGGGACCCCAGATTCTAGGTTGGATGCA ACATAAATCATGAGTCTGGGGGACTATCCTGGCTTCTGCTGGTACCAGTAGATGTAACTT ACACTTGAT | 94 |
| C6 | | |
| C7 | TGACAGTAATAGGTTGCAGCATCCTCCTCCTCCACAGGATGGATGTTGAGGGTGAAGTCT GTCCCAGACCCACTGCCACTGAACCTGGCAGGGACCCCAGATTCTAGGTTGGATACAAGA TAGATGAGGAGTCTGGGTGGCTGTCCTGGTTTCTGTTGGTTCCAGTGCATATAACTATAG CCAGATGTACTGACACTTTTGCTGGCCCTGTATGA | 95 |
| D1 | | |

Example 2

This Example describes the development and characterization of anti-heroin, anti-6-acetyl-morphine (6MAM), and anti-morphine monoclonal antibodies. 6MAM and morphine are active metabolites of heroin.

Using the methods described in Example 1 but substituting a morphine-based hapten conjugated to subunit keyhole limpet hemocyanin (sKLH) (referred to herein as MOR-sKLH or M-KLH) with alum adjuvant or CpG adjuvant (CpG ODN-1826, InvivoGen, San Diego, CA) for the OXY-KLH antigen with alum adjuvant (FIG. 1C), mice (n=4) were immunized on days 0 and 28. The morphine-based hapten conjugated to sKLH (MOR-sKLH) is described in Pravetoni et al. *Vaccine.* 2012; 30(31):4617-4624. Hybridoma screening was performed as described in Example 1 but using 5 ng/well M-BSA blocked with 1% gelatin.

Clones generated using MOR-sKLH adsorbed on alum adjuvant are labeled with/include the prefix HY3 or HY-3; clones generated using MOR-sKLH with CpG adjuvant are labeled with/include the prefix HY4 or HY-4.

Using this method, 5 clones expressing high-affinity mAb against heroin, 6-acetyl-morphine, and morphine were generated (Table 5) and were characterized (see FIG. 2B & FIG. 7).

Subclass ELISA was performed to identify clones expressing IgG$_1$, IgG$_{2a}$, or IgG$_3$ antibodies; results are shown in FIG. 2C.

Exemplary protein sequences of the antibodies are shown in FIG. 8A and CDRs of the antibodies are identified in Table 6A-Table 6B.

TABLE 5

| Clone Name | Antibody Name | HY-3 or HY-4 | IgG1 or IgG2a |
|---|---|---|---|
| HY3-1A2 | HY3-1A2 or 1A2 | HY-3 | IgG1 |
| HY3-1E4 | HY3-1E4 or 1E4 | HY-3 | IgG1 |
| HY3-1G4 | HY3-1G4 or 1G4 | HY-3 | IgG1 |
| HY4-1A6 | HY4-1A6 or 1A6 | HY-4 | IgG1 |
| HY4-1F9 | HY4-1F9 or 1F9 | HY-4 | IgG1 |

TABLE 6A

| Heavy Chain | | | | | | | |
|---|---|---|---|---|---|---|---|
| Clone | CDR1 | SEQ ID NO: | CDR2 | SEQ ID NO: | CDR3 | SEQ ID NO: |
| HY3-1A2 | YKFSSYWID | 15 | WIGEILPGSSSSYY | 16 | RWDTYYWYFDV | 17 |
| HY3-1E4 | | | | | | |
| HY3-1G4 | FNIKDYYIH | 12 | WIGWIDPENGDTEYD | 13 | SSTMITTALFAY | 14 |
| HY4-1A6 | | | | | | |
| HY4-1F9 | YKFSSYWID | 15 | WIGEILPGSSSSYY | 16 | RWDTYYWYFDV | 17 |

TABLE 6B

| | | Light Chain | | | | |
|---|---|---|---|---|---|---|
| Clone | CDR1 | SEQ ID NO: | CDR2 | SEQ ID NO: | CDR3 | SEQ ID NO: |
| HY3-1A2 | YRASKSVSTSGYSYMH | 7 | LLIYLVSNLES | 10 | SHIRELTR | 97 |
| HY3-1E4 | YRASKSVSTSGYSYMH | 7 | LLIYLVSNLES | 10 | QHIRELTR | 11 |
| HY3-1G4 | CKASHSVDYDGDRYMN | 18 | LLIYVASNLEC | 19 | QRSNEDPF | 20 |
| HY4-1A6 | CRASQSIGTSTH | 21 | IIIYFESILEF | 96 | QHIREITR | 98 |
| HY4-1F9 | CRASQSIGTSTH | 21 | IIIYFVSNLEF | 22 | QHIRELTR | 11 |

Figures 7A, 7B:
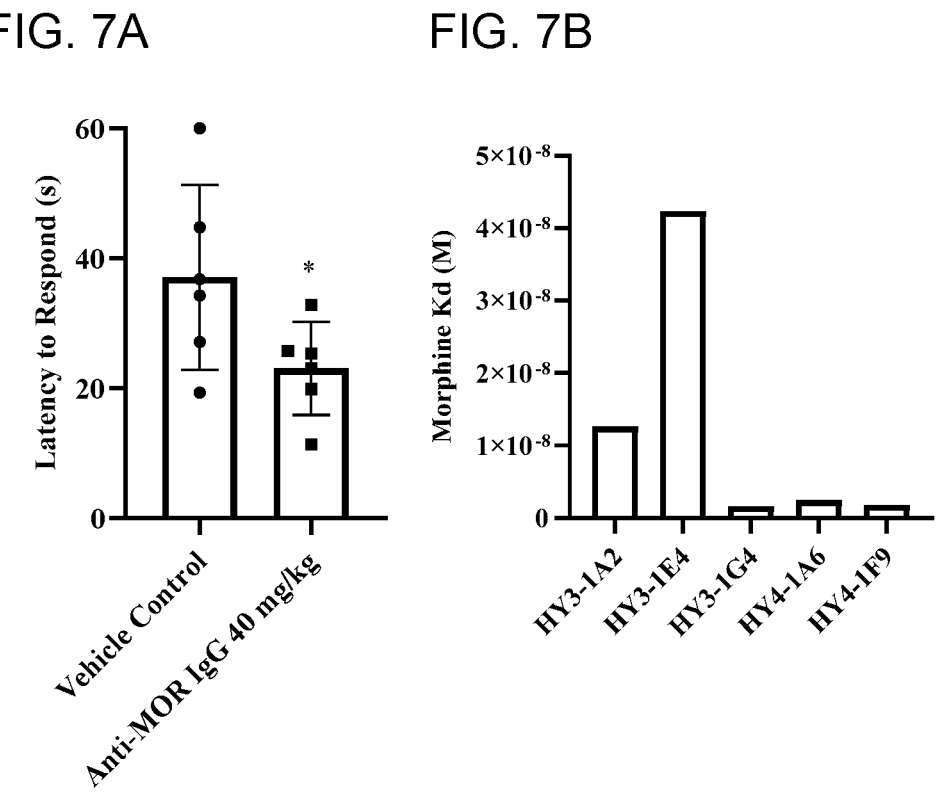
FIG. 7A shows in vivo efficacy of an exemplary mAb (HY4-1F9) against heroin and its metabolites 6-acetyl-morphine and morphine. Mice were passively immunized with 40 mg/kg mAb and were then challenged with 1 mg/kg heroin s.c. Antinociception induced by heroin is shown as latency to respond on a hot plate set to 54° C. (See also FIG. 7C, showing antinociception as percent maximum possible effect (% MPE).)
FIG. 7B shows dissociation constants of anti-morphine mAb as determined by competitive ELISA.
Figure 7C:
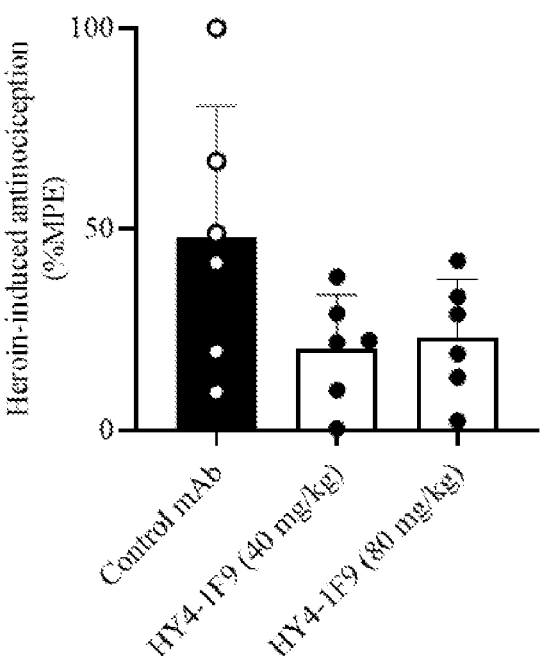
FIG. 7C-FIG. 7E show passive immunization with anti-morphine mAb reduces heroin distribution to the brain. Mice (n=6/group) were passively immunized with 40 mg/kg or 80 mg/kg anti-morphine mAb i.p. After 24 hours, mice were challenged with 1.0 mg/kg heroin s.c., and antinociception was evaluated by latency to respond on a hot plate (FIG. 7C) 30 min post-injection. Heroin metabolites morphine and 6MAM in serum (FIG. 7D) and brain (FIG. 7E) were determined by LC-MS. Mean±SD; p<0.01; **p<0.0001.
Figure 7D:
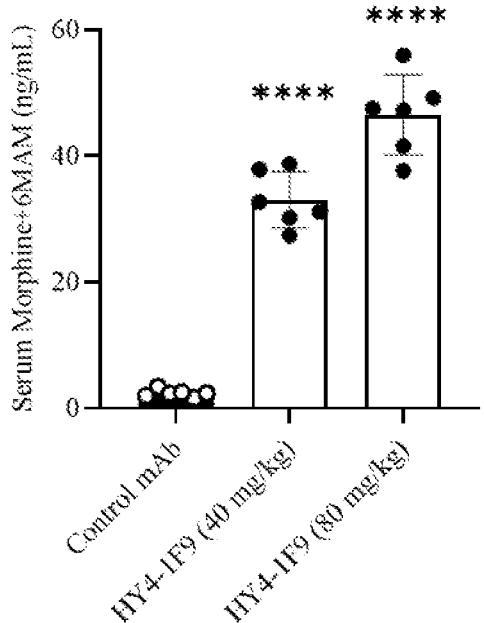
Figure 7E:
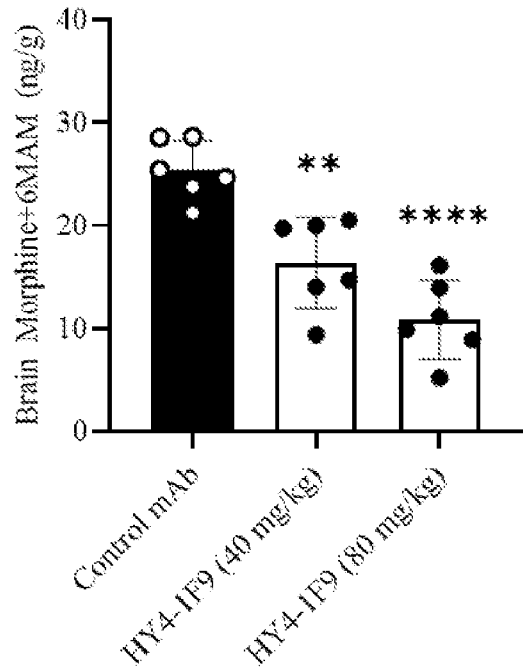

In vivo efficacy of anti-heroin mAb. For a-heroin mAb, relative affinity of purified mAb was evaluated by competitive ELISA using plates coated with M-BSA and free morphine as competitor. Three clones exhibited $IC_{50}$<2 nM (FIG. 7B), and HY4-1F9 was chosen for scale up and in vivo characterization. Mice were passively immunized with purified α-heroin mAb, and given a 1 mg/kg heroin challenge 24 hours after passive immunization. Heroin-induced antinociception was reduced by passive immunization at this dose (FIG. 7C), but the effect was not statistically significant (p=0.086 for 40 mg/kg; p=0.127 for 80 mg/kg). Because heroin is rapidly metabolized in vivo to active metabolites morphine and 6MAM, the concentrations of these metabolites in the brain and serum 30 minutes post-challenge were measured by LC-MS as a correlate of drug distribution. Results are shown in FIG. 7D & FIG. 7E. At a dose of 1 mg/kg heroin, passive immunization with 40 mg/kg a-heroin mAb reduced brain distribution of heroin metabolites by 35%, and 80 mg/kg mAb reduced distribution by 57% of control (FIG. 7E).

To investigate the distribution of a-opioid mAb after passive immunization, 40 mg/kg of the lead α-heroin mAb HY4-1F9 was administered to mice either s.c. or i.p., and blood was sampled at intervals following administration to determine concentration of HY4-1F9 in serum (FIG. 11). Serum mAb concentration was equivalent between these routes, suggesting that both s.c. and i.p. are viable for delivery of mAb and supporting use of the more convenient s.c. delivery for α-opioid prophylaxis in potential clinical applications.

Example 3

This Example describes the development and characterization of anti-fentanyl monoclonal antibodies.

Figure 1D:
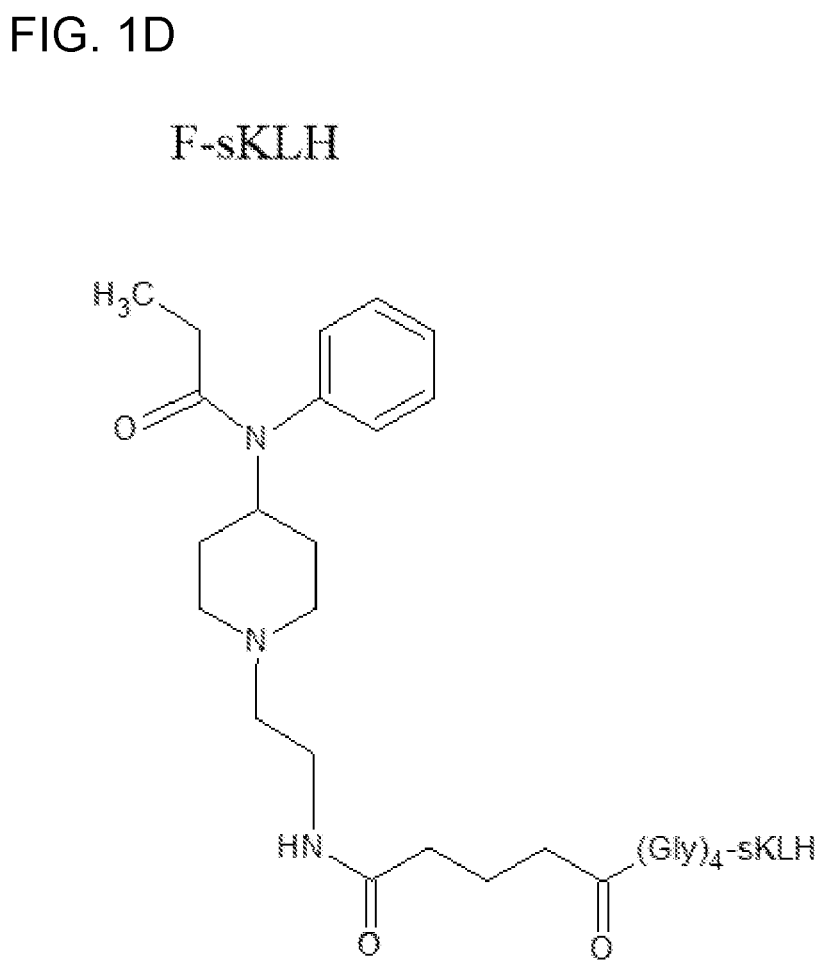

Using the methods described in Example 1 but substituting a fentanyl-based hapten conjugated to sKLH (F-sKLH) with alum adjuvant for the OXY-KLH antigen with alum adjuvant (FIG. 1D), mice (n=4) were immunized on days 0 and 28. The fentanyl-based hapten conjugated to sKLH (F-sKLH) is described in Raleigh et al. *J Pharmacol Exp Ther.* 2019; 368(2):282-291. Hybridoma screening was performed as described in Example 1 but using 5 ng/well F-BSA blocked with 1% gelatin.

An additional fentanyl-based hapten containing a biotin moiety was used for antibody characterization by biolayer interferometry (FIG. 1E). Fen(C)-Acry-COO-NHS was prepared as previously described in Li et al., *RSC Adv.,* 2017, 7:20015. Biotin-PEGS-NH2 (30 mg, 0.05 mmol) and Fen (C)-Acry-COO—NHS (25 mg, 0.05 mmol) were dissolved in 2 mL of dry dichloromethane for 16 hours. The reaction mixture was extracted with water (3 times, 20 mL) and brine (1 time, 10 mL). The organic phase was dried over magnesium sulfate, filtered and evaporated under reduced pressure. Yield was approximately 40 mg. Structure was verified by NMR as follows: M/z 984.3 M+H $^1$H NMR (500 MHz, $CDCl_3$): d 7.57 (d, J=16 Hz, 1H), 7.48-7.32 (m, 5H), 7.18-7.12 (m, 2H), 7.11-7.05 (m, 2H), 6.80-6.63 (br, 3H), 6.48 (d, J=16 Hz, 1H), 5.66-5.50 (br, 2H), 4.92-4.79 (br, 2H), 4.76-4.62 (m, 1H), 4.55-4.45 (m, 2H), 4.35-4.26 (m, 2H), 3.68-3.59 (m, 60H), 3.58-3.52 (m, 8H), 3.46-3.40 (m, 8H), 3.20-3.12 (m, 3H), 3.08-2.96 (br, 2H), 2.95-2.87 (m, 3H), 2.80-2.68 (m, 4H), 2.62-2.50 (br, 2H), 2.28-2.12 (m, 7H), 1.93 (q, J=7.5 Hz, 2H), 1.86-1.60 (m, 44H), 1.51-1.40 (m, 8H), 1.01 (t, J=7.5 Hz, 3H). (Proton counts attributed to resonances from the biotin portion of the molecule overintegrate due to a small amount of unreacted starting material.)

Clones generated using F-sKLH adsorbed on alum adjuvant are labeled with/include the prefix HYS, HY-5, HY6, or HY6.

Subclass ELISA was performed to identify clones expressing $IgG_1$, $IgG_{2a}$, or $IgG_3$ antibodies; results are shown in FIG. 2D.

Using this method, 7 clones expressing high-affinity mAb against fentanyl were generated (Table 7). Exemplary protein sequences of the antibodies are shown in FIG. 8B and CDRs of the antibodies are identified in Table 8A-Table 8B.

TABLE 7

| Clone Name | Antibody Name | HY-5 or HY-6 | IgG1 or IgG2a |
|---|---|---|---|
| HY5-E5 | E5 | HY-5 | IgG1 |
| HY5-H9 | H9 | HY-5 | IgG1 |
| HY6-B5 | B5 | HY-6 | IgG1 |
| HY6-D12 | D12 | HY-6 | IgG1 |
| HY6-F9 | F9 | HY-6 | IgG2a |
| HY6-F11 | F11 | HY-6 | IgG2a |
| HY6-F12 | F12 | HY-6 | IgG2a |

TABLE 8A

Heavy Chain

| Clone | CDR1 | SEQ ID NO: | CDR2 | SEQ ID NO: | CDR3 | SEQ ID NO: |
|---|---|---|---|---|---|---|
| HY5-E5 | | | | | | |
| HY5-H9 | | | | | | |
| HY6-B5 | YAFTSYNIY | 99 | WIGYIDPYNGGTTYN | 100 | SEIYYDYGGRFAY | 102 |
| HY6-D12 | | | | | REEYDYDEGYAMDY | 103 |
| HY6-F9 | YTFTSQWMQ | 23 | WIGEINPSSGRTHYN | 24 | RGDGDYVWFAY | 25 |
| HY6-F11 | | | YMGYI SYSGSTYY | 101 | RYYGDNYVGAMDY | 104 |
| HY6-F12 | | | | | | |

TABLE 8B

Light Chain

| Clone | CDR1 | SEQ ID NO: | CDR2 | SEQ ID NO: | CDR3 | SEQ ID NO: |
|---|---|---|---|---|---|---|
| HY5-E5 | YRASKSVSTSGYSYMH | 7 | LLIYLVSNLES | 10 | | |
| HY5-H9 | YRASKSVSTSGYSYMH | 7 | LLIYLVSNLES | 10 | | |
| HY6-B5 | YRASKSVSTSGYSYMH | 7 | LLIYLVSNLES | 10 | QHIRELTR | 11 |
| HY6-D12 | | | | | | |
| HY6-F9 | YRASKSVSTSGYSYMH | 7 | LLIYLVSNLES | 10 | QHIRELTR | 11 |
| HY6-F11 | | | | | | |
| HY6-F12 | YRASKSVSTSGYSYMH | 7 | LLIYLVSNLES | 10 | | |

In vivo efficacy of anti-fentanyl mAb. Relative affinities of α-fentanyl mAb were measured by biolayer interferometry (FIG. 12A), with the highest affinity mAb HY6-F9 exhibiting a dissociation constant of ~0.5 nM. The two lead mAb selected for scale up included HY6-B5 and HY6-F9, which were $IgG_1$ and $IgG_{2a}$ subtypes respectively (FIG. 2D). To evaluate the efficacy of these mAb, male and female mice were passively immunized with 40 mg/kg of either HY6-B5 or HY6-F9. Because fentanyl-induced respiratory depression is a major contributor to overdose fatalities (Fox et al., *Addiction* 2018; 113:59-66), the effects of fentanyl on respiratory behavior were measured 30 minutes after administration of 0.1 mg/kg fentanyl. Passive immunization with either HY6-B5 or HY6-F9 reduced fentanyl antinociception (FIG. 12B), and HY6-F9 prevented fentanyl-induced suppression of respiration and heart rate (FIG. 12C, FIG. 12D).

Because HY6-F9 was effective in reducing the effects of fentanyl in mice, in vivo efficacy of this mAb was also evaluated in rats. Rats were passively immunized with 60 mg/kg mAb and challenged with 0.1 mg/kg fentanyl, and antinociception and respiratory behavior were measured every 15 minutes for one hour. Anti-fentanyl mAb was effective at reducing antinociception (FIG. 13A) and preventing loss of oxygen saturation and heart rate (FIG. 13B, FIG. 13C) after administration fentanyl.

The complete disclosure of all patents, patent applications, and publications, and electronically available material (including, for instance, nucleotide sequence submissions in, for example, GenBank and RefSeq, and amino acid sequence submissions in, for example, SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A polypeptide comprising:
the amino acid sequence of SEQ ID NO: 101; and
the amino acid sequence of SEQ ID NO:104.

2. A method comprising administering the polypeptide of claim 1 to a subject.

3. The method of claim 2, wherein the subject may be exposed to an opioid, is suspected of being exposed to an opioid, or has been exposed to an opioid.

4. A polypeptide comprising the amino acid sequence of SEQ ID NO:162.

5. A method comprising administering the polypeptide of claim 4 to a subject.

6. The method of claim 5, wherein the subject may be exposed to an opioid, is suspected of being exposed to an opioid, or has been exposed to an opioid.

7. An antibody heavy chain comprising the amino acid sequence of SEQ ID NO:162.

8. The antibody heavy chain of claim 7, wherein the heavy chain is humanized.

9. A method comprising administering the antibody heavy chain of claim 8 to a subject.

10. The method of claim 9, wherein the subject may be exposed to an opioid, is suspected of being exposed to an opioid, or has been exposed to an opioid.

11. A method comprising administering the antibody heavy chain of claim 7 to a subject.

12. The method of claim 11, wherein the subject may be exposed to an opioid, is suspected of being exposed to an opioid, or has been exposed to an opioid.

* * * * *

SEQUENCE LISTING

<160> NUMBER OF SEQ ID NOS: 167

<210> SEQ ID NO 1
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Asp Phe Ser Arg Tyr Trp Met Ser
1               5

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ile Gly Glu Ile Asn Pro Asp Ser Ser Thr Ile Asn Tyr
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Arg Val Leu Leu Tyr Tyr Gly Ser Asn Pro His Trp His Phe Asp
1               5                   10                  15

Val

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Ser Thr Asp Tyr Tyr Ile Asn
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Gly Glu Ile Tyr Pro Gly Ser Gly Asn Thr Tyr Tyr
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

-continued

```
Thr Arg Gly Gly Val Tyr Tyr Gly Tyr Asp Asp Ala Trp Phe Val Tyr
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Arg Ala Ser Lys Ser Val Ser Thr Ser Gly Tyr Ser Tyr Met His
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Leu Ile Tyr Ala Ala Ser Asn Leu Glu Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln His Ile Arg Glu Leu Thr
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Leu Ile Tyr Leu Val Ser Asn Leu Glu Ser
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln His Ile Arg Glu Leu Thr Arg
1               5

<210> SEQ ID NO 12
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Phe Asn Ile Lys Asp Tyr Tyr Ile His
1               5

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ile Gly Trp Ile Asp Pro Glu Asn Gly Asp Thr Glu Tyr Asp
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ser Thr Met Ile Thr Thr Ala Leu Phe Ala Tyr
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Lys Phe Ser Ser Tyr Trp Ile Asp
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Gly Glu Ile Leu Pro Gly Ser Ser Ser Ser Tyr Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Trp Asp Thr Tyr Tyr Trp Tyr Phe Asp Val
1               5                   10
```

-continued

```
<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Lys Ala Ser His Ser Val Asp Tyr Asp Gly Asp Arg Tyr Met Asn
1               5                   10                  15

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Ile Tyr Val Ala Ser Asn Leu Glu Cys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Arg Ser Asn Glu Asp Pro Phe
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Arg Ala Ser Gln Ser Ile Gly Thr Ser Thr His
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Ile Ile Tyr Phe Val Ser Asn Leu Glu Phe
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 23

Tyr Thr Phe Thr Ser Gln Trp Met Gln
1               5

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Ile Gly Glu Ile Asn Pro Ser Ser Gly Arg Thr His Tyr Asn
1               5                   10                  15

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Asp Gly Asp Tyr Val Trp Phe Ala Tyr
1               5                   10

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly
1

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Tyr Asn Phe Ser Asp Tyr Tyr Ile Asn
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Tyr Thr Phe Ser Ser His Trp Ile Glu
1               5                   10

<210> SEQ ID NO 29
<211> LENGTH: 10
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 29

Asp His Thr Phe Thr Asp Tyr Tyr Ile Asn
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Thr Phe Ser Asn Tyr Trp Ile Glu
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Thr Gln Ser Arg Ser Tyr Trp Ile Glu
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Thr Ile Ser Ser Tyr Trp Ile Glu
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Ser Ile Thr Ser Asp Tyr Ala Trp Asn
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Ile Gly Glu Ile Tyr Pro Gly Ser Gly Thr Thr Tyr Tyr
1               5                   10
```

```
<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Gly Glu Ile Leu Pro Gly Ser Gly Ser Thr Asn Tyr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Ile Gly Glu Ile Tyr Pro Gly Ser Gly Tyr Thr Tyr Tyr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Ile Gly Glu Ile Leu Pro Gly Ser Gly Ser Thr Tyr His
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Ile Gly Glu Ile Asn Pro Ser Ser Gly Arg Thr His Tyr
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Ile Gly Glu Ile Leu Pro Gly Ser Gly Ser Thr Thr Tyr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 40

```
Trp Met Gly Tyr Ile Gly Tyr Ser Gly Gly Thr Ser Tyr
1               5                   10
```

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Trp Leu Gly Tyr Ile Ser Tyr Ser Gly Thr Thr Ser Tyr
1               5                   10
```

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Trp Ile Gly Glu Val Asn Pro Asp Ser Ser Thr Ile Asn Ser
1               5                   10
```

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Ala Gly Gly Ser Ser Leu Tyr Val Trp Phe Ala Tyr
1               5                   10
```

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Ala Arg Tyr Glu Tyr Gly Asn Tyr Val
1               5
```

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Ala Arg Gly Asp Gly Tyr Tyr Phe Trp Phe Gly Tyr
1               5                   10
```

<210> SEQ ID NO 46
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Thr Gly Ser Arg Leu Ala Trp Phe Val Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Arg Gly Asp Gly Asp Tyr Val Trp Phe Ala Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Ala Arg Thr Gly Thr Asn Tyr Tyr Thr Met Asp Tyr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Arg Glu Ile Thr Thr Thr Gly Cys Phe Ala Tyr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Arg Glu Val Thr Thr Thr Gly Trp Phe Val Tyr
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg Leu Tyr Tyr Asn Tyr Val Asp Tyr Tyr Tyr Ala Met Asp Tyr
```

-continued

```
1               5                10               15

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Ser Val Ser Tyr Met Tyr
1               5

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Arg Ala Ser Lys Ser Val Ser Thr Ser Gly Lys Ser Tyr Met His
1               5                10               15

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Leu Ile Tyr Asp Thr Ser Asn Leu Asp Ser
1               5                10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Tyr Met Leu Tyr Pro Thr Ser Asn Val
1               5                10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Phe Ile Tyr Leu Val Ser Asn Leu Glu Ser
1               5                10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
```

-continued

```
          peptide

<400> SEQUENCE: 57

Leu Val Ile Tyr Asp Thr Ser Asn Leu Ala Ser
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln His Ile Arg Glu Phe Thr Arg
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His His Ile Arg Glu Leu Thr Arg
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Arg Ser Leu Gly Ser Leu Arg
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

His His Ile Arg Glu Leu Thr Ser
1               5

<210> SEQ ID NO 62
<211> LENGTH: 442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
aggctgtcta ggctacaact tcagtgacta ctatataaac tgggtgaagc agaggactgg      60
acagggcctt gagtggattg agagagattta tcctggaagt ggtactactt actacaatga     120
gaagttcaag ggcaaggcca cactgactgc agacaaatcc tccagcacag cctacatgca     180
```

```
gctcagcagc ctgacatctg aggactctac agtctatttc tgtgcaggag gcagtagtct      240
ctacgtctgg tttgcttact ggggccaagg gactctggtc actgtctctg cagccaaaac      300
gacaccccca tctgtctatc cactggcccc tggatctgct gcccaaacta actccatggt      360
gaccctggga tgcctggtca agggctattt ccctgagcca gtgacagtga cctggaactc      420
tggatccctg tccagcggtg tg      442

<210> SEQ ID NO 63
<211> LENGTH: 451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atgaaggtat cctgcaaggc tactgtctac acattcagta gtcactggat agagtggata       60
aagcagaggc ctggacatgg ccttgagtgg attggagaga ttttacctgg aagtggtagt      120
actaactaca atgagaagtt caagggcaag gccacattca ctgcagatac atcctccaac      180
gtggcctaca tgcaactcac cagcctgaca tctgaggact ctgccgtcta ttactgtgca      240
agatatgaat atggtaacta cgtctggggc caagggactc tggtcactgt ctctgctgcc      300
aaaacgacac ccccatctgt ctatccactg gcccctggat ctgctgccca aactaactcc      360
atggtgaccc tgggatgcct ggtcaagggc tatttccctg agccagtgac agtgacctgg      420
aactctggat ccctgtccag cggtgtgcac a      451

<210> SEQ ID NO 64
<211> LENGTH: 421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
actgtcctgc aaggcttctg atcacacctt cactgactac tatataaatt ggatgaagca       60
gaggactgga cagggccttg agtggattgg agagatttat cctggaagtg gttatactta      120
ctacaatgag aagttcaagg gcaaggccac actgactgca gacaaatcct ccagcacagc      180
ctacatgcag ctcagcagcc tgacatctga ggactctgca gtctatttct gtgcaagagg      240
tgatggttac tacttctggt ttggttactg gggccaaggg actctggtca ctgtctctgc      300
agccaaaacg acaccccat ctgtctatcc actggcccct ggatctgctg cccaaactaa      360
ctccatggtg accctgggat gcctggtcaa gggctatttc actgagccag tgacagtgac      420
c      421

<210> SEQ ID NO 65
<211> LENGTH: 455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
aaactgtcct gcaaggcttc tgatcacacc ttcactgact actatataaa ttggatgaag       60
cagaggactg acagggcct gagtggatt ggagagattt atcctggaag tggttatact      120
```

-continued

```
tactacaatg agaagttcaa gggcaaggcc acactgactg cagacaaatc ctccagcaca        180
gcctacatgc agctcagcag cctgacatct gaggactctg cagtctattt ctgtgcaaga        240
ggtgatggtt actacttctg gtttggttac tggggccaag ggactctggt cactgtctct        300
gcagccaaaa cgacaccccc atctgtctat ccactggccc ctggatctgc tgcccaaact        360
aactccatgg tgaccctggg atgcctggtc aagggctatt ccctgagcc agtgacagtg        420 acctggaact ctggatccct gtccagcggt gtgca                                   455
```

<210> SEQ ID NO 66
<211> LENGTH: 609
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 66

```
atatgatcag tgtcctctcc aaagtccttg aacatagact ctaaccatgg aatggacctg         60
ggtctttctc ttcctcctgt cagtaactgc aggtgtccac tcccaggttc agctgcagca        120
gtctggagct gagctgatga gcctggggc ctcagtgaag atatcctgca aggctactgg        180
ctacacattc agtaactact ggatagagtg ggtaaaacag aggcctggac atggccttga        240
gtggattgga gagattttac ctggaagtgg tagtacttac cacaatgaga atttcaaggg        300
caaggccaca ttcactgcag atacatcctc aacacagcc tatatgcaat tgatcaccct        360
gacatctgag gactctgccg tctattactg tgcaaccggt agtcgcctcg cctggtttgt        420
ttactggggc caagggactc tggtcaatgt ctctgcagcc aaaacgacac ccccatctgt        480
ctatccactg gccctggat ctgctgccca aactaactcc atggtgaccc tgggatgcct        540
ggtcaagggc tatttccctg agccagtgac agtgacctgg aactctggat ccctgtcccg        600
cggtgtgca                                                                609
```

<210> SEQ ID NO 67
<211> LENGTH: 443
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 67

```
tgaagatatc ctgcaaggct actggctaca cattcagtaa ctactggata gagtgggtaa         60
aacagaggcc tggacatggc cttgagtgga ttggagagat tttacctgga agtggtagta        120
cttaccacaa tgagaatttc aagggcaagg ccacattcac tgcagataca tcctccaaca        180
cagcctatat gcaattgatc accctgacat ctgaggactc tgccgtctat tactgtgcaa        240
ccggtagtcg cctcgcctgg tttgtttact ggggccaagg gactctggtc aatgtctctg        300
cagccaaaac gacaccccca tctgtctatc cactggcccc tggatctgct gcccaaacta        360
actccatggt gaccctggga tgcctggtca agggctattt ccctgagcca gtgacagtga        420
cctggaactc tggatccctg tgg                                                443
```

<210> SEQ ID NO 68
<211> LENGTH: 650
<212> TYPE: DNA
<213> ORGANISM: Artificial Sequence
<220> FEATURE:

-continued

<223> OTHER INFORMATION: Description of Artificial Sequence: Synthetic
       polynucleotide

<400> SEQUENCE: 68

```
aagcaaaggg gatcagcccg agattctcat tcagtgatca acactgaaca cacatccctt      60
atcatggatt ttgggctgat ttttttttatt gttgctcttt taaaaggggt ccagtgtgag     120
gtgaagcttc tcgagtctgg aggtggcctg gtgcagcctg gaggatccct gaaactctcc     180
tgtgcagcct caggattcga ttttagtaga tactggatga gttgggtccg gcaggctcca     240
gggaaagggc tagaatggat tggagaaatt aatccagata gcagtacgat aaactatacg     300
ccatctctaa aggataaatt catcatctcc agagacaacg ccaaaaatac gctgtacctg     360
caaatgagaa aagtgagatc tgaggacaca gcccttatt actgttcaag agtcctcctt      420
tactacggta gtaaccccca ctggcacttc gatgtctggg gcgcagggac cacggtcacc     480
gtctcctcag ccaaaacgac accccatct gtctatccac tggcccctgg atctgctgcc      540
caaactaact ccatggtgac cctgggatgc ctggtcaagg gctatttccc tgagccagtg     600
acagtgacct ggaactctgg atccctgtcc agcggtgtga ccacccttcc                650
```

<210> SEQ ID NO 69
<211> LENGTH: 394
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 69

```
ggacaaggcc ttgagtggat tggagagatt aatcctagca gcggtcgtac tcactacaat      60
gagaagttca gaccaaggc cacactgact gtagacaaat cctccagcac agcctacatg      120
caactcagca gcctgacatc tgaggactct gcggtctatt actgtgcaag aggggatggt     180
gactacgtct ggtttgctta ctggggccaa gggactctgg tcactgtctc tgcagccaaa     240 acgacaccc catctgtcta tccactggcc cctggatctg ctgcccaaac taactccatg      300
gtgaccctgg atgcctggt caagggctat ttccctgagc cagtgacagt gacctggaac      360
tctggatccc tgtccagcgg tgtgcacacc ttcc                                  394
```

<210> SEQ ID NO 70
<211> LENGTH: 476
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 70

```
tggggcttca gtgaagctgt cctgcaaggc ttctggctac accttcacca gccaatggat      60
gcagtgggtg aggcagaggc ctggacaagg ccttgagtgg attggagaga ttaatcctag     120
cagcggtcgt actcactaca atgagaagtt caagaccaag gccacactga ctgtagacaa     180
atcctccagc acagcctaca tgcaactcag cagcctgaca tctgaggact ctgcggtcta     240
ttactgtgca agaggggatg gtgactacgt ctggtttgct tactggggcc aagggactct     300
ggtcactgtc tctgcagcca aaacgacacc cccatctgtc tatccactgg cccctggatc     360
tgctgcccaa actaactcca tggtgaccct gggatgcctg gtcaagggct atttccctga     420
gccagtgaca gtgacctgga actctggatc cctgtccagc ggtgtgcaca ccttcc          476
```

<210> SEQ ID NO 71
<211> LENGTH: 392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gacaaggcct tgagtggatt ggagagatta atcctagcag cggtcgtact cactacaatg      60
agaagttcaa gaccaaggcc acactgactg tagacaaatc ctccagcaca gcctacatgc     120
aactcagcag cctgacatct gaggactctg cggtctatta ctgtgcaaga ggggatggtg     180
actacgtctg gtttgcttac tggggccaag ggactctggt cactgtctct gcagccaaaa     240
cgacaccccc atctgtctat ccactggccc ctggatctgc tgcccaaact aactccatgg     300
tgaccctggg atgcctggtc aagggctatt ccctgagcc agtgacagtg acctggaact     360
ctggatccct gtccagcggt gtgcacacct tc                                   392

<210> SEQ ID NO 72
<211> LENGTH: 446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
tgaagatatc ctgcgaggct actggctaca caatcagtag ctactggata gagtgggtaa      60
agcagaggcc tggacatggc cttgagtgga ttggagagat tttacctgga agtggtagta     120
ctacctacaa tgaaaagttc aagggcaagg ccacattcac tgcagataca tcctccaaca     180
cagcctacat gcaactcagc agcctgacat ctgaggactc tgccgcctat tactgtgcaa     240
gggcacgcac tggaccaat tactatacta tggactactg gggtcaagga acctcagtca     300
ccgtctcctc agccaaaacg acacccccat ctgtctatcc actggcccct ggatctgctg     360
cccaaactaa ctccatggtg accctgggat gcctggtcaa gggctatttc cctgagccag     420
tgacagtgac ctggaactct ggatcc                                          446

<210> SEQ ID NO 73
<211> LENGTH: 458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
agatatcctg cgaggctact ggctacacaa tcagtagcta ctggatagag tgggtaaagc      60
agaggcctgg acatggcctt gagtggattg agagatttt acctggaagt ggtagtacta     120
cctacaatga aaagttcaag ggcaaggcca cattcactgc agatacatcc tccaacacag     180
cctacatgca actcagcagc ctgacatctg aggactctgc cgcctattac tgtgcaaggg     240
cacgcactgg accaattac tatactatgg actactgggg tcaaggaacc tcagtcaccg     300
tctcctcagc caaaacgaca ccccatctg tctatccact ggcccctgga tctgctgccc     360
aaactaactc catggtgacc ctgggatgcc tggtcaaggg ctatttccct gagccagtga     420
cagtgacctg gaactctgga tccctgtcca gcggtgtg                             458

<210> SEQ ID NO 74
<211> LENGTH: 359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
ctgtcctgca aggcttctgg ctacaactcc actgactact atataaactg ggtgaagcag      60
aggactggac agggccttga gtggattgga gagatttatc ctggaagtgg taatacttat     120
tacaatgaga agttcaaggg caaggccaca ctgactgcag acaaatcctc cagcacagcc     180
tacatgcagc tcagcagcct gacatctgag gactctgcag tctatttctg tacaagaggg     240
ggggtctact atggttacga cgatgcctgg tttgtttact ggggccaagg gactctggtc     300
actgtctctg cagccaaaac aacagcccca tcggtctatc cactggcccc tgtgtgtgg      359
```

<210> SEQ ID NO 75
<211> LENGTH: 468
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
catgggctga ctgagcttct cagtctctgt ccctcacctg cactgtcact gagctactca      60
atcaccagtg attatgcctg gaactggatc cggcagtttc caggaaacaa actggagtgg     120
atgggctaca taggctacag tggtggcact agctacaacc catctctcaa aagtcgaatc     180
tctatcactc gagacacatc caagaaccag ttcttcctgc acttgaattc tgtgactact     240
gaggacacag ccacatattt ctgtgcaaga gagattacga cgacggggtg ctttgcttac     300
tggggccaag ggactctggt cactgtctct gcagccaaaa cgacaccccc atctgtctat     360
ccactggccc ctggatctgc tgcccaaact aactccatgg tgaccctggg atgcctggtc     420
aagggctatt ccctgagcc agtgacagtg acctggaact ctggatcc                   468
```

<210> SEQ ID NO 76
<211> LENGTH: 458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
gatatcctgc gaggctactg gctacacaat cagtagctac tggatagagt gggtaaagca      60
gaggcctgga catggccttg agtggattgg agagatttta cctggaagtg gtagtactac     120
ctacaatgaa aagttcaagg gcaaggccac attcactgca gatacatcct ccaacacagc     180
ctacatgcaa ctcagcagcc tgacatctga ggactctgcc gcctattact gtgcaagggc     240
acgcactggg accaattact atactatgga ctactgggggt caaggaacct cagtcaccgt     300
ctcctcagcc aaaacgacac ccccatctgt ctatccactg gccctggat ctgctgccca      360 aactaactcc atggtgaccc tgggatgcct ggtcaagggc tatttccctg agccagtgac     420
agtgacctgg aactctggat ccctgtccag cggtgtga                             458
```

<210> SEQ ID NO 77

-continued

```
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gacaaggcct tgagtggatt ggagagatta atcctagcag cggtcgtact cactacaatg      60
agaagttcaa gaccaaggcc acactgactg tagacaaatc ctccagcaca gcctacatgc     120
aactcagcag cctgacatct gaggactctg cggtctatta ctgtgcaaga ggggatggtg     180
actacgtctg gtttgcttac tggggccaag ggactctggt cactgtctct gcagccaaaa     240
cgacaccccc atctgtctat ccactggccc ctggatctgc tgcccaaact aactccatgg     300
tgaccctggg atgcctggtc aagggctatt tccctgagcc agtgacagtg acctggaact     360
ctggatccct gtccagcggt gtgca     385

<210> SEQ ID NO 78
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
ggacaaggcc ttgagtggat tggagagatt aatcctagca gcggtcgtac tcactacaat      60
gagaagttca agaccaaggc cacactgact gtagacaaat cctccagcac agcctacatg     120
caactcagca gcctgacatc tgaggactct gcggtctatt actgtgcaag aggggatggt     180
gactacgtct ggtttgctta ctggggccaa gggactctgg tcactgtctc tgcagccaaa     240
acgacacccc catctgtcta tccactggcc cctggatctg ctgcccaaac taactccatg     300
gtgaccctgg gatgcctggt caagggctat ttccctgagc cagtgacagt gacctggaac     360
tctggatccc tgtccagcgg tgtg     384

<210> SEQ ID NO 79
<211> LENGTH: 272
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
ggaactggat ccgggagatt ccaggaaac aaactggagt ggttgggcta cataagctac      60
agtggtacca ctagctacaa cccatctctc aaaagtcgaa tctctatcac tcgagacaca     120
tccaagaacc agtccttcct gcagttgaat tctgtgacta ctgaggacac agccacatat     180
tactgtgcaa gagaggttac gacgacgggg tggtttgttt actggggcca agggactctg     240
gtcactgtct ctgcagccaa aacgacaccc cc     272

<210> SEQ ID NO 80
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
```

-continued

```
ctctcctgtg cagcctcagg attcgatttt agtagatact ggatgagttg ggtccggcag        60
gctccaggga aagggctaga atggattgga gaagttaatc cagatagcag tacgataaac       120
tctacgccat ctctaaagga taaattcttc atctccagag acaacgccaa aaatacgctg       180
tacctgcaga tgatcaaagt gagatctgag gacacagccc tttattactg tgcaagactc       240
tactataatt acgtcgatta ttactatgct atggactact ggggtcaagg aacctcagtc       300
accgtctcct cagccaaaac gacaccccca tctgtctatc cactggcccc tggatctgct       360
gcccaaacta actccatggt gaccctggga tgcctggtca agggctattt ccctgagcca       420
gtgacagtga cctggaactc tggatccctg tccagcggt                              459
```

<210> SEQ ID NO 81
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
tgattatgcc tggaactgga tccggcagtt tccaggaaac aaactggagt ggttgggcta        60
cataagctac agtggtacca ctagctacaa cccatctctc aaaagtcgaa tctctatcac       120
tcgagacaca tccaagaacc agtccttcct gcagttgaat tctgtgacta ctgaggacac       180
agccacatat tactgtgcaa gagaggttac gacgacgggg tggtttgttt actggggcca       240
agggactctg gtcactgtct ctgcagccaa aacgacaccc ccatctgtct atcc             294
```

<210> SEQ ID NO 82
<211> LENGTH: 323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
acgtgtaagc tccctaatgt gctgacagta ataggttgca gcatcctcct cctccacagg        60
atggatgttg agggtgaagt ctgtcccaga cccactgcca ctgaacctgg cagggacccc       120
agattctagg ttggatacaa gatagatgag gagtctgggt ggctgtcctg gtttctgttg       180
gttccagtgc atataactat agccagatgt actgacactt ttgctggccc tgtatgagat       240
ggtggccctc tgccccagag atacagctaa ggaagcagga gactgtgtca gcacaatgtc       300
accagtggaa cctggaaccc aga                                               323
```

<210> SEQ ID NO 83
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
ttattcctcc catgattggg ggtcatttgt cttgaagggc ctttctccat ttaaatttat        60
ggtccttcca gtctcttgtt gatcttcaaa tgtttgtctt cacatagaaa tagagtcctg       120
tgtccgctgc atttggatta ccatcaccaa tctgaaatat acttgttacc catgtaatga       180
taagtttgtg ggttggg                                                      197
```

<210> SEQ ID NO 84
<211> LENGTH: 463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
taactgctca ctggatggtg ggaagatgga tacagttggt gcagcatcag cccgtttttat      60 ttccagcttg gtcccccctc cgaacgtgta agctccctaa tgtgctgaca gtaataggtt     120
gcagcatcct cctcctccac aggatggatg ttgagggtga agtctgtccc agacccactg     180
ccactgaacc tggcagggac cccagattct aggttggata caagatagat gaggagtctg     240
ggtggctgtc ctggtttctg ttggttccag tgcatataac tatagccaga tgtactgaca     300
cttttgctgg ccctgtatga gatggtggcc ctctgcccca gagatacagc taaggaagca     360
ggagactgtg tcagcacaat gtcaccagtg gaacctggaa cccagagcag cagtacccat     420
aacaggagtg tgtctgtctc catctctgag agctggaaga gag                         463

<210> SEQ ID NO 85
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
cttggtcccc cctccgaacg tgtaagctcc ctaatgtgct gacagtaata ggttgcagca      60
tcctcctcct ccacaggatg gatgttgagg gtgaagtctg tcccagaccc actgccactg     120
aacctggcag ggaccccaga ttctaggttg gatacaagat agatgaggag tctgggtggc     180
tgtcctggtt tctgttggtt ccagtgcata taactatagc cagatgtact gacacttttg     240
ctggccctgt atgagatggt ggccctctgc cccagagata cagctaagga agcaggagac     300
tgtgtcagca caatgtcacc agtggaacct ggaacccaga gcagcagca                   349

<210> SEQ ID NO 86
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gattatgatg gtgatcgtta tatgaactgg taccagcaga aaccaggaca gccacccaaa      60
ctcctcatct atgctgcatc caatctagaa tctgggatcc ctgccaggtt tagtggcagt     120
gggtctggga cagacttcac cctcaacatc catcctgtgg aggaggagga tgctgcaacc     180
tattactgtc agcacatta                                                    199

<210> SEQ ID NO 87
<211> LENGTH: 310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gacagtaata ggttgcagca tcctcctcct ccacaggatg gatgttgagg gtgaagtctg    60
tcccagaccc actgccactg aacctggcag ggaccccaga ttctaggttg gatacaagat   120
agatgaggag tctgggtggc tgtcctggtt tctgttggtt ccagtgcata taactatagc   180
cagatgtact gacacttttg ctggccctgt atgagatggt ggccctctgc cccagagata   240
cagctaagga agcaggagac tgtgtcagca caatgtcacc agtggaacct ggaacccaga   300
gcagcagcac                                                          310

<210> SEQ ID NO 88
<211> LENGTH: 242
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
aactccctaa tgtgctgaca gtaataggtt gcagcatcct cctcctccac aggatggatg    60
ttgagggtga agtatgtccc agacccactg ccactgaacc tgacagggac cccagaatcc   120
aggttggatg tgtcataaat caggagtctg ggggaggatc ctggcttctg ctggtaccag   180
tacatgtaac ttacacttga tctggcactg caggtcatgg tgaccttctc ccctggagat   240
gc                                                                  242

<210> SEQ ID NO 89
<211> LENGTH: 283
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
catcctcctc ctccacagga tggatgttga gggtgaagtc tgtcccagac ccactgccac    60
tgaacctggc agggacccca gattctaggt tggatacaag atagatgagg agtctgggtg   120
gctgtcctgg tttctgttgg ttccagtgca tataactata gccagatgta ctgacacttt   180
tgctggccct gtatgagatg gtggccctct gccccagaga tacagctaag gaagcaggag   240
actgtgtcag cacaatgcca tcagtggaac ctggaaccca gag                     283

<210> SEQ ID NO 90
<211> LENGTH: 221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
tgtgtacgtt ccatcttctt cctcctccgg ggatggatgt gaagggtgaa gccccccta     60 gacccactgc actgaatcgc cagggacccc acattcgagg ttggatacaa catatatgaa   120
catgtgggtg gctgtcctgg tttctgttgg ttcccgtgca tataactttt tccagatgta   180
ctgacacttt tgctggccct gtatgagatg gtttttcatat g                      221

<210> SEQ ID NO 91
<211> LENGTH: 309
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 91
tgacagtaat aggttgcagc atcctcctcc tccacaggat ggatgttgag ggtgaagtct        60
gtcccagacc cactgccact gaacctggca gggaccccag attctaggtt ggatacaaga       120
tagatgagga gtctgggtgg ctgtcctggt ttctgttggt tccagtgcat ataactatag       180
ccagatgtac tgacactttt gctggccctg tatgagatgg tggccctctg ccccagagat       240
acagctaagg aagcaggaga ctgtgtcagc acaatgtcac cagtggaacc tggaacccag       300
agcagcagc                                                               309

<210> SEQ ID NO 92
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
cgtgtaagct ccctaatgtg ttgaccgtaa taggttgcag catcctcctc ctcccaggat        60
ggatgttgag ggtgaagtct gtcccaaacc ccctgcccct gaacctggca gggaccccag       120
attccaggtt ggatacaaga tagatgaaga gtctgggtgg ctgtcctggt ttctgttggt       180
tcccgtgcat ataactatag ccagatgtac tgacactttt gctggccctg tatgagatgg       240
tgg                                                                     243

<210> SEQ ID NO 93
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gcagcatcct cctcctccac aggatggatg ttgagggtga agtctgtccc agacccactg        60
ccactgaacc tggcagggac cccagattct aggttggata caagatagat gaggagtctg       120
ggtggctgtc ctggtttctg ttggttccag tgcatataac tatagccaga tgtactgaca       180
cttttgctgg ccctgtatga                                                   200

<210> SEQ ID NO 94
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
tatgtcccag acccactgcc actgaacctg acagggaccc cagattctag gttggatgca        60
acataaatca tgagtctggg ggactatcct ggcttctgct ggtaccagta gatgtaactt       120
acacttgat                                                               129

<210> SEQ ID NO 95
<211> LENGTH: 215
```

-continued

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
tgacagtaat aggttgcagc atcctcctcc tccacaggat ggatgttgag ggtgaagtct      60
gtcccagacc cactgccact gaacctggca gggacccccag attctaggtt ggatacaaga     120
tagatgagga gtctgggtgg ctgtcctggt ttctgttggt tccagtgcat ataactatag     180
ccagatgtac tgacactttt gctggccctg tatga                                215

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ile Ile Ile Tyr Phe Glu Ser Ile Leu Glu Phe
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser His Ile Arg Glu Leu Thr Arg
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln His Ile Arg Glu Ile Thr Arg
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Ala Phe Thr Ser Tyr Asn Ile Tyr
1               5

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 100

Trp Ile Gly Tyr Ile Asp Pro Tyr Asn Gly Gly Thr Thr Tyr Asn
1               5                   10                  15

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Met Gly Tyr Ile Ser Tyr Ser Gly Ser Thr Tyr Tyr
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Glu Ile Tyr Tyr Asp Tyr Gly Gly Arg Phe Ala Tyr
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Glu Glu Tyr Asp Tyr Asp Glu Gly Tyr Ala Met Asp Tyr
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Tyr Tyr Gly Asp Asn Tyr Val Gly Ala Met Asp Tyr
1               5                   10

<210> SEQ ID NO 105
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Thr Leu Thr Ala Asp Lys Ser Ser Ser Thr Ala Tyr Met Gln Leu
1               5                   10                  15

Ser Ser Leu Thr Ser Glu Asp Ser Thr Val Tyr Phe Cys Ala Gly Gly
            20                  25                  30
```

-continued

```
Ser Ser Leu Tyr Val Trp Phe Ala Tyr Trp Gly Gln Gly
        35                  40                  45

<210> SEQ ID NO 106
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ala Thr Phe Thr Ala Asp Thr Ser Ser Asn Val Ala Tyr Met Gln Leu
1               5                   10                  15

Thr Ser Leu Thr Ser Glu Asp Ser Ala Val Tyr Tyr Cys Ala Arg Tyr
            20                  25                  30

Glu Tyr Gly Asn Tyr Val Trp Gly Gln Gly
        35                  40

<210> SEQ ID NO 107
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Thr Leu Thr Ala Asp Lys Ser Ser Ser Thr Ala Tyr Met Gln Leu
1               5                   10                  15

Ser Ser Leu Thr Ser Glu Asp Ser Ala Val Tyr Phe Cys Ala Arg Gly
            20                  25                  30

Asp Gly Tyr Tyr Phe Trp Phe Gly Tyr Trp Gly Gln Gly
        35                  40                  45

<210> SEQ ID NO 108
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ala Thr Phe Thr Ala Asp Thr Ser Ser Asn Thr Ala Tyr Met Gln Leu
1               5                   10                  15

Ile Thr Leu Thr Ser Glu Asp Ser Ala Val Tyr Tyr Cys Ala Thr Gly
            20                  25                  30

Ser Arg Leu Ala Trp Phe Val Tyr Trp Gly Gln Gly
        35                  40

<210> SEQ ID NO 109
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Phe Ile Ile Ser Arg Asp Asn Ala Lys Asn Thr Leu Tyr Leu Gln Met
1               5                   10                  15

Arg Lys Val Arg Ser Glu Asp Thr Ala Leu Tyr Tyr Cys Ser Arg Val
```

-continued

```
                20              25              30

Leu Leu Tyr Tyr Gly Ser Asn Pro His Trp His Phe Asp Val Trp Gly
        35              40              45

Ala Gly
    50

<210> SEQ ID NO 110
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ala Thr Leu Thr Val Asp Lys Ser Ser Ser Thr Ala Tyr Met Gln Leu
1               5               10              15

Ser Ser Leu Thr Ser Glu Asp Ser Ala Val Tyr Tyr Cys Ala Arg Gly
            20              25              30

Asp Gly Asp Tyr Val Trp Phe Ala Tyr Trp Gly Gln Gly
        35              40              45

<210> SEQ ID NO 111
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ala Thr Leu Thr Ala Asp Lys Ser Ser Ser Thr Ala Tyr Met Gln Leu
1               5               10              15

Ser Ser Leu Thr Ser Glu Asp Ser Ala Val Tyr Phe Cys Thr Arg Gly
            20              25              30

Gly Val Tyr Tyr Gly Tyr Asp Asp Ala Trp Phe Val Tyr Trp Gly Gln
        35              40              45

Gly

<210> SEQ ID NO 112
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Thr Phe Thr Ala Asp Thr Ser Ser Asn Thr Ala Tyr Met Gln Leu
1               5               10              15

Ser Ser Leu Thr Ser Glu Asp Ser Ala Ala Tyr Tyr Cys Ala Arg Ala
            20              25              30

Arg Thr Gly Thr Asn Tyr Tyr Thr Met Asp Tyr Trp Gly Gln Gly
        35              40              45

<210> SEQ ID NO 113
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 113

Ile Ser Ile Thr Arg Asp Thr Ser Lys Asn Gln Phe Phe Leu His Leu
1               5                   10                  15

Asn Ser Val Thr Thr Glu Asp Thr Ala Thr Tyr Phe Cys Ala Arg Glu
            20                  25                  30

Ile Thr Thr Thr Gly Cys Phe Ala Tyr Trp Gly Gln Gly
        35                  40                  45

<210> SEQ ID NO 114
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ile Ser Ile Thr Arg Asp Thr Ser Lys Asn Gln Ser Phe Leu Gln Leu
1               5                   10                  15

Asn Ser Val Thr Thr Glu Asp Thr Ala Thr Tyr Tyr Cys Ala Arg Glu
            20                  25                  30

Val Thr Thr Thr Gly Trp Phe Val Tyr Trp Gly Gln Gly
        35                  40                  45

<210> SEQ ID NO 115
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Phe Phe Ile Ser Arg Asp Asn Ala Lys Asn Thr Leu Tyr Leu Gln Met
1               5                   10                  15

Ile Lys Val Arg Ser Glu Asp Thr Ala Leu Tyr Tyr Cys Ala Arg Leu
            20                  25                  30

Tyr Tyr Asn Tyr Val Asp Tyr Tyr Tyr Ala Met Asp Tyr Trp Gly Gln
        35                  40                  45

Gly

<210> SEQ ID NO 116
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Pro Arg Pro Ser Glu Thr Val
65                  70                  75                  80
```

-continued

```
Thr Cys Asn Val Ala His Pro Ala Ser Ser Thr Lys Val Asp Lys Lys
                85              90              95

Ile Val Pro Arg Asp Cys Gly Cys Lys Pro Cys Ile Cys Thr Val Pro
            100             105             110

Glu Val Ser Ser Val Phe Ile Phe Pro Pro Lys Pro Lys Asp Val Leu
        115             120             125

Thr Ile Thr Leu Thr Pro Lys Val Thr Cys Val Val Val Asp Ile Ser
    130             135             140

Lys Asp Asp Pro Glu Val Gln Phe Ser Trp Phe Val Asp Asp Val Glu
145             150             155             160

Val His Thr Ala Gln Thr Gln Pro Arg Glu Glu Gln Phe Asn Ser Thr
            165             170             175

Phe Arg Ser Val Ser Glu Leu Pro Ile Met His Gln Asp Trp Leu Asn
            180             185             190

Gly Lys Glu Phe Lys Cys Arg Val Asn Ser Ala Ala Phe Pro Ala Pro
        195             200             205

Ile Glu Lys Thr Ile Ser Lys Thr Lys Gly Arg Pro Lys Ala Pro Gln
    210             215             220

Val Tyr Thr Ile Pro Pro Pro Lys Glu Gln Met Ala Lys Asp Lys Val
225             230             235             240

Ser Leu Thr Cys Met Ile Thr Asp Phe Phe Pro Glu Asp Ile Thr Val
            245             250             255

Glu Trp Gln Trp Asn Gly Gln Pro Ala Glu Asn Tyr Lys Asn Thr Gln
            260             265             270

Pro Ile Met Asn Thr Asn Gly Ser Tyr Phe Val Tyr Ser Lys Leu Asn
        275             280             285

Val Gln Lys Ser Asn Trp Glu Ala Gly Asn Thr Phe Thr Cys Ser Val
    290             295             300

Leu His Glu Gly Leu His Asn His His Thr Glu Lys Ser Leu Ser His
305             310             315             320

Ser Pro Gly Lys

<210> SEQ ID NO 117
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gly Cys Leu Gly Tyr Asn Phe Ser Asp Tyr Tyr Ile Asn Trp Val Lys
1               5               10              15

Gln Arg Thr Gly Gln Gly Leu Glu Trp Ile Gly Glu Ile Tyr Pro Gly
            20              25              30

Ser Gly Thr Thr Tyr Tyr Asn Glu Lys Phe Lys Gly Lys Ala Thr Leu
        35              40              45

Thr Ala Asp Lys Ser Ser Ser Thr Ala Tyr Met Gln Leu Ser Ser Leu
    50              55              60

Thr Ser Glu Asp Ser Thr Val Tyr Phe Cys Ala Gly Gly Ser Ser Leu
65              70              75              80

Tyr Val Trp Phe Ala Tyr Trp Gly Gln Gly Thr Leu Val Thr Val Ser
            85              90              95

Ala Ala Lys Thr Thr Pro Pro Ser Val Tyr Pro Leu Ala Pro Gly Ser
            100             105             110
```

-continued

Ala Ala Gln Thr Asn Ser Met Val Thr Leu Gly Cys Leu Val Lys Gly
        115                 120                 125

Tyr Phe Pro Glu Pro Val Thr Val Thr Trp Asn Ser Gly Ser Leu Ser
    130                 135                 140

Ser Gly Val
145

<210> SEQ ID NO 118
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Lys Val Ser Cys Lys Ala Thr Val Tyr Thr Phe Ser Ser His Trp
1               5                   10                  15

Ile Glu Trp Ile Lys Gln Arg Pro Gly His Gly Leu Glu Trp Ile Gly
            20                  25                  30

Glu Ile Leu Pro Gly Ser Gly Ser Thr Asn Tyr Asn Glu Lys Phe Lys
        35                  40                  45

Gly Lys Ala Thr Phe Thr Ala Asp Thr Ser Ser Asn Val Ala Tyr Met
    50                  55                  60

Gln Leu Thr Ser Leu Thr Ser Glu Asp Ser Ala Val Tyr Tyr Cys Ala
65                  70                  75                  80

Arg Tyr Glu Tyr Gly Asn Tyr Val Trp Gly Gln Gly Thr Leu Val Thr
                85                  90                  95

Val Ser Ala Ala Lys Thr Thr Pro Pro Ser Val Tyr Pro Leu Ala Pro
            100                 105                 110

Gly Ser Ala Ala Gln Thr Asn Ser Met Val Thr Leu Gly Cys Leu Val
        115                 120                 125

Lys Gly Tyr Phe Pro Glu Pro Val Thr Val Thr Trp Asn Ser Gly Ser
    130                 135                 140

Leu Ser Ser Gly Val His
145                 150

<210> SEQ ID NO 119
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Leu Ser Cys Lys Ala Ser Asp His Thr Phe Thr Asp Tyr Tyr Ile Asn
1               5                   10                  15

Trp Met Lys Gln Arg Thr Gly Gln Gly Leu Glu Trp Ile Gly Glu Ile
            20                  25                  30

Tyr Pro Gly Ser Gly Tyr Thr Tyr Tyr Asn Glu Lys Phe Lys Gly Lys
        35                  40                  45

Ala Thr Leu Thr Ala Asp Lys Ser Ser Ser Thr Ala Tyr Met Gln Leu
    50                  55                  60

Ser Ser Leu Thr Ser Glu Asp Ser Ala Val Tyr Phe Cys Ala Arg Gly
65                  70                  75                  80

Asp Gly Tyr Tyr Phe Trp Phe Gly Tyr Trp Gly Gln Gly Thr Leu Val
                85                  90                  95

-continued

Thr Val Ser Ala Ala Lys Thr Thr Pro Pro Ser Val Tyr Pro Leu Ala
              100                 105                 110

Pro Gly Ser Ala Ala Gln Thr Asn Ser Met Val Thr Leu Gly Cys Leu
          115                 120                 125

Val Lys Gly Tyr Phe Thr Glu Pro Val Thr Val Thr
      130                 135                 140

<210> SEQ ID NO 120
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Lys Leu Ser Cys Lys Ala Ser Asp His Thr Phe Thr Asp Tyr Tyr Ile
1               5                   10                  15

Asn Trp Met Lys Gln Arg Thr Gly Gln Gly Leu Glu Trp Ile Gly Glu
              20                  25                  30

Ile Tyr Pro Gly Ser Gly Tyr Thr Tyr Tyr Asn Glu Lys Phe Lys Gly
          35                  40                  45

Lys Ala Thr Leu Thr Ala Asp Lys Ser Ser Ser Thr Ala Tyr Met Gln
      50                  55                  60

Leu Ser Ser Leu Thr Ser Glu Asp Ser Ala Val Tyr Phe Cys Ala Arg
65                  70                  75                  80

Gly Asp Gly Tyr Tyr Phe Trp Phe Gly Tyr Trp Gly Gln Gly Thr Leu
                  85                  90                  95

Val Thr Val Ser Ala Ala Lys Thr Thr Pro Pro Ser Val Tyr Pro Leu
              100                 105                 110

Ala Pro Gly Ser Ala Ala Gln Thr Asn Ser Met Val Thr Leu Gly Cys
          115                 120                 125

Leu Val Lys Gly Tyr Phe Pro Glu Pro Val Thr Val Thr Trp Asn Ser
      130                 135                 140

Gly Ser Leu Ser Ser Gly Val
145                 150

<210> SEQ ID NO 121
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Gln Glu Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
              20                  25                  30

Trp Ile Glu Trp Val Lys Gln Arg Pro Gly His Gly Leu Glu Trp Ile
          35                  40                  45

Gly Glu Ile Leu Pro Gly Ser Gly Ser Thr Tyr His Asn Glu Asn Phe
      50                  55                  60

Lys Gly Lys Ala Thr Phe Thr Ala Asp Thr Ser Ser Asn Thr Ala Tyr
65                  70                  75                  80

Met Gln Leu Ile Thr Leu Thr Ser Glu Asp Ser Ala Val Tyr Tyr Cys
                  85                  90                  95

-continued

Ala Thr Gly Ser Arg Leu Ala Trp Phe Val Tyr Trp Gly Gln Gly Thr
            100                     105                 110

Leu Val Asn Val Ser Ala Ala Lys Thr Thr Pro Pro Ser Val Tyr Pro
        115                     120                 125

Leu Ala Pro Gly Ser Ala Ala Gln Thr Asn Ser Met Val Thr Leu Gly
    130                     135                 140

Cys Leu Val Lys Gly Tyr Phe Pro Glu Pro Val Thr Val Thr Trp Asn
145                     150                 155                 160

Ser Gly Ser Leu Ser Arg Gly Val
            165

<210> SEQ ID NO 122
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Lys Ile Ser Cys Lys Ala Thr Gly Tyr Thr Phe Ser Asn Tyr Trp Ile
1               5                   10                  15

Glu Trp Val Lys Gln Arg Pro Gly His Gly Leu Glu Trp Ile Gly Glu
            20                  25                  30

Ile Leu Pro Gly Ser Gly Ser Thr Tyr His Asn Glu Asn Phe Lys Gly
        35                  40                  45

Lys Ala Thr Phe Thr Ala Asp Thr Ser Ser Asn Thr Ala Tyr Met Gln
    50                  55                  60

Leu Ile Thr Leu Thr Ser Glu Asp Ser Ala Val Tyr Tyr Cys Ala Thr
65                  70                  75                  80

Gly Ser Arg Leu Ala Trp Phe Val Tyr Trp Gly Gln Gly Thr Leu Val
                85                  90                  95

Asn Val Ser Ala Ala Lys Thr Thr Pro Pro Ser Val Tyr Pro Leu Ala
            100                 105                 110

Pro Gly Ser Ala Ala Gln Thr Asn Ser Met Val Thr Leu Gly Cys Leu
        115                 120                 125

Val Lys Gly Tyr Phe Pro Glu Pro Val Thr Val Thr Trp Asn Ser Gly
    130                 135                 140

Ser Leu Trp
145

<210> SEQ ID NO 123
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Lys Leu Leu Glu Ser Gly Gly Gly Leu Val Gln Pro Gly Gly
1               5                   10                  15

Ser Pro Glu Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Arg Lys Val Arg Ser Glu Asp Thr Ala Leu Tyr Tyr Cys
                85                  90                  95

Ser Arg Val Leu Leu Tyr Tyr Gly Ser Asn Pro His Trp His Phe Asp
            100                 105                 110

Val Trp Gly Ala Gly Thr Thr Val Thr Val Ser Ser Ala Lys Thr Thr
        115                 120                 125

Pro Pro Ser Val Tyr Pro Leu Ala Pro Gly Ser Ala Ala Gln Thr Asn
        130                 135                 140

Ser Met Val Thr Leu Gly Cys Leu Val Lys Gly Tyr Phe Pro Glu Pro
145                 150                 155                 160

Val Thr Val Thr Trp Asn Ser Gly Ser Leu Ser Ser Gly Val Thr Thr
                165                 170                 175

Leu

<210> SEQ ID NO 124
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gly Glu Phe Glu Val Gln Leu Gln Glu Ser Gly Ala Glu Leu Val Lys
1               5                   10                  15

Pro Gly Ala Ser Val Lys Leu Ser Cys Lys Ala Ser Gly Tyr Thr Phe
            20                  25                  30

Thr Ser Gln Trp Met Gln Trp Val Arg Gln Arg Pro Gly Gln Gly Leu
        35                  40                  45

Glu Trp Ile Gly Glu Ile Asn Pro Ser Ser Gly Arg Thr His Tyr Asn
    50                  55                  60

Glu Lys Phe Lys Thr Lys Ala Thr Leu Thr Val Asp Lys Ser Ser Ser
65                  70                  75                  80

Thr Ala Tyr Met Gln Leu Ser Ser Leu Thr Ser Glu Asp Ser Ala Val
                85                  90                  95

Tyr Tyr Cys Ala Arg Gly Asp Gly Asp Tyr Val Trp Phe Ala Tyr Trp
            100                 105                 110

Gly Gln Gly Thr Leu Val Thr Val Ser Ala Ala Lys Thr Thr Pro Pro
        115                 120                 125

Ser Val Tyr Pro Leu Ala Pro Gly Ser Ala Ala Gln Thr Asn Ser Met
        130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe
                165                 170                 175

<210> SEQ ID NO 125
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gly Ala Ser Val Lys Leu Ser Cys Lys Ala Ser Gly Tyr Thr Phe Thr

-continued

```
1               5               10              15

Ser Gln Trp Met Gln Trp Val Arg Gln Arg Pro Gly Gln Gly Leu Glu
            20              25              30

Trp Ile Gly Glu Ile Asn Pro Ser Ser Gly Arg Thr His Tyr Asn Glu
            35              40              45

Lys Phe Lys Thr Lys Ala Thr Leu Thr Val Asp Lys Ser Ser Ser Thr
    50              55              60

Ala Tyr Met Gln Leu Ser Ser Leu Thr Ser Glu Asp Ser Ala Val Tyr
65              70              75              80

Tyr Cys Ala Arg Gly Asp Gly Asp Tyr Val Trp Phe Ala Tyr Trp Gly
                85              90              95

Gln Gly Thr Leu Val Thr Val Ser Ala Ala Lys Thr Thr Pro Pro Ser
            100             105             110

Val Tyr Pro Leu Ala Pro Gly Ser Ala Ala Gln Thr Asn Ser Met Val
            115             120             125

Thr Leu Gly Cys Leu Val Lys Gly Tyr Phe Pro Glu Pro Val Thr Val
    130             135             140

Thr Trp Asn Ser Gly Ser Leu Ser Ser Gly Val His Thr Phe
145             150             155
```

```
<210> SEQ ID NO 126
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126
```

```
Arg Tyr Pro Ala Arg Leu Leu Ala Thr Gln Ser Arg Ser Tyr Trp Ile
1               5               10              15

Glu Trp Val Lys Gln Arg Pro Gly His Gly Leu Glu Trp Ile Gly Glu
            20              25              30

Ile Leu Pro Gly Ser Gly Ser Thr Thr Tyr Asn Glu Lys Phe Lys Gly
            35              40              45

Lys Ala Thr Phe Thr Ala Asp Thr Ser Ser Asn Thr Ala Tyr Met Gln
    50              55              60

Leu Ser Ser Leu Thr Ser Glu Asp Ser Ala Ala Tyr Tyr Cys Ala Arg
65              70              75              80

Ala Arg Thr Gly Thr Asn Tyr Tyr Thr Met Asp Tyr Trp Gly Gln Gly
                85              90              95

Thr Ser Val Thr Val Ser Ser Ala Lys Thr Thr Pro Pro Ser Val Tyr
            100             105             110

Pro Leu Ala Pro Gly Ser Ala Ala Gln Thr Asn Ser Met Val Thr Leu
            115             120             125

Gly Cys Leu Val Lys Gly Tyr Phe Pro Glu Pro Val Thr Val Thr Trp
    130             135             140

Asn Ser Gly
145
```

```
<210> SEQ ID NO 127
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 127

Arg Ile Ser Cys Glu Ala Thr Gly Tyr Thr Ile Ser Ser Tyr Trp Ile
1               5                   10                  15

Glu Trp Val Lys Gln Arg Pro Gly His Gly Leu Glu Trp Ile Gly Glu
            20                  25                  30

Ile Leu Pro Gly Ser Gly Ser Thr Thr Tyr Asn Glu Lys Phe Lys Gly
        35                  40                  45

Lys Ala Thr Phe Thr Ala Asp Thr Ser Ser Asn Thr Ala Tyr Met Gln
    50                  55                  60

Leu Ser Ser Leu Thr Ser Glu Asp Ser Ala Ala Tyr Tyr Cys Ala Arg
65                  70                  75                  80

Ala Arg Thr Gly Thr Asn Tyr Tyr Thr Met Asp Tyr Trp Gly Gln Gly
                85                  90                  95

Thr Ser Val Thr Val Ser Ser Ala Lys Thr Thr Pro Pro Ser Val Tyr
                100                 105                 110

Pro Leu Ala Pro Gly Ser Ala Ala Gln Thr Asn Ser Met Val Thr Leu
        115                 120                 125

Gly Cys Leu Val Lys Gly Tyr Phe Pro Glu Pro Val Thr Val Thr Trp
    130                 135                 140

Asn Ser Gly Ser Leu Ser Ser Gly Val
145                 150

<210> SEQ ID NO 128
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Gln Glu Ser Gly Ala Glu Leu Ala Arg Pro Gly Ala
1               5                   10                  15

Ser Val Lys Leu Ser Cys Lys Ala Ser Gly Tyr Thr Ser Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Gly Gly Val Tyr Tyr Gly Tyr Asp Asp Ala Trp Phe Val Tyr
                100                 105                 110

Trp Gly Gln Gly Thr Leu Val Thr Val Ser Ala Ala Lys Thr Thr Ala
        115                 120                 125

<210> SEQ ID NO 129
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

His Gly Leu Thr Glu Leu Leu Ser Leu Cys Pro Ser Pro Ala Leu Ser
```

```
1               5                   10                  15

Leu Ser Tyr Ser Ile Thr Ser Asp Tyr Ala Trp Asn Trp Ile Arg Gln
            20                  25                  30

Phe Pro Gly Asn Lys Leu Glu Trp Met Gly Tyr Ile Gly Tyr Ser Gly
            35                  40                  45

Gly Thr Ser Tyr Asn Pro Ser Leu Lys Ser Arg Ile Ser Ile Thr Arg
        50                  55                  60

Asp Thr Ser Lys Asn Gln Phe Phe Leu His Leu Asn Ser Val Thr Thr
65                  70                  75                  80

Glu Asp Thr Ala Thr Tyr Phe Cys Ala Arg Glu Ile Thr Thr Thr Gly
                85                  90                  95

Cys Phe Ala Tyr Trp Gly Gln Gly Thr Leu Val Thr Val Ser Ala Ala
            100                 105                 110

Lys Thr Thr Pro Pro Ser Val Tyr Pro Leu Ala Pro Gly Ser Ala Ala
            115                 120                 125

Gln Thr Asn Ser Met Val Thr Leu Gly Cys Leu Val Lys Gly Tyr Phe
        130                 135                 140

Pro Glu Pro Val Thr Val Thr Trp Asn Ser Gly Ser
145                 150                 155
```

```
<210> SEQ ID NO 130
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Leu Gln Glu Ser Gly Ala Glu Leu Met Lys Pro Gly Ala Ser Val
1               5                   10                  15

Lys Ile Ser Cys Glu Ala Thr Gly Tyr Thr Ile Ser Ser Tyr Trp Ile
            20                  25                  30

Glu Trp Val Lys Gln Arg Pro Gly His Gly Leu Glu Trp Ile Gly Glu
            35                  40                  45

Ile Leu Pro Gly Ser Gly Ser Thr Thr Tyr Asn Glu Lys Phe Lys Gly
        50                  55                  60

Lys Ala Thr Phe Thr Ala Asp Thr Ser Ser Asn Thr Ala Tyr Met Gln
65                  70                  75                  80

Leu Ser Ser Leu Thr Ser Glu Asp Ser Ala Ala Tyr Tyr Cys Ala Arg
                85                  90                  95

Ala Arg Thr Gly Thr Asn Tyr Tyr Thr Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val
                165
```

```
<210> SEQ ID NO 131
<211> LENGTH: 155
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 131

Gly Ala Ser Val Lys Leu Ser Cys Lys Ala Ser Gly Tyr Thr Phe Thr
1               5                   10                  15

Ser Gln Trp Met Gln Trp Val Arg Gln Arg Pro Gly Gln Gly Leu Glu
            20                  25                  30

Trp Ile Gly Glu Ile Asn Pro Ser Ser Gly Arg Thr His Tyr Asn Glu
        35                  40                  45

Lys Phe Lys Thr Lys Ala Thr Leu Thr Val Asp Lys Ser Ser Ser Thr
    50                  55                  60

Ala Tyr Met Gln Leu Ser Ser Leu Thr Ser Glu Asp Ser Ala Val Tyr
65                  70                  75                  80

Tyr Cys Ala Arg Gly Asp Gly Asp Tyr Val Trp Phe Ala Tyr Trp Gly
                85                  90                  95

Gln Gly Thr Leu Val Thr Val Ser Ala Ala Lys Thr Thr Pro Pro Ser
            100                 105                 110

Val Tyr Pro Leu Ala Pro Gly Ser Ala Ala Gln Thr Asn Ser Met Val
        115                 120                 125

Thr Leu Gly Cys Leu Val Lys Gly Tyr Phe Pro Glu Pro Val Thr Val
    130                 135                 140

Thr Trp Asn Ser Gly Ser Leu Ser Ser Gly Val
145                 150                 155

<210> SEQ ID NO 132
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Thr Gly Ser Gly Arg Phe Pro Gly Asn Lys Leu Glu Trp Leu Gly
1               5                   10                  15

Tyr Ile Ser Tyr Ser Gly Thr Thr Ser Tyr Asn Pro Ser Leu Lys Ser
            20                  25                  30

Arg Ile Ser Ile Thr Arg Asp Thr Ser Lys Asn Gln Ser Phe Leu Gln
        35                  40                  45

Leu Asn Ser Val Thr Thr Glu Asp Thr Ala Thr Tyr Tyr Cys Ala Arg
    50                  55                  60

Glu Val Thr Thr Thr Gly Trp Phe Val Tyr Trp Gly Gln Gly Thr Leu
65                  70                  75                  80

Val Thr Val Ser Ala Ala Lys Thr Thr Pro
            85                  90

<210> SEQ ID NO 133
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Leu Ser Cys Ala Ala Ser Gly Phe Asp Phe Ser Arg Tyr Trp Met Ser
1               5                   10                  15

Trp Val Arg Gln Ala Pro Gly Lys Gly Leu Glu Trp Ile Gly Glu Val
```

-continued

```
              20             25             30

Asn Pro Asp Ser Ser Thr Ile Asn Ser Thr Pro Ser Leu Lys Asp Lys
       35             40             45

Phe Phe Ile Ser Arg Asp Asn Ala Lys Asn Thr Leu Tyr Leu Gln Met
   50             55             60

Ile Lys Val Arg Ser Glu Asp Thr Ala Leu Tyr Tyr Cys Ala Arg Leu
65             70             75             80

Tyr Tyr Asn Tyr Val Asp Tyr Tyr Ala Met Asp Tyr Trp Gly Gln
              85             90             95

Gly Thr Ser Val Thr Val Ser Ser Ala Lys Thr Thr Pro Pro Ser Val
              100            105            110

Tyr Pro Leu Ala Pro Gly Ser Ala Ala Gln Thr Asn Ser Met Val Thr
       115            120            125

Leu Gly Cys Leu Val Lys Gly Tyr Phe Pro Glu Pro Val Thr Val Thr
       130            135            140

Trp Asn Ser Gly Ser Leu Ser Ser Gly
145            150
```

```
<210> SEQ ID NO 134
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Thr Gly Ser Gly Arg Phe Pro Gly Asn Lys Leu Glu Trp Leu Gly
1               5              10             15

Tyr Ile Ser Tyr Ser Gly Thr Thr Ser Tyr Asn Pro Ser Leu Lys Ser
              20             25             30

Arg Ile Ser Ile Thr Arg Asp Thr Ser Gln Asn Gln Ser Phe Leu Gln
       35             40             45

Leu Asn Ser Val Thr Thr Glu Asp Thr Ala Thr Tyr Tyr Cys Ala Arg
   50             55             60

Glu Val Thr Thr Thr Gly Trp Phe Val Tyr Trp Gly Gln Gly Thr Leu
65             70             75             80

Val Thr Val Ser Ala Ala Lys Thr Thr Pro Pro Ser Val Tyr
              85             90
```

```
<210> SEQ ID NO 135
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Thr Phe Gly Gly Gly Thr Lys Val Gly Ile Lys Arg Ala Asp Ala Ala
1               5              10             15

Pro Thr Val Ser Ile Phe Pro Pro Ser Ser Glu Gln Leu Thr Ser Gly
              20             25             30

Gly Ala Ser Val Val Cys Phe Leu Asn Asn Phe Tyr Pro Lys Asp Ile
       35             40             45

Asn Val Lys Trp Lys Ile Asp Gly Ser Glu Arg Gln Asn Gly Val Leu
   50             55             60

Asn Ser Trp Thr Asp Gln Asp Ser Lys Asp Ser Thr Tyr Ser Met Ser
```

-continued

```
65              70              75              80

Ser Thr Leu Thr Leu Thr Lys Asp Glu Tyr Glu Arg His Asn Ser Tyr
                85              90              95

Thr Cys Glu Ala Thr His Lys Thr Ser Thr Ser Pro Ile Val Lys Ser
            100             105             110

Phe Asn Arg Asn Glu Cys
        115

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Trp Val Pro Gly Ser Thr Gly Asp Ile Val Leu Thr Gln Ser Pro Ala
1               5               10              15

Ser Leu Ala Val Ser Leu Gly Gln Arg Ala Thr Ile Ser Tyr Arg Ala
            20              25              30

Ser Lys Ser Val Ser Thr Ser Gly Tyr Ser Tyr Met His Trp Asn Gln
        35              40              45

Gln Lys Pro Gly Gln Pro Pro Arg Leu Leu Ile Tyr Leu Val Ser Asn
    50              55              60

Leu Glu Ser Gly Val Pro Ala Arg Phe Ser Gly Ser Gly Ser Gly Thr
65              70              75              80

Asp Phe Thr Leu Asn Ile His Pro Val Glu Glu Glu Asp Ala Ala Thr
                85              90              95

Tyr Tyr Cys Gln His Ile Arg Glu Leu Thr Arg
            100             105

<210> SEQ ID NO 137
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gly Asp Ile Val Leu Thr Gln Ser Pro Ala Ser Leu Ala Val Ser Leu
1               5               10              15

Gly Gln Arg Ala Thr Ile Ser Tyr Arg Ala Ser Lys Ser Val Ser Thr
            20              25              30

Ser Gly Tyr Ser Tyr Met His Trp Asn Gln Gln Lys Pro Gly Gln Pro
        35              40              45

Pro Arg Leu Leu Ile Tyr Leu Val Ser Asn Leu Glu Ser Gly Val Pro
    50              55              60

Ala Arg Phe Ser Gly Ser Gly Ser Gly Thr Asp Phe Thr Leu Asn Ile
65              70              75              80

His Pro Val Glu Glu Glu Asp Ala Ala Thr Tyr Tyr Cys
                85              90

<210> SEQ ID NO 138
<211> LENGTH: 118
<212> TYPE: PRT
<213> ORGANISM: Artificial Sequence
<220> FEATURE:
<223> OTHER INFORMATION: Description of Artificial Sequence: Synthetic
```

```
        polypeptide

<400> SEQUENCE: 138

Leu Leu Leu Leu Trp Val Pro Gly Ser Thr Gly Asp Ile Val Leu Thr
1               5                   10                  15

Gln Ser Pro Ala Ser Leu Ala Val Ser Leu Gly Gln Arg Ala Thr Ile
            20                  25                  30

Ser Tyr Arg Ala Ser Lys Ser Val Ser Thr Ser Gly Tyr Ser Tyr Met
        35                  40                  45

His Trp Asn Gln Gln Lys Pro Gly Gln Pro Pro Arg Leu Leu Ile Tyr
    50                  55                  60

Leu Val Ser Asn Leu Glu Ser Gly Val Pro Ala Arg Phe Ser Gly Ser
65                  70                  75                  80

Gly Ser Gly Thr Asp Phe Thr Leu Asn Ile His Pro Val Glu Glu Glu
                85                  90                  95

Asp Ala Ala Thr Tyr Tyr Cys Gln His Ile Arg Glu Leu Thr Arg Ser
            100                 105                 110

Glu Gly Gly Pro Ser Tyr
        115

<210> SEQ ID NO 139
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Leu Leu Trp Val Pro Gly Ser Thr Gly Asp Ile Val Leu Thr Gln
1               5                   10                  15

Ser Pro Ala Ser Leu Ala Val Ser Leu Gly Gln Arg Ala Thr Ile Ser
            20                  25                  30

Tyr Arg Ala Ser Lys Ser Val Ser Thr Ser Gly Tyr Ser Tyr Met His
        35                  40                  45

Trp Asn Gln Gln Lys Pro Gly Gln Pro Pro Arg Leu Leu Ile Tyr Leu
    50                  55                  60

Val Ser Asn Leu Glu Ser Gly Val Pro Ala Arg Phe Ser Gly Ser Gly
65                  70                  75                  80

Ser Gly Thr Asp Phe Thr Leu Asn Ile His Pro Val Glu Glu Glu Asp
                85                  90                  95

Ala Ala Thr Tyr Tyr Cys Gln His Ile Arg Glu Leu Thr Arg Ser Glu
            100                 105                 110

Gly Gly Pro Ser
        115

<210> SEQ ID NO 140
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Leu Leu Leu Trp Val Pro Gly Ser Thr Gly Asp Ile Val Leu Thr Gln
1               5                   10                  15

Ser Pro Ala Ser Leu Ala Val Ser Leu Gly Gln Arg Ala Thr Ile Ser
            20                  25                  30
```

```
Tyr Arg Ala Ser Lys Ser Val Ser Thr Ser Gly Tyr Ser Tyr Met His
        35                  40                  45

Trp Tyr Gln Gln Lys Pro Gly Gln Pro Pro Lys Leu Leu Ile Tyr Ala
    50                  55                  60

Ala Ser Asn Leu Glu Ser Gly Ile Pro Ala Arg Phe Ser Gly Ser Gly
65                  70                  75                  80

Ser Gly Thr Asp Phe Thr Leu Asn Ile His Pro Val Glu Glu Glu Asp
                85                  90                  95

Ala Ala Thr Tyr Tyr Cys Gln His Ile Arg Glu Leu Thr
            100                 105

<210> SEQ ID NO 141
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Leu Leu Leu Trp Val Pro Gly Ser Thr Gly Asp Ile Val Leu Thr Gln
1               5                   10                  15

Ser Pro Ala Ser Leu Ala Val Ser Leu Gly Gln Arg Ala Thr Ile Ser
            20                  25                  30

Tyr Arg Ala Ser Lys Ser Val Ser Thr Ser Gly Tyr Ser Tyr Met His
        35                  40                  45

Trp Asn Gln Gln Lys Pro Gly Gln Pro Pro Arg Leu Leu Ile Tyr Leu
    50                  55                  60

Val Ser Asn Leu Glu Ser Gly Val Pro Ala Arg Phe Ser Gly Ser Gly
65                  70                  75                  80

Ser Gly Thr Asp Phe Thr Leu Asn Ile His Pro Val Glu Glu Glu Asp
                85                  90                  95

Ala Ala Thr Tyr Tyr Cys Gln His Ile Arg Glu Leu Thr Arg Ser Glu
            100                 105                 110

<210> SEQ ID NO 142
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Lys Val Thr Met Thr Cys Ser Ala Arg Ser Ser Val Ser Tyr Met Tyr
1               5                   10                  15

Trp Tyr Gln Gln Lys Pro Gly Ser Ser Pro Arg Leu Leu Ile Tyr Asp
            20                  25                  30

Thr Ser Asn Leu Asp Ser Gly Val Pro Val Arg Phe Ser Gly Ser Gly
        35                  40                  45

Ser Gly Thr Tyr Phe Thr Leu Asn Ile His Pro Val Glu Glu Glu Asp
    50                  55                  60

Ala Ala Thr Tyr Tyr Cys Gln His Ile Arg Glu Phe Thr Arg Ser Glu
65                  70                  75                  80

Gly Gly Gly Thr Lys Val
                85

<210> SEQ ID NO 143
```

```
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Leu Leu Leu Leu Trp Val Pro Gly Ser Thr Gly Asp Ile Val Leu Thr
1               5                   10                  15

Gln Ser Pro Ala Ser Leu Ala Val Ser Leu Gly Gln Arg Ala Thr Ile
            20                  25                  30

Ser Tyr Arg Ala Ser Lys Ser Val Ser Thr Ser Gly Tyr Ser Tyr Met
        35                  40                  45

His Trp Asn Gln Gln Lys Pro Gly Gln Pro Pro Arg Leu Leu Ile Tyr
    50                  55                  60

Leu Val Ser Asn Leu Glu Ser Gly Val Pro Ala Arg Phe Ser Gly Ser
65                  70                  75                  80

Gly Ser Gly Thr Asp Phe Thr Leu Asn Ile His Pro Val Glu Glu Glu
                85                  90                  95

Asp Ala Ala Thr Tyr Tyr Cys Gln His Ile Arg Glu Leu Thr Arg Ser
            100                 105                 110

Glu Cys Phe Leu Asn Asn Phe Tyr Pro Lys Asp Ile Asn Val Lys Trp
        115                 120                 125

Lys Ile Asp Gly Ser Glu Arg Gln Asn Gly
    130                 135

<210> SEQ ID NO 144
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Thr Ile Ser Tyr Arg Ala Ser Lys Ser Val Ser Thr Ser Gly Lys Ser
1               5                   10                  15

Tyr Met His Gly Asn Gln Gln Lys Pro Gly Gln Pro Pro Thr Cys Ser
            20                  25                  30

Tyr Met Leu Tyr Pro Thr Ser Asn Val Gly Ser Leu Ala Ile Gln Cys
        35                  40                  45

Ser Gly Ser Arg Gly Gly Phe Thr Leu His Ile His Pro
    50                  55                  60

<210> SEQ ID NO 145
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Leu Gly Val Leu Leu Leu Trp Val Pro Gly Ser Thr Gly Asp Ile
1               5                   10                  15

Val Leu Thr Gln Ser Pro Ala Ser Leu Ala Val Ser Leu Gly Gln Arg
            20                  25                  30

Ala Thr Ile Ser Tyr Arg Ala Ser Lys Ser Val Ser Thr Ser Gly Tyr
        35                  40                  45
```

-continued

```
Ser Tyr Met His Trp Asn Gln Gln Lys Pro Gly Gln Pro Pro Arg Leu
    50                  55              60

Leu Ile Tyr Leu Val Ser Asn Leu Glu Ser Gly Val Pro Ala Arg Phe
65                  70              75                  80

Ser Gly Ser Gly Ser Gly Thr Asp Phe Thr Leu Asn Ile His Pro Val
                85              90                  95

Glu Glu Glu Asp Ala Ala Thr Tyr Tyr Cys His His Ile Arg Glu Leu
            100             105             110

Thr Arg Glu Gly Gly Gly
        115

<210> SEQ ID NO 146
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Thr Ile Ser Tyr Arg Ala Ser Lys Ser Val Ser Thr Ser Gly Tyr Ser
1               5               10              15

Tyr Met His Gly Asn Gln Gln Lys Pro Gly Gln Pro Pro Arg Leu Phe
            20              25              30

Ile Tyr Leu Val Ser Asn Leu Glu Ser Gly Val Pro Ala Arg Phe Ser
        35              40              45

Gly Ser Gly Ser Gly Thr Asp Phe Thr Leu Asn Ile His Pro Val Glu
    50              55              60

Glu Glu
65

<210> SEQ ID NO 147
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Trp Ala Thr Ile Ser Tyr Arg Ala Ser Lys Ser Val Ser Thr Ser Gly
1               5               10              15

Tyr Ser Tyr Met His Trp Asn Gln Gln Lys Pro Gly Gln Pro Pro Leu
            20              25              30

Leu Ile Tyr Leu Val Ser Asn Leu Glu Ser Gly Val Pro Ala Arg Phe
        35              40              45

Ser Gly Ser Gly Ser Gly Thr Asp Phe Thr Leu Asn Ile His Pro Val
    50              55              60

Glu Glu Glu Asp Ala Ala Thr Tyr Tyr Cys His Arg Ser Leu Gly Ser
65              70              75              80

Leu Arg Ser Glu Gly Gly Gly
            85

<210> SEQ ID NO 148
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 148

Arg Leu Val Ile Tyr Asp Thr Ser Asn Leu Ala Ser Gly Val Pro Val
1               5                   10                  15

Arg Phe Ser Gly Ser Gly Cys Trp Thr Cys Phe Ser Leu Asn Ile His
            20                  25                  30

Pro Val Glu Glu Glu Asp Ala Ala Thr Tyr Tyr Cys Gln His Ile Arg
        35                  40                  45

Glu Phe Thr Arg Ser Glu Gly Gly Gly
    50                  55

<210> SEQ ID NO 149
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ser Tyr Arg Ala Ser Lys Ser Val Ser Thr Ser Gly Tyr Ser Tyr Met
1               5                   10                  15

His Trp Asn Gln Gln Lys Pro Gly Gln Pro Pro Arg Leu Leu Ile Tyr
            20                  25                  30

Leu Val Ser Asn Leu Glu Ser Gly Val Pro Ala Arg Phe Ser Gly Ser
        35                  40                  45

Gly Ser Gly Thr Asp Phe Thr Leu Asn Ile His Pro Val Glu Glu Glu
    50                  55                  60

Asp Ala Ala Thr Tyr Tyr Cys His His Ile Arg Glu Leu Thr Ser Glu
65                  70                  75                  80

Gly Gly Gly

<210> SEQ ID NO 150
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Val Gln Leu Gln Glu Ser Gly Ala Glu Leu Met Lys Pro Gly Ala Ser
1               5                   10                  15

Val Lys Ile Ser Cys Lys Ala Thr Gly Tyr Lys Phe Ser Ser Tyr Trp
            20                  25                  30

Ile Asp Trp Val Arg Gln Arg Pro Gly His Gly Leu Glu Trp Ile Gly
            35                  40                  45

Glu Ile Leu Pro Gly Ser Ser Ser Tyr Tyr Asn Glu Lys Phe Lys
    50                  55                  60

Gly Lys Ala Thr Phe Thr Ala Asp Thr Ser Ser Asn Thr Ala Ser Met
65                  70                  75                  80

Gln Leu Ser Ser Leu Thr Ser Glu Asp Ser Ala Val Tyr Tyr Cys Ala
                85                  90                  95

Arg Trp Asp Thr Tyr Tyr Trp Tyr Phe Asp Val Trp Gly Ala Gly Thr
            100                 105                 110

Thr Val Thr Val Ser Ser Ala Lys Thr Thr Pro Pro Ser Val Tyr Pro
        115                 120                 125

Leu Ala Pro Gly Ser Ala Ala Gln Thr Asn Ser His
    130                 135                 140
```

<210> SEQ ID NO 151
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Phe Glu Val Gln Leu Gln Glu Ser Gly Ala Asp Leu Val Arg Ser
1               5                   10                  15

Gly Ala Ser Val Lys Leu Ser Cys Thr Ala Ser Gly Phe Asn Ile Lys
            20                  25                  30

Asp Tyr Tyr Ile His Trp Val Lys Gln Arg Pro Glu Gln Gly Leu Glu
        35                  40                  45

Trp Ile Gly Trp Ile Asp Pro Glu Asn Gly Asp Thr Glu Tyr Asp Pro
    50                  55                  60

Lys Phe Gln Gly Lys Ala Thr Met Ser Ala Asp Thr Ser Ser Asn Thr
65                  70                  75                  80

Ala Tyr Leu Gln Leu Ser Ser Leu Thr Ser Glu Asp Thr Ala Val Tyr
                85                  90                  95

Tyr Cys Asn Ser Ser Thr Met Ile Thr Thr Ala Leu Phe Ala Tyr Trp
            100                 105                 110

Gly Gln Gly Thr Leu Val Thr Val Ser Ala Ala Lys Thr Thr Pro Pro
        115                 120                 125

<210> SEQ ID NO 152
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Lys Ile Ser Cys Lys Ala Thr Gly Tyr Lys Phe Ser Ser Tyr Trp
1               5                   10                  15

Ile Asp Trp Val Arg Gln Arg Pro Gly His Gly Leu Glu Trp Ile Gly
            20                  25                  30

Glu Ile Leu Pro Gly Ser Ser Ser Tyr Tyr Asn Glu Lys Phe Lys
        35                  40                  45

Gly Lys Ala Thr Phe Thr Ala Asp Thr Ser Ser Asn Thr Ala Ser Met
    50                  55                  60

Gln Leu Ser Ser Leu Thr Ser Glu Asp Ser Ala Val Tyr Tyr Cys Ala
65                  70                  75                  80

Arg Trp Asp Thr Tyr Tyr Trp Tyr Phe Asp Val Trp Gly Ala Gly Thr
                85                  90                  95

Thr Val Thr Val Ser Ser Ala Lys Thr Thr Pro Pro Ser Val Tyr Pro
            100                 105                 110

Leu Ala Pro Gly Ser Ala Ala Gln Thr Asn Ser Met Val Thr Leu Gly
        115                 120                 125

Cys Leu Val Lys Gly Tyr Phe Pro Glu Pro Val Thr Val Thr Trp Asn
    130                 135                 140

Ser Gly Ser Leu Ser Ser Gly
145                 150

<210> SEQ ID NO 153

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Thr Phe Gly Gly Gly Thr Lys Val Gly Ile Lys Arg Ala Asp Ala Ala
1               5                   10                  15

Pro Thr Val Ser Ile Phe Pro Pro Ser Ser Glu Gln Leu Thr Ser Gly
            20                  25                  30

Gly Ala Ser Val Val Cys Phe Leu Asn Asn Phe Tyr Pro Lys Asp Ile
        35                  40                  45

Asn Val Lys Trp Lys Ile Asp Gly Ser Glu Arg Gln Asn Gly Val Leu
    50                  55                  60

Asn Ser Trp Thr Asp Gln Asp Ser Lys Asp Ser Thr Tyr Ser Met Ser
65                  70                  75                  80

Ser Thr Leu Thr Leu Thr Lys Asp Glu Tyr Glu Arg His Asn Ser Tyr
                85                  90                  95

Thr Cys Glu Ala Thr His Lys Thr Ser Thr Ser Pro Ile Val Lys Ser
            100                 105                 110

Phe Asn Arg Asn Glu Cys
        115

<210> SEQ ID NO 154
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Leu Leu Leu Trp Val Pro Gly Ser Thr Gly Asp Ile Val Leu Thr Gln
1               5                   10                  15

Ser Pro Ala Ser Leu Ala Val Ser Leu Gly Gln Arg Ala Thr Ile Ser
            20                  25                  30

Tyr Arg Ala Ser Lys Ser Val Ser Thr Ser Gly Tyr Ser Tyr Met His
        35                  40                  45

Trp Asn Gln Gln Lys Pro Gly Gln Pro Pro Arg Leu Leu Ile Tyr Leu
    50                  55                  60

Val Ser Asn Leu Glu Ser Gly Val Pro Ala Arg Phe Ser Gly Ser Gly
65                  70                  75                  80

Ser Gly Thr Asp Phe Thr Leu Asn Ile His Pro Val Glu Glu Glu Asp
                85                  90                  95

Ala Ala Thr Tyr Tyr Cys Ser His Ile Arg Glu Leu Thr Arg
            100                 105                 110

<210> SEQ ID NO 155
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Leu Gln Leu Gly Val Leu Leu Leu Trp Val Pro Gly Ser Thr Gly
1               5                   10                  15
```

-continued

---

```
Asp Ile Val Leu Thr Gln Ser Pro Ala Ser Leu Ala Val Ser Leu Gly
            20                  25                  30

Gln Arg Ala Thr Ile Ser Tyr Arg Ala Ser Lys Ser Val Ser Thr Ser
        35                  40                  45

Gly Tyr Ser Tyr Met His Trp Asn Gln Gln Lys Pro Gly Gln Pro Pro
    50                  55                  60

Arg Leu Leu Ile Tyr Leu Val Ser Asn Leu Glu Ser Gly Val Pro Ala
65                  70                  75                  80

Arg Phe Ser Gly Ser Gly Ser Gly Thr Asp Phe Thr Leu Asn Ile His
                85                  90                  95

Pro Val Glu Glu Glu Asp Ala Ala Thr Tyr Tyr Cys Gln His Ile Arg
            100                 105                 110

Glu Leu Thr Arg
        115
```

```
<210> SEQ ID NO 156
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156
```

```
Gln Leu Gly Val Leu Leu Leu Trp Val Pro Gly Ser Thr Gly Asp Ile
1               5                   10                  15

Val Leu Thr Gln Ser Pro Ala Ser Leu Ala Val Ser Leu Gly Gln Arg
            20                  25                  30

Ala Thr Ile Ser Cys Lys Ala Ser His Ser Val Asp Tyr Asp Gly Asp
        35                  40                  45

Arg Tyr Met Asn Trp Tyr Gln Gln Lys Pro Gly Gln Pro Pro Lys Leu
    50                  55                  60

Leu Ile Tyr Val Ala Ser Asn Leu Glu Cys Gly Ile Pro Ala Arg Phe
65                  70                  75                  80

Ser Gly Ser Gly Cys Gly Thr Asp Phe Thr Leu Asn Ile His Pro Val
                85                  90                  95

Glu Glu Glu Asp Gly Ala Thr Tyr Tyr Cys Gln Arg Ser Asn Glu Asp
            100                 105                 110

Pro Phe
```

```
<210> SEQ ID NO 157
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157
```

```
Arg Gly Asp Ile Leu Leu Thr Gln Phe Pro Ala Ile Leu Ser Val Ser
1               5                   10                  15

Pro Gly Glu Arg Val Ser Phe Ser Cys Arg Ala Ser Gln Ser Ile Gly
            20                  25                  30

Thr Ser Thr His Trp Tyr Gln Gln Lys Pro Gly Gln Pro Pro Arg Ile
        35                  40                  45

Ile Ile Tyr Phe Glu Ser Ile Leu Glu Phe Gly Ala Arg Phe Arg Phe
    50                  55                  60

Ser Gly Thr Gly Ser Gly Thr Asp Phe Thr Leu Asn Ile His Glu Leu
```

```
65                  70                  75                  80

Glu Glu Glu Glu Asp Ala Thr Tyr Gln Tyr Gln His Ile Arg Glu Ile
                85                  90                  95

Thr Arg

<210> SEQ ID NO 158
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Thr Gln Ser Pro Ala Ile Leu Ser Val Ser Pro Gly Glu Arg Val Ser
1               5                   10                  15

Phe Ser Cys Arg Ala Ser Gln Ser Ile Gly Thr Ser Thr His Trp Tyr
                20                  25                  30

Gln Gln Lys Pro Gly Gln Pro Pro Arg Ile Ile Ile Tyr Phe Val Ser
            35                  40                  45

Asn Leu Glu Phe Gly Val Pro Phe Arg Phe Ser Gly Thr Gly Ser Gly
        50                  55                  60

Thr Asp Phe Thr Leu Asn Ile His Gln Leu Glu Glu Glu Asp Asp Ala
65                  70                  75                  80

Thr Tyr His Cys Gln His Ile Arg Glu Leu Thr Arg
                85                  90

<210> SEQ ID NO 159
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Phe Glu Val Gln Leu Gln Glu Ser Gly Pro Glu Leu Val Lys Pro Gly
1               5                   10                  15

Ala Ser Val Lys Val Ser Cys Lys Ala Ser Gly Tyr Ala Phe Thr Ser
                20                  25                  30

Tyr Asn Ile Tyr Trp Val Lys Gln Ser His Gly Lys Ser Leu Glu Trp
            35                  40                  45

Ile Gly Tyr Ile Asp Pro Tyr Asn Gly Gly Thr Thr Tyr Asn Gln Asn
        50                  55                  60

Phe Lys Gly Lys Ala Thr Leu Thr Val Asp Lys Ser Ser Ser Thr Ala
65                  70                  75                  80

Tyr Met His Leu Asn Ser Leu Thr Ser Glu Asp Ser Ala Val Tyr Tyr
                85                  90                  95

Cys Ala Ser Glu Ile Tyr Tyr Asp Tyr Gly Gly Arg Phe Ala Tyr Trp
            100                 105                 110

Gly Gln Gly Thr Leu Val Thr Val Ser Ala Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175
```

-continued

```
Ala Val Leu Gln
        180

<210> SEQ ID NO 160
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Tyr Asn Glu Lys Phe Thr Gly Lys Ala Thr Leu Thr Ala Asp Lys Ser
1               5                   10                  15

Ser Ser Thr Ala Tyr Met Gln Leu Ser Ser Leu Thr Ser Glu Asp Ser
            20                  25                  30

Ala Val Tyr Phe Cys Ala Arg Glu Glu Tyr Asp Tyr Asp Glu Gly Tyr
            35                  40                  45

Ala Met Asp Tyr Trp Gly Gln Gly Thr Ser Val Thr Val Ser Ser Ala
        50                  55                  60

Lys Thr Thr Pro Pro Ser Val Tyr Pro Leu Ala Pro Gly Ser Ala Ala
65                  70                  75                  80

Gln Thr Asn Ser Met Val Thr Leu Gly Cys Leu Val Lys Gly Tyr Phe
                85                  90                  95

Pro Glu Pro Val Thr Val Thr Trp Asn Ser Gly Ser Leu Ser Ser Gly
            100                 105                 110

Val His Thr
        115

<210> SEQ ID NO 161
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Glu Ser Gly Ala Glu Leu Val Lys Pro Gly Ala Ser Val
1               5                   10                  15

Lys Leu Ser Cys Lys Ala Ser Gly Tyr Thr Phe Thr Ser Gln Trp Met
            20                  25                  30

Gln Trp Val Arg Gln Arg Pro Gly Gln Gly Leu Glu Trp Ile Gly Glu
            35                  40                  45

Ile Asn Pro Ser Ser Gly Arg Thr His Tyr Asn Glu Lys Phe Lys Thr
        50                  55                  60

Lys Ala Thr Leu Thr Val Asp Lys Ser Ser Ser Thr Ala Tyr Met Gln
65                  70                  75                  80

Leu Ser Ser Leu Thr Ser Glu Asp Ser Ala Val Tyr Tyr Cys Ala Arg
                85                  90                  95

Gly Asp Gly Asp Tyr Val Trp Phe Ala Tyr Trp Gly Gln Gly Thr Leu
            100                 105                 110

Val Thr Val Ser Ala Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
        130                 135                 140

Leu Val Lys Gly Tyr Phe Pro Glu Pro Val Thr Val Thr Trp Asn Ser
145                 150                 155                 160
```

-continued

Gly Ser Leu Ser Ser Gly Val His Thr Phe Pro Ala Val Leu Gln
                165                 170                 175

<210> SEQ ID NO 162
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Tyr Trp Asn Trp Ile Arg Lys Phe Pro Gly Asn Lys Leu Glu Tyr Met
1               5                   10                  15

Gly Tyr Ile Ser Tyr Ser Gly Ser Thr Tyr Tyr Asn Pro Ser Leu Lys
                20                  25                  30

Ser Arg Ile Ser Ile Thr Arg Asp Thr Ser Lys Asn Gln Tyr Ser Leu
            35                  40                  45

His Leu Asn Ser Val Thr Ala Glu Asp Thr Ala Thr Phe Tyr Cys Ala
    50                  55                  60

Arg Tyr Tyr Gly Asp Asn Tyr Val Gly Ala Met Asp Tyr Trp Gly Gln
65                  70                  75                  80

Gly Thr Ser Val Thr Val Ser Ser Ala Lys Thr Thr Ala Pro Ser Val
                85                  90                  95

Tyr Pro Leu Ala Pro Val Cys Gly Asp Thr Thr Gly Ser Ser Val Thr
                100                 105                 110

Leu Gly Cys Leu Val Lys Gly Tyr Phe Pro Glu Pro Val Thr Leu Thr
            115                 120                 125

Trp Asn Ser Gly Ser Leu Ser Ser Gly Val
    130                 135

<210> SEQ ID NO 163
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Leu Leu Trp Val Pro Gly Ser Thr Gly Asp Ile Val Leu Thr Gln Ser
1               5                   10                  15

Pro Ala Ser Leu Ala Val Ser Leu Gly Gln Arg Ala Thr Ile Ser Tyr
                20                  25                  30

Arg Ala Ser Lys Ser Val Ser Thr Ser Gly Tyr Ser Tyr Met His Trp
            35                  40                  45

Asn Gln Gln Lys Pro Gly Gln Pro Pro Arg Leu Leu Ile Tyr Leu Val
    50                  55                  60

Ser Asn Leu Glu Ser Gly Val Pro Ala Arg Phe Ser Gly Ser Gly Ser
65                  70                  75                  80

Gly Thr Asp Phe Thr Leu Asn Ile His Pro Val Glu Glu Glu Asp Ala
                85                  90                  95

Ala Thr Tyr Tyr Cys
            100

<210> SEQ ID NO 164
<211> LENGTH: 103
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 164

Leu Leu Leu Trp Val Pro Gly Ser Thr Gly Asp Ile Val Leu Thr Gln
1               5                   10                  15

Ser Pro Ala Ser Leu Ala Val Ser Leu Gly Gln Arg Ala Thr Ile Ser
            20                  25                  30

Tyr Arg Ala Ser Lys Ser Val Ser Thr Ser Gly Tyr Ser Tyr Met His
        35                  40                  45

Trp Asn Gln Gln Lys Pro Gly Gln Pro Pro Arg Leu Leu Ile Tyr Leu
    50                  55                  60

Val Ser Asn Leu Glu Ser Gly Val Pro Ala Arg Phe Ser Gly Ser Gly
65                  70                  75                  80

Ser Gly Thr Asp Phe Thr Leu Asn Ile His Pro Val Glu Glu Glu Asp
                85                  90                  95

Ala Ala Thr Tyr Tyr Cys His
            100

<210> SEQ ID NO 165
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

His Arg Thr Phe Tyr Phe Gln Leu Cys Leu Val Leu Leu Trp Leu Ser
1               5                   10                  15

Gly Ile Val Leu Thr Gln Ser Pro Ala Ser Leu Ala Val Ser Leu Gly
            20                  25                  30

Gln Arg Ala Thr Ile Ser Tyr Arg Ala Ser Lys Ser Val Ser Thr Ser
        35                  40                  45

Gly Tyr Ser Tyr Met His Trp Asn Gln Gln Lys Pro Gly Gln Pro Pro
    50                  55                  60

Arg Leu Leu Ile Tyr Leu Val Ser Asn Leu Glu Ser Gly Val Pro Ala
65                  70                  75                  80

Arg Phe Ser Gly Ser Gly Ser Gly Thr Asp Phe Thr Leu Asn Ile His
                85                  90                  95

Pro Val Glu Glu Glu Asp Ala Ala Thr Tyr Tyr Cys Gln His Ile Arg
            100                 105                 110

Glu Leu Thr Arg
        115

<210> SEQ ID NO 166
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ile Val Leu Thr Gln Ser Pro Ala Ser Leu Ala Val Ser Leu Gly Gln
1               5                   10                  15

Arg Ala Thr Ile Ser Tyr Arg Ala Ser Lys Ser Val Ser Thr Ser Gly
            20                  25                  30
```

-continued

```
Tyr Ser Tyr Met His Trp Asn Gln Gln Lys Pro Gly Gln Pro Pro Arg
        35              40              45

Leu Leu Ile Tyr Leu Val Ser Asn Leu Glu Ser Gly Val Pro Ala Arg
        50              55              60

Phe Ser Gly Ser Gly Ser Gly Thr Asp Phe Thr Leu Asn Ile His Pro
65              70              75              80

Val Glu Glu Glu Asp Ala Ala Thr Tyr Tyr Cys Gln His Ile Arg Glu
                85              90              95

Leu Thr Arg Ser Glu Gly Gly Pro Ser
            100             105

<210> SEQ ID NO 167
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Phe Pro Pro Ser Ser Glu Gln Leu Thr Ser Gly Gly Ala Ser Val Met
1               5               10              15

Leu Leu Leu Trp Val Pro Gly Ser Thr Gly Asp Ile Val Leu Thr Gln
            20              25              30

Ser Pro Ala Ser Leu Ala Val Ser Leu Gly Gln Arg Ala Thr Ile Ser
        35              40              45

Tyr Arg Ala Ser Lys Ser Val Ser Thr Ser Gly Tyr Ser Tyr Met His
    50              55              60

Trp Asn Gln Gln Lys Pro Gly Gln Pro Pro Arg Leu Leu Ile Tyr Leu
65              70              75              80

Val Ser Asn Leu Glu Ser Gly Val Pro Ala Arg Phe Ser Gly Ser Gly
                85              90              95

Ser Gly Thr Asp Phe Thr Leu Asn Ile His Pro Val Glu Glu Glu Asp
            100             105             110

Ala
```